(12) United States Patent
Muratoglu et al.

(10) Patent No.: US 8,293,811 B2
(45) Date of Patent: Oct. 23, 2012

(54) METHODS FOR MAKING OXIDATION-RESISTANT CROSS-LINKED POLYMERIC MATERIALS

(75) Inventors: Orthun K. Muratoglu, Cambridge, MA (US); Edward T. Kopesky, Arlington, MA (US); Ebru Oral, Newton, MA (US)

(73) Assignees: The General Hospital Corporation, Boston, MA (US); Cambridge Polymer Group, Inc., Boston, MA (US)

( * ) Notice: Subject to any disclaimer, the term of this patent is extended or adjusted under 35 U.S.C. 154(b) by 242 days.

(21) Appl. No.: 12/522,728

(22) PCT Filed: Jan. 25, 2008

(86) PCT No.: PCT/US2008/092047
§ 371 (c)(1),
(2), (4) Date: Apr. 5, 2010

(87) PCT Pub. No.: WO2008/092047
PCT Pub. Date: Jul. 31, 2008

(65) Prior Publication Data
US 2010/0190882 A1    Jul. 29, 2010

Related U.S. Application Data

(60) Provisional application No. 60/886,527, filed on Jan. 25, 2007, provisional application No. 60/889,037, filed on Feb. 9, 2007, provisional application No. 60/892,346, filed on Mar. 1, 2007.

(51) Int. Cl.
| | |
|---|---|
| C08F 2/46 | (2006.01) |
| C08J 3/28 | (2006.01) |
| A61F 2/02 | (2006.01) |
| A61F 2/30 | (2006.01) |
| A61L 27/50 | (2006.01) |
| A61L 27/16 | (2006.01) |
| C08L 23/06 | (2006.01) |
| C08K 5/1545 | (2006.01) |

(52) U.S. Cl. .............. 522/161; 522/75; 522/79; 522/80; 522/74; 522/71; 522/157; 522/150; 522/158; 522/111; 522/112; 523/113; 523/115; 523/300; 524/100; 524/585; 524/587; 623/11.11

(58) Field of Classification Search .............. 522/79, 522/80, 74, 71, 161, 157, 150, 158, 75, 111, 522/112; 623/11.11; 523/113, 115, 300; 524/100, 585, 587; 526/352

See application file for complete search history.

(56) References Cited

U.S. PATENT DOCUMENTS

| | | | | |
|---|---|---|---|---|
| 5,055,328 | A | | 10/1991 | Evert et al. .................. 428/34.9 |
| 5,414,049 | A | * | 5/1995 | Sun et al. .................... 525/333.7 |
| 5,753,182 | A | * | 5/1998 | Higgins ......................... 422/23 |
| 5,879,400 | A | * | 3/1999 | Merrill et al. .............. 623/22.11 |
| 6,184,264 | B1 | * | 2/2001 | Webster ......................... 522/182 |
| 6,228,900 | B1 | * | 5/2001 | Shen et al. .................... 522/153 |
| 6,277,390 | B1 | * | 8/2001 | Schaffner ...................... 424/422 |
| 6,448,315 | B1 | | 9/2002 | Lidgren et al. ................ 524/110 |
| 6,562,540 | B2 | * | 5/2003 | Saum et al. .................... 430/130 |
| 6,620,198 | B2 | * | 9/2003 | Burstein et al. ............ 623/20.28 |
| 6,641,617 | B1 | * | 11/2003 | Merrill et al. .............. 623/23.58 |
| 6,692,679 | B1 | * | 2/2004 | McNulty et al. .............. 522/161 |
| 6,818,172 | B2 | * | 11/2004 | King et al. .................... 264/479 |
| 7,431,874 | B2 | * | 10/2008 | Muratoglu et al. ........... 264/235 |
| 7,498,365 | B2 | * | 3/2009 | Muratoglu et al. ............ 524/81 |
| 7,790,095 | B2 | * | 9/2010 | Muratoglu et al. ........... 264/488 |
| 7,846,376 | B2 | * | 12/2010 | Abt et al. ...................... 264/494 |
| 7,863,348 | B2 | * | 1/2011 | Abt et al. ...................... 523/113 |
| 7,906,064 | B2 | * | 3/2011 | Muratoglu et al. ........... 264/494 |
| 2003/0127168 | A1 | | 7/2003 | Ishida |
| 2003/0208278 | A1 | * | 11/2003 | Richard ...................... 623/20.14 |
| 2003/0212161 | A1 | * | 11/2003 | McKellop et al. ................ 522/3 |
| 2004/0156879 | A1 | * | 8/2004 | Muratoglu et al. ........... 424/423 |
| 2005/0194722 | A1 | * | 9/2005 | Muratoglu et al. ........... 264/488 |
| 2005/0194723 | A1 | * | 9/2005 | Muratoglu et al. ........... 264/488 |
| 2005/0194724 | A1 | | 9/2005 | Muratoglu et al. |
| 2007/0114702 | A1 | * | 5/2007 | Muratoglu et al. ........... 264/479 |
| 2008/0067724 | A1 | * | 3/2008 | Muratoglu et al. ........... 264/496 |
| 2008/0090934 | A1 | * | 4/2008 | Muratoglu et al. ........... 522/161 |
| 2008/0215142 | A1 | * | 9/2008 | Muratoglu et al. .......... 623/1.49 |
| 2009/0030524 | A1 | * | 1/2009 | Schroeder et al. ......... 623/23.59 |

* cited by examiner

Primary Examiner — Sanza McClendon
(74) Attorney, Agent, or Firm — Perkins Coie LLP

(57) ABSTRACT

The present invention relates to methods for making cross-linked oxidation-resistant polymeric materials and preventing or minimizing in vivo elution of antioxidant from the antioxidant-containing polymeric materials. The invention also provides methods of doping polymeric materials with a spatial control of cross-linking and antioxidant distribution, for example, vitamin E (α-Tocopherol), and methods for extraction/elution of antioxidants, for example, vitamin E (α-tocopherol), from surface regions of antioxidant-containing polymeric materials, and materials used therewith also are provided.

102 Claims, 47 Drawing Sheets

METHODS FOR MAKING OXIDATION-RESISTANT CROSS-LINKED POLYMERIC MATERIALS

This application is a 371 of International Application No. PCT/US2008/051982 filed Jan. 25, 2008, which claims priority to Provisional Application No. 60/886,527 filed Jan. 25, 2007, Provisional Application No. 60/889,037 filed Feb. 9, 2007, and Provisional Application No. 60/892,346 filed Mar. 1, 2007. The entire contents of the above-identified applications are hereby incorporated by reference.

FIELD OF THE INVENTION

The present invention relates to methods for making oxidation-resistant cross-linked polymeric materials that contains antioxidants and preventing or minimizing in vivo elution of antioxidant from the antioxidant-containing polymeric materials. Methods of doping polymeric materials with a spatial control of antioxidant distribution and/or with a spatial control of cross-linking, and methods of extraction of antioxidants from antioxidant-containing polymeric materials, and materials that can be used therewith also are provided.

BACKGROUND OF THE INVENTION

Polymeric material, such as ultra-high molecular weight polyethylene (UHMWPE), is used in load bearing applications. In humans, it can be used in total joint prostheses. Wear of the polyethylene components over years is known to compromise the longevity and performance of total joints in the long-term. Radiation cross-linking has been shown to reduce the wear rate of polyethylene and thus extend the longevity of total joint reconstructions. Radiation cross-linking also generates residual free radicals, which are known to cause oxidation and embrittlement in the long-term. Therefore, it is crucial to either eliminate or stabilize the free radicals so that deleterious oxidation is avoided or minimized. One method of free radical elimination through irradiation and melting were described by Merrill et al. (see U.S. Pat. No. 5,879,400). This is an acceptable and widely used method; however, such a melt history also reduces the crystallinity of the polyethylene and thus affects its mechanical and fatigue properties (see Oral et al., Biomaterials, 27:917-925 (2006)).

Other methods that avoids melting after irradiation is the one described, among other things, by Muratoglu and Spiegelberg (see U.S. application Ser. No. 10/757,551, filed Jan. 15, 2004; US 2004/0156879). These methods use an anti-oxidant, such as α-tocopherol, to stabilize the free radicals in irradiated polymeric material and prevent long-term oxidation. According to certain embodiments of these methods, α-tocopherol can be incorporated into polymeric material after irradiation through contact and diffusion.

α-Tocopherol can be used to lessen or eliminate reactivity of the residual free radicals in irradiated UHMWPE to prevent oxidation. The incorporation of α-tocopherol into irradiated UHMWPE can be achieved through either blending α-tocopherol with the UHMWPE powder prior to consolidation or diffusing the α-tocopherol into UHMWPE after consolidation of powder, both of which are taught in U.S. application Ser. No. 10/757,551. The latter also can be performed after the consolidated UHMWPE is irradiated. Since radiation cross-links the UHMWPE and thus increases its wear resistance, it can be beneficial to irradiate the consolidated UHMWPE in its virgin state without any α-tocopherol present. On the other hand, cross-linking has been shown to decrease certain mechanical properties and fatigue resistance of UHMWPE (see Oral et al., Mechanisms of decrease in fatigue crack propagation resistance in irradiated and melted UHMWPE, Biomaterials, 27 (2006) 917-925). Wear of UHMWPE in joint arthroplasty is a surface phenomenon whereas fatigue crack propagation resistance is largely a property of the bulk, other than the surface. Therefore, UHMWPE with high cross-linking on the surface and less cross-linking in the bulk can be beneficial as an alternate bearing in joint arthroplasty. Oral et al. (Characterization of irradiated blends of α-tocopherol and UHMWPE, Biomaterials, 26 (2005) 6657-6663) have shown that when present in UHMWPE, α-tocopherol reduces the efficiency of cross-linking of the polymer during irradiation. Spatial control of vitamin E concentration followed by irradiation can spatially control cross-linking as well. It can be desirable to add α-tocopherol after radiation cross-linking if high cross-linking is desired and that is possible by diffusing α-tocopherol into irradiated and consolidated UHMWPE. Diffusion and penetration depth in irradiated UHMWPE has been discussed. Muratoglu et al. (see U.S. application Ser. No. 10/757,551, filed Jan. 15, 2004; US 2004/0156879) described, among other things, high temperature doping and/or annealing steps to increase the depth of penetration of α-tocopherol into irradiated UHMWPE. Muratoglu et al. (see U.S. Provisional Application Ser. No. 60/709,795, filed Aug. 22, 2005) described annealing in supercritical carbon dioxide to increase depth of penetration of α-tocopherol into irradiated UHMWPE. UHMWPE medical implants can have a thickness of up to 30 mm and sometimes larger. Penetrating such large implants with α-tocopherol by diffusion can take a long time, however. Also, it is preferable in some embodiments to diffuse α-tocopherol into an irradiated UHMWPE preform and subsequently machine that preform to obtain the finished implant. The preform has to be larger than the implant and therefore the diffusion path for α-tocopherol is increased.

A similar problem is often observed with polyethylene components that are fabricated with an integral metal piece. Often the metal piece is porous to allow bone in-growth for the fixation of the implant. In others, the metal piece is not porous and may be used to increase the structural integrity of the polyethylene piece. Therefore in the presence of an integral metallic piece the diffusion of α-tocopherol will either be slowed down near the surface covered with the porous metals or inhibited near the surface covered by a non-porous metal plate or rod.

It can be beneficial to have α-tocopherol present throughout the polymeric article to stabilize all free radicals and prevent long-term oxidation induced mechanical property changes.

In order to eliminate free radicals, several further methods can be used such as melting (see Muratoglu et al. U.S. application Ser. No. 10/757,551), mechanical deformation and recovery (see Muratoglu et al., U.S. application Ser. No. 11/030,115) or high pressure crystallization (see Muratoglu et al. U.S. application Ser. No. 10/597,652).

In order to increase the strength of UHMWPE, high pressure crystallization (HPC) of UHMWPE has been proposed. (See Bistolfi et al., Transactions of the Orthopaedic Research Society, 2005. 240; Oral et al., Transactions of the Orthopaedic Research Society, 2005. p. 988.; Muratoglu et al. U.S. Provisional Application No. 60/541,073, filed Feb. 3, 2004; and PCT/US2005/003305, filed Feb. 3, 2005). High pressure crystallization of unirradiated GUR1050 UHMWPE at above 160° C. and 300 MPa yielded an approximately 70% crystalline UHMWPE, compared to 50-60% for conventional UHMWPE. This is due to a phase transition of the UHMWPE crystals from the orthorhombic to the hexagonal phase at high temperatures and pressures as discussed above. In the hexagonal phase crystals grow to larger sizes and crystallinity increases (see Bassett et al., *J Appl. Phys.*, 1974, 45(10): p. 4146-4150).

It can be advantageous to have α-tocopherol present throughout all or part of the polymeric article in order to stabilize all free radicals and prevent long-term oxidation induced mechanical property changes. It also can be advantageous to have a medical implant, or any polymeric component thereof, doped with a spatial control of antioxidant distribution. This spatial control can be achieved by having gradual changes or step changes in the concentration of antioxidant. It also can be advantageous to have a medical implant with a spatial control of cross-linking. For example, Muratoglu et al. (see U.S. application Ser. No. 10/433,987, filed on Dec. 11, 2001) describe a UHMWPE with gradient cross-linking perpendicular to the irradiation direction by shielding.

This application describes UHMWPE medical implants that have a spatial control of cross-linking due to irradiation of UHMWPE containing a spatially controlled distribution of antioxidant.

High concentrations of antioxidants, for example, α-tocopherol, near the surface of a polymeric material can lead to elution of α-tocopherol into the joint space after implantation. α-tocopherol can elute out of the implants over time, especially at the human joint temperature of about 37.5° C. to 40° C. When stored in air or in water at 40° C., the irradiated and α-tocopherol-doped UHMWPE loses about 10% of the α-tocopherol over about the first six months. The presence of excess α-tocopherol in the joint space may possibly lead to an adverse biological response. In order to avoid such complication, α-tocopherol can be extracted from the polymeric material prior to placement and/or implantation into the body. In order to minimize the elution of α-tocopherol in vivo, a suitable method is necessary to extract the α-tocopherol from the surface regions of an α-tocopherol-containing cross-linked oxidation-resistant polymeric material. However, such achievement were not possible until the present invention.

SUMMARY OF THE INVENTION

The present invention relates generally to methods for cross-linking polymeric materials with spatial control of antioxidant distribution, and products produced thereby. More specifically, the invention relates to methods of making oxidation resistant cross-linked polymeric material by irradiating polymeric materials having a gradient of antioxidant, for example, vitamin E. More specifically, the invention relates to methods of manufacturing antioxidant-doped, non-oxidizing medical device containing cross-linked polymeric material with a spatial distribution of antioxidant and cross-linking throughout the polymeric composition, for example, radiation cross-linked ultra-high molecular weight polyethylene (UHMWPE) with a controlled distribution of antioxidant and materials used therein.

The invention also relates to extraction of antioxidants and methods for making cross-linked oxidation-resistant polymeric materials. Methods for extraction of antioxidants, for example, vitamin E (α-tocopherol), from antioxidant containing consolidated polymeric materials, materials that can be used therewith, and products obtainable thereby, are also provided. The invention also provides methods of making oxidation-resistant cross-linked polymeric material by irradiating a consolidated polymeric material, doping the consolidated polymeric material with an antioxidant, for example, vitamin E, and subsequently eluting or diffusing out a portion of the antioxidant from the cross-linked antioxidant-containing consolidated polymeric material, thereby preventing or minimizing in vivo elution of the antioxidant. More specifically, the invention also relates to methods of manufacturing antioxidant-doped, non-oxidizing medical device containing cross-linked polymeric material by eluting or diffusing out the antioxidant from the surface regions of the cross-linked antioxidant-containing consolidated polymeric composition prior to placement and/or implantation in the body, for example, antioxidant-doped irradiation cross-linked ultra-high molecular weight polyethylene (UHMWPE), materials that can be used therein, and products obtainable thereby.

In one embodiment, the invention provides methods of making an oxidation-resistant cross-linked polymeric material comprising: a) doping a consolidated polymeric material with an antioxidant by diffusion below or above the melting point of the polymeric material, wherein the surface (exterior regions) of the polymeric material is contacted with a lower concentration of antioxidant and bulk (generally the interior regions) of the polymeric material is contacted with a higher concentration of antioxidant than the surface, thereby allowing a spatial distribution of the antioxidant-rich and antioxidant-poor regions; and b) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making an oxidation-resistant cross-linked polymeric material comprising: a) doping a consolidated polymeric material with an antioxidant by diffusion below or above the melting point of the polymeric material, wherein the bulk (generally the interior regions) of the polymeric material is contacted with a lower concentration of antioxidant and surface of the polymeric material is contacted with a higher concentration of antioxidant than the surface, thereby allowing a spatial distribution of the antioxidant-rich and antioxidant-poor regions; and b) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making an oxidation-resistant cross-linked polymeric material comprising: a) doping a consolidated polymeric material with an antioxidant by diffusion below or above the melting point of the polymeric material, wherein the surface (exterior regions) of the polymeric material contains a lower concentration of antioxidant and bulk (generally the interior regions) of the polymeric material contains a higher concentration of antioxidant, thereby allowing a spatial distribution of the antioxidant-rich and antioxidant-poor regions; and b) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making an oxidation-resistant cross-linked polymeric material comprising: a) doping a consolidated polymeric material with an antioxidant by diffusion below or above the melting point of the polymeric material, wherein the bulk of the polymeric material contains a lower concentration of antioxidant and surface of the polymeric material contains a higher concentration of antioxidant, thereby allowing a spatial distribution of the antioxidant-rich and antioxidant-poor regions; and b) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making an oxidation-resistant cross-linked polymeric material comprising: a) doping a consolidated polymeric material with an antioxidant by diffusion below or above the melting point of the polymeric material, b) homogenizing the antioxidant-doped polymeric material by heating to below or above the melt, thereby allowing a spatial distribution of the antioxidant-rich and antioxidant-poor regions; and c) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making an oxidation-resistant cross-linked polymeric material comprising: a) doping a consolidated polymeric material with an antioxidant by diffusion below or above the melting point of the polymeric material, b) homogenizing the antioxidant-doped polymeric material by heating to below or above the melt, thereby allowing a spatial distribution of the antioxidant-rich and antioxidant-poor regions; and c) irradiating the consolidated polymeric material containing the spatially distributed antioxidant with ionizing radiation, thereby forming an oxidation-resistant cross-linked polymeric material having a spatially controlled antioxidant distribution and/or cross-linking.

In another embodiment, the invention provides methods of making a medical implant comprising an oxidation-resistant cross-linked polymeric material comprising: a) doping a consolidated polymeric material with an antioxidant by diffusion below or above the melting point of the polymeric material, wherein the surface of the polymeric material is contacted with a lower concentration of antioxidant and bulk of the polymeric material is contacted with higher concentration of antioxidant, thereby allowing a spatial distribution of the antioxidant-rich and antioxidant-poor regions; b) irradiating the consolidated polymeric material containing the spatially distributed antioxidant with ionizing radiation, thereby forming a cross-linked polymeric material having a spatial distribution of oxidation-resistant regions; and c) machining the consolidated and antioxidant-doped cross-linked polymeric material, thereby forming a medical implant having a spatially controlled distribution of oxidation-resistant regions. The medical implant can be packaged and sterilized.

In another embodiment, the invention provides methods of making a medical implant comprising an oxidation-resistant cross-linked polymeric material comprising: a) doping a consolidated polymeric material with an antioxidant by diffusion below or above the melting point of the polymeric material, wherein the bulk of the polymeric material is contacted with a lower concentration of antioxidant and surface of the polymeric material is contacted with higher concentration of antioxidant, thereby allowing a spatial distribution of the antioxidant-rich and antioxidant-poor regions; b) irradiating the consolidated polymeric material containing the spatially distributed antioxidant with ionizing radiation, thereby forming a cross-linked polymeric material having a spatial distribution of oxidation-resistant regions; and c) machining the consolidated and antioxidant-doped cross-linked polymeric material, thereby forming a medical implant having a spatially controlled distribution of oxidation-resistant regions. The medical implant can be packaged and sterilized.

In another embodiment, the invention provides methods of making a medical implant comprising an oxidation-resistant cross-linked polymeric material comprising: a) doping a consolidated polymeric material with an antioxidant by diffusion below or above the melting point of the polymeric material, wherein the surface of the polymeric material contains a lower concentration of antioxidant and bulk of the polymeric material contains higher concentration of antioxidant, thereby allowing a spatial distribution of the antioxidant-rich and antioxidant-poor regions; b) irradiating the consolidated polymeric material containing the spatially distributed antioxidant with ionizing radiation, thereby forming a cross-linked polymeric material having a spatial distribution of oxidation-resistant regions; and c) machining the consolidated and antioxidant-doped cross-linked polymeric material, thereby forming a medical implant having a spatially controlled distribution of oxidation-resistant regions. The medical implant can be packaged and sterilized.

In another embodiment, the invention provides methods of making a medical implant comprising an oxidation-resistant cross-linked polymeric material comprising: a) doping a consolidated polymeric material with an antioxidant by diffusion below or above the melting point of the polymeric material, wherein the bulk of the polymeric material contains a lower concentration of antioxidant and surface of the polymeric material contains higher concentration of antioxidant, thereby allowing a spatial distribution of the antioxidant-rich and antioxidant-poor regions; b) irradiating the consolidated polymeric material containing the spatially distributed antioxidant with ionizing radiation, thereby forming a cross-linked polymeric material having a spatial distribution of oxidation-resistant regions; and c) machining the consolidated and antioxidant-doped cross-linked polymeric material, thereby forming a medical implant having a spatially controlled distribution of oxidation-resistant regions. The medical implant can be packaged and sterilized.

In another embodiment, the invention provides methods of making a medical implant comprising an oxidation-resistant cross-linked polymeric material comprising: a) doping a consolidated polymeric material with an antioxidant by diffusion below or above the melting point of the polymeric material, b) homogenizing the antioxidant-doped polymeric material by heating to below or above the melt, thereby allowing a spatial distribution of the antioxidant-rich and antioxidant-poor regions; c) irradiating the consolidated polymeric material containing the spatially distributed antioxidant with ionizing radiation, thereby forming a cross-linked polymeric material having a spatial distribution of oxidation-resistant regions; and d) machining the consolidated and antioxidant-doped cross-linked polymeric material, thereby forming a medical implant having a spatially controlled distribution of oxidation-resistant regions. The medical implant can be packaged and sterilized.

In another embodiment, the invention provides methods of making an oxidation-resistant cross-linked polymeric material comprising: a) blending a polymeric material with an antioxidant, wherein a portion of the polymeric material is contacted with a lower concentration of antioxidant and portion of the polymeric material is contacted with a higher concentration of antioxidant, thereby allowing a spatial distribution of the antioxidant-rich and antioxidant-poor regions; b) consolidating the antioxidant blended polymeric material, thereby forming a medical implant preform; and c) irradiating the medical implant preform containing the spatially distributed antioxidant with ionizing radiation, thereby forming a medical implant preform having an oxidation-resistant cross-linked polymeric material having a spatially controlled cross-linking and antioxidant distribution.

In another embodiment, the invention provides methods of making a medical implant comprising an oxidation-resistant cross-linked polymeric material comprising: a) blending a polymeric material with an antioxidant, wherein a first portion of the polymeric material is contacted with a lower concentration of antioxidant and a second portion of the polymeric material is contacted with a higher concentration of antioxidant than the first portion, thereby allowing a spatial distribution of the antioxidant-rich and antioxidant-poor regions; b) consolidating the antioxidant blended polymeric material, thereby forming a medical implant preform; c) irradiating the medical implant preform containing the spatially distributed antioxidant with ionizing radiation, thereby forming an oxidation-resistant cross-linked medical implant preform having a spatially controlled antioxidant distribution; and d) machining the oxidation-resistant cross-linked medical implant preform having the spatially controlled antioxidant distribution, thereby forming an oxidation-resistant cross-linked medical implant having a spatially controlled antioxidant distribution and/or cross-linking. The medical implant can be packaged and sterilized.

In another embodiment, the invention provides methods of making a medical implant comprising an oxidation-resistant cross-linked polymeric material comprising: a) blending a polymeric material with an antioxidant, wherein a first portion of the polymeric material contains a lower concentration of antioxidant and a second portion of the polymeric material contains a higher concentration of antioxidant than the first portion, thereby allowing a spatial distribution of the antioxidant-rich and antioxidant-poor regions; b) consolidating the antioxidant blended polymeric material, thereby forming a medical implant preform; c) irradiating the medical implant preform containing the spatially distributed antioxidant with ionizing radiation, thereby forming an oxidation-resistant cross-linked medical implant preform having a spatially controlled antioxidant distribution; and d) machining the oxidation-resistant cross-linked medical implant preform having the spatially controlled antioxidant distribution, thereby forming an oxidation-resistant cross-linked medical implant having a spatially controlled antioxidant distribution and/or cross-linking. The medical implant can be packaged and sterilized.

In another embodiment, the invention provides methods of making a medical implant comprising an oxidation-resistant cross-linked polymeric material comprising: a) blending a polymeric material with an antioxidant, wherein a first portion of the polymeric material is contacted with a lower concentration of antioxidant and a second portion of the polymeric material is contacted with a higher concentration of antioxidant than the first portion, thereby allowing a spatial distribution of the antioxidant-rich and antioxidant-poor regions; b) consolidating the antioxidant blended polymeric material, thereby forming a medical implant preform; c) machining the medical implant preform having a spatial distribution of antioxidant, thereby forming an oxidation-resistant medical implant having a spatially controlled antioxidant distribution; and d) irradiating the oxidation-resistant medical implant preform containing the spatially distributed antioxidant with ionizing radiation, thereby forming an oxidation-resistant cross-linked medical implant having a spatially controlled antioxidant distribution and/or cross-linking. The medical implant can be packaged and sterilized.

In another embodiment, the invention provides methods of making a medical implant comprising: a) blending one or more types of resin, flakes, or powder with different concentrations of an antioxidant, wherein a first portion of the resin, flakes, or powder are contacted with a lower concentration of antioxidant and a second portion of the resin, flakes, or powder are contacted with a higher concentration of antioxidant than the first portion, thereby allowing a spatial distribution of the antioxidant-rich and antioxidant-poor regions; b) consolidating the antioxidant-blended resin, flakes, or powder, thereby forming a medical implant preform; c) irradiating the oxidation-resistant medical implant preform containing the spatially distributed antioxidant with ionizing radiation, thereby forming an oxidation-resistant medical implant preform having a spatially controlled cross-linking and antioxidant distribution; and d) machining the medical implant preform having a spatial distribution of cross-linking and antioxidant, thereby forming an oxidation-resistant medical implant having a spatially controlled cross-linking and antioxidant distribution. The medical implant can be packaged and sterilized.

In another embodiment, the invention provides methods of making a medical implant comprising: a) blending two or more types of resin, flakes, or powder with different concentrations of an antioxidant, wherein a portion of the resin, flakes, or powder are contacted with a lower concentration of antioxidant and portion of the resin, flakes, or powder are contacted with a higher concentration of antioxidant, thereby allowing a spatial distribution of the antioxidant-rich and antioxidant-poor regions; b) consolidating the antioxidant-blended resin, flakes, or powder, thereby forming a medical implant preform; c) irradiating the oxidation-resistant medical implant preform containing the spatially distributed antioxidant with ionizing radiation, thereby forming an oxidation-resistant medical implant preform having a spatially controlled cross-linking and antioxidant distribution; and d) machining the medical implant preform having a spatial distribution of cross-linking and antioxidant, thereby forming an oxidation-resistant medical implant having a spatially controlled cross-linking and antioxidant distribution. The medical implant can be packaged and sterilized.

In another embodiment, the invention provides methods of making a medical implant comprising: a) blending one or more types of resin, flakes, or powder with different concentrations of an antioxidant, wherein a portion of the resin, flakes, or powder are contacted with a lower concentration of antioxidant and portion of the resin, flakes, or powder are contacted with a higher concentration of antioxidant, thereby allowing a spatial distribution of the antioxidant-rich and antioxidant-poor regions; b) consolidating the antioxidant-blended resin, flakes, or powder, thereby forming a medical implant preform; c) machining the medical implant preform having a spatial distribution of antioxidant, thereby forming an oxidation-resistant medical implant having a spatially controlled antioxidant distribution; and d) irradiating the oxidation-resistant medical implant containing the spatially distributed antioxidant with ionizing radiation, thereby forming an oxidation-resistant medical implant having a spatially controlled cross-linking and antioxidant distribution. The medical implant can be packaged and sterilized.

In some embodiments, the medical implant preform is irradiated and subsequently machined to obtain the final medical implant shape. In some embodiments, the blends of resin, flakes, or powder contain the same concentration of antioxidant.

According to another embodiment, the invention provides methods of making a medical implant as described in various embodiments, wherein the surface of the polymeric material is contacted with no or low concentration of antioxidant and bulk of the polymeric material is contacted with a higher concentration of antioxidant.

In one embodiment, the invention provides methods of making an oxidation-resistant cross-linked polymeric material, wherein a cross-linked polymeric material having a spatially controlled antioxidant distribution and/or cross-linking can be further treated by: a) heating to above the melting point of the polymeric material; b) pressurizing the heated polymeric material to at least 0.001-1000 MPa; c) keeping at this pressure and temperature; d) cooling down to below the melting point of the polymeric material under pressure; and e) releasing the pressure to about ambient pressure.

In another embodiment, the invention provides methods of making an oxidation-resistant cross-linked polymeric material comprising, wherein a cross-linked polymeric material having a spatially controlled antioxidant distribution and/or cross-linking can be further treated by: a) pressurizing the polymeric material to at least 0.001-1000 MPa; b) heating the pressurized polymeric material to below the melting point of the pressurized polymeric material; c) keeping at this pressure and temperature; d) cooling down to below the melting point of the polymeric material under pressure; and e) releasing the pressure to about ambient pressure.

In another embodiment, the invention provides methods of making an oxidation-resistant cross-linked polymeric material comprising: a) blending a polymeric material with an antioxidant; b) consolidating the antioxidant-blended polymeric material, thereby forming an oxidation-resistant polymeric material; c) irradiating the consolidated oxidation-resistant polymeric material with ionizing radiation, thereby forming an oxidation-resistant cross-linked polymeric material; and d) extracting or eluting the antioxidant from the surface regions of the oxidation-resistant cross-linked polymeric material, thereby preventing or minimizing in vivo elution of the antioxidant.

In another embodiment, the invention provides methods of making a medical implant comprising an oxidation-resistant cross-linked medical implant comprising: a) blending a polymeric material with an antioxidant; b) consolidating the antioxidant-blended polymeric material, thereby forming an oxidation-resistant consolidated polymeric material; c) irradiating the consolidated oxidation-resistant polymeric material with ionizing radiation, thereby forming an oxidation-resistant cross-linked consolidated polymeric material; d) machining the consolidated and antioxidant-resistant cross-linked polymeric material, thereby forming an oxidation-resistant cross-linked medical implant having oxidation-resistant regions; and e) extracting or eluting the antioxidant from the surface regions of the oxidation-resistant cross-linked medical implant prior to placement and/or implantation into the body, thereby preventing or minimizing in vivo elution of the antioxidant from the oxidation-resistant cross-linked medical implant. The medical implant can be packaged and sterilized.

In another embodiment, the invention provides methods of making an oxidation-resistant cross-linked medical implant preform comprising: a) blending a polymeric material with an antioxidant; b) consolidating the antioxidant-blended polymeric material, thereby forming an oxidation-resistant medical implant preform; c) irradiating the oxidation-resistant medical implant preform with ionizing radiation, thereby forming a medical implant preform having an oxidation-resistant cross-linked polymeric material; and d) extracting or eluting the antioxidant from the surface regions of the oxidation-resistant cross-linked medical implant preform, thereby preventing or minimizing in vivo elution of the antioxidant. The medical implant can be packaged and sterilized.

In another embodiment, the invention provides methods of making a medical implant comprising an oxidation-resistant cross-linked medical implant comprising: a) blending a polymeric material with an antioxidant; b) consolidating the antioxidant-blended polymeric material, thereby forming an oxidation-resistant consolidated polymeric material; c) machining the consolidated and antioxidant-resistant polymeric material, thereby forming an oxidation-resistant medical implant; d) irradiating the oxidation-resistant medical implant with ionizing radiation, thereby forming an oxidation-resistant cross-linked medical implant; and e) extracting or eluting the antioxidant from the surface regions of the oxidation-resistant cross-linked medical implant prior to placement and/or implantation into the body, thereby preventing or minimizing in vivo elution of the antioxidant from the oxidation-resistant cross-linked medical implant. The medical implant can be packaged and sterilized.

In another embodiment, the invention provides methods of making an oxidation-resistant cross-linked polymeric material comprising: a) doping a consolidated polymeric material with an antioxidant below or above the melting point of the polymeric material, thereby forming an oxidation-resistant polymeric material; b) irradiating the consolidated oxidation-resistant polymeric material with ionizing radiation, thereby forming an oxidation-resistant cross-linked consolidated polymeric material; and c) extracting or eluting the antioxidant from the surface regions of the oxidation-resistant cross-linked consolidated polymeric material, thereby preventing or minimizing in vivo elution of the antioxidant.

In another embodiment, the invention provides methods of making an oxidation-resistant cross-linked medical implant comprising: a) doping a consolidated polymeric material with an antioxidant above or below the melting point of the polymeric material, thereby forming an oxidation-resistant polymeric material; b) irradiating the consolidated oxidation-resistant polymeric material with ionizing radiation, thereby forming an oxidation-resistant cross-linked consolidated polymeric material; c) machining the consolidated and antioxidant-resistant polymeric material, thereby forming an oxidation-resistant cross-linked medical implant; and d) extracting or eluting the antioxidant from the surface regions of the oxidation-resistant cross-linked medical implant prior to placement and/or implantation into the body, thereby preventing or minimizing in vivo elution of the antioxidant. The medical implant can be packaged and sterilized.

In another embodiment, the invention provides methods of making an oxidation-resistant cross-linked polymeric material comprising: a) blending a polymeric material with an antioxidant; b) consolidating the antioxidant-blended polymeric material, thereby forming an oxidation-resistant polymeric material; c) extracting or eluting the antioxidant from the surface regions of the oxidation-resistant polymeric material, thereby preventing or minimizing in vivo elution of the antioxidant; and d) irradiating the consolidated oxidation-resistant polymeric material with ionizing radiation, thereby forming an oxidation-resistant cross-linked polymeric material.

In another embodiment, the invention provides methods of making a medical implant comprising an oxidation-resistant cross-linked medical implant comprising: a) blending a polymeric material with an antioxidant; b) consolidating the antioxidant-blended polymeric material, thereby forming an oxidation-resistant consolidated polymeric material; c) extracting or eluting the antioxidant from the surface regions of the oxidation-resistant consolidated polymeric material, thereby preventing or minimizing in vivo elution of the antioxidant from the consolidated polymeric material; d) irradiating the consolidated oxidation-resistant polymeric material with ionizing radiation, thereby forming an oxidation-resistant cross-linked consolidated polymeric material; and e) machining the consolidated and antioxidant-resistant cross-linked polymeric material, thereby forming an oxidation-resistant cross-linked medical implant. The medical implant can be packaged and sterilized.

In another embodiment, the invention provides methods of making an oxidation-resistant cross-linked medical implant preform comprising: a) blending a polymeric material with an antioxidant; b) consolidating the antioxidant-blended polymeric material, thereby forming an oxidation-resistant medical implant preform; c) extracting or eluting the antioxidant from the surface regions of the oxidation-resistant polymeric material, thereby preventing or minimizing in vivo elution of the antioxidant; d) irradiating the oxidation-resistant medical implant preform with ionizing radiation, thereby forming a medical implant preform having an oxidation-resistant cross-linked polymeric material. The medical implant can be packaged and sterilized.

In another embodiment, the invention provides methods of making a medical implant comprising an oxidation-resistant cross-linked medical implant comprising: a) blending the polymeric material with an antioxidant; b) consolidating the antioxidant-blended polymeric material, thereby forming an oxidation-resistant consolidated polymeric material; c) machining the consolidated and antioxidant-resistant polymeric material, thereby forming an oxidation-resistant medical implant; d) extracting or eluting the antioxidant from the surface regions of the oxidation-resistant medical implant, thereby preventing or minimizing in vivo elution of the antioxidant from the oxidation-resistant medical implant; and e) irradiating the oxidation-resistant medical implant with ionizing radiation, thereby forming an oxidation-resistant cross-linked medical implant. The medical implant can be packaged and sterilized.

In another embodiment, the invention provides methods of making an oxidation-resistant cross-linked polymeric material comprising: a) doping a consolidated polymeric material with an antioxidant above or below the melting point of the polymeric material, thereby forming an oxidation-resistant polymeric material; b) extracting or eluting the antioxidant from the surface regions of the oxidation-resistant consolidated polymeric material, thereby preventing or minimizing in vivo elution of the antioxidant; and c) irradiating the consolidated oxidation-resistant polymeric material with ionizing radiation, thereby forming an oxidation-resistant cross-linked consolidated polymeric material.

In another embodiment, the invention provides methods of making an oxidation-resistant cross-linked medical implant comprising: a) doping a consolidated polymeric material with an antioxidant, thereby forming an oxidation-resistant polymeric material; b) machining the consolidated and antioxidant-resistant polymeric material, thereby forming an oxidation-resistant medical implant; c) extracting or eluting the antioxidant from the surface regions of the oxidation-resistant medical implant, thereby preventing or minimizing in vivo elution of the antioxidant; and d) irradiating the oxidation-resistant to medical implant with ionizing radiation, thereby forming an oxidation-resistant cross-linked medical implant. The medical implant can be packaged and sterilized.

In another embodiment, the invention provides methods of making an oxidation-resistant cross-linked medical implant comprising: a) blending one or more types of resin, flakes, or powder with an antioxidant; b) consolidating the antioxidant-blended resin, flakes, or powder, thereby forming a medical implant preform; c) extracting or eluting the antioxidant from the surface regions of the oxidation-resistant medical implant preform, thereby preventing or minimizing in vivo elution of the antioxidant; d) irradiating the oxidation-resistant medical implant preform with ionizing radiation, thereby forming an oxidation-resistant cross-linked medical implant preform; and e) machining the oxidation-resistant cross-linked medical implant preform, thereby forming an oxidation-resistant cross-linked medical implant. The medical implant can be packaged and sterilized.

In another embodiment, the antioxidant-doped or -blended polymeric material is homogenized at a temperature below or above the melting point of the polymeric material for about an hour to several days.

In another embodiment of the invention, the oxidation-resistant cross-linked medical implant preform is further homogenized following the irradiation step by heating to a temperature below or above the melt to allow diffusion of the antioxidant from the antioxidant-rich to antioxidant-poor regions and oxidative stability throughout the medical implant.

According to one embodiment of the invention, the oxidation-resistant polymeric material or the medical implant is further doped with an antioxidant by diffusion at a temperature below or above the melting point of the irradiated polymeric material.

In another embodiment, the antioxidant-doped or -blended polymeric material is further homogenized at a temperature below or above the melting point of the polymeric material for about an hour to several days to several weeks.

In another embodiment, the antioxidant-doped or -blended polymeric material, the oxidation-resistant medical implant preform, or the medical implant preform is further homogenized at a temperature below or above the melting point of the polymeric material, before and/or after the irradiation step, for about an hour to several days to several weeks.

In another embodiment, the antioxidant-doped or -blended polymeric material is machined thereby creating a medical implant.

In another embodiment, the medical implant is packaged and sterilized by ionizing radiation or gas sterilization, thereby forming a sterile and cross-linked oxidation-resistant medical implant.

In some embodiments, the polymeric material is compression molded to another piece or a medical implant, thereby forming an interface or an interlocked hybrid material; or the antioxidant blended polymeric material is compression molded to another piece or a medical implant, thereby forming an interface or an interlocked hybrid material; or the consolidated antioxidant doped polymeric material is compression molded to another piece, thereby forming an interface and an interlocked hybrid material; or the consolidated polymeric material is compression molded to another piece, thereby forming an interface and an interlocked hybrid material.

In another embodiment, irradiated and melted material is compression molded onto the surface of the antioxidant-doped or -blended polymeric material or implant. In another embodiment, irradiated, mechanically deformed and thermally treated (above or below the melt) material is compression molded onto the surface of the anti-oxidant doped or blended polymeric material or implant. In another embodiment, irradiated and high pressure crystallized polymeric material is compression molded onto the surface of the antioxidant-doped or -blended polymeric material or implant.

In another embodiment, the invention provides an oxidation-resistant cross-linked polymeric material having a spatially controlled antioxidant distribution, wherein the polymeric material is obtainable by any of the methods described herein.

According to one aspect of the invention, the doping is carried out by soaking the medical implant in the antioxidant, preferably, for about half an hour to about 100 hours, more preferably, for about an hour, about 2, 3, 4, 5, 6, 7, 8, 9, 10, 11, 12, 13, 14, 15, or about 16 hours, and/or the antioxidant is heated to about 120° C. and the doping is carried out at about 120° C., and/or the antioxidant is warmed to about room temperature and the doping is carried out at room temperature or at a temperature between room temperature and the peak melting temperature of the polymeric material or less than about 137° C., and/or the cross-linked polymeric material is heated at a temperature below the melt or above the melt of the cross-linked polymeric material.

According to another aspect of the invention, the polymeric material is a polyolefin, a polypropylene, a polyamide, a polyether ketone, or a mixture thereof; wherein the polyolefin is selected from a group consisting of a low-density polyethylene, high-density polyethylene, linear low-density polyethylene, ultra-high molecular weight polyethylene (UHMWPE), or a mixture thereof; and wherein the polymeric material is polymeric resin powder, polymeric flakes, polymeric particles, or the like, or a mixture thereof or a consolidated resin.

According to another aspect of the invention, polymeric material is a hydrogel, such as poly (vinyl alcohol), poly (acrylamide), poly (acrylic acid), poly(ethylene glycol), blends thereof, or interpenetrating networks thereof, which can absorb water such that water constitutes at least 1 to 10,000% of their original weight, typically 100 wt % of their original weight or 99% or less of their weight after equilibration in water.

In another embodiment of the invention, the implant comprises medical devices selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, interpositional devices for any joint, sutures, tendons, heart valves, stents, vascular grafts.

In another embodiment of the invention, the medical implant is a non-permanent medical device, for example, a catheter, a balloon catheter, a tubing, an intravenous tubing, or a suture.

In another embodiment of the invention, the oxidation-resistant cross-linked medical implant preform is further homogenized following the irradiation step by heating to a temperature below or above the melt to allow diffusion of the antioxidant from the antioxidant-rich to antioxidant-poor regions and oxidative stability throughout the medical implant.

In another embodiment of the invention, the antioxidant-doped polymeric material, the oxidation-resistant medical implant preform, or the medical implant preform is homogenized before and/or after irradiation, by thermally annealing at a temperature above or below the melting point of the polymeric material.

In another embodiment of the invention, the cross-linked oxidation-resistant medical implant is packaged and sterilized by ionizing radiation or gas sterilization, thereby forming a sterile and oxidation-resistant cross-linked medical implant having a spatial distribution of antioxidant and/or cross-linking.

In another embodiment of the invention, the antioxidant is diffused to a depth of about 5 mm or more from the surface, for example, to a depth of about 3-5 mm, about 1-3 mm, or to any depth thereabout or therebetween.

In another embodiment, the invention provides an oxidation-resistant cross-linked polymeric material obtainable by any of the methods described herein.

BRIEF DESCRIPTION OF THE DRAWINGS

FIG. 11 shows the vitamin E concentration profile of a UHMWPE thin section to melt-doped at 170° C. for 22 hours and subsequently homogenized at 132° C. for 48 hours.

DETAILED DESCRIPTION OF THE INVENTION

Figure 1:
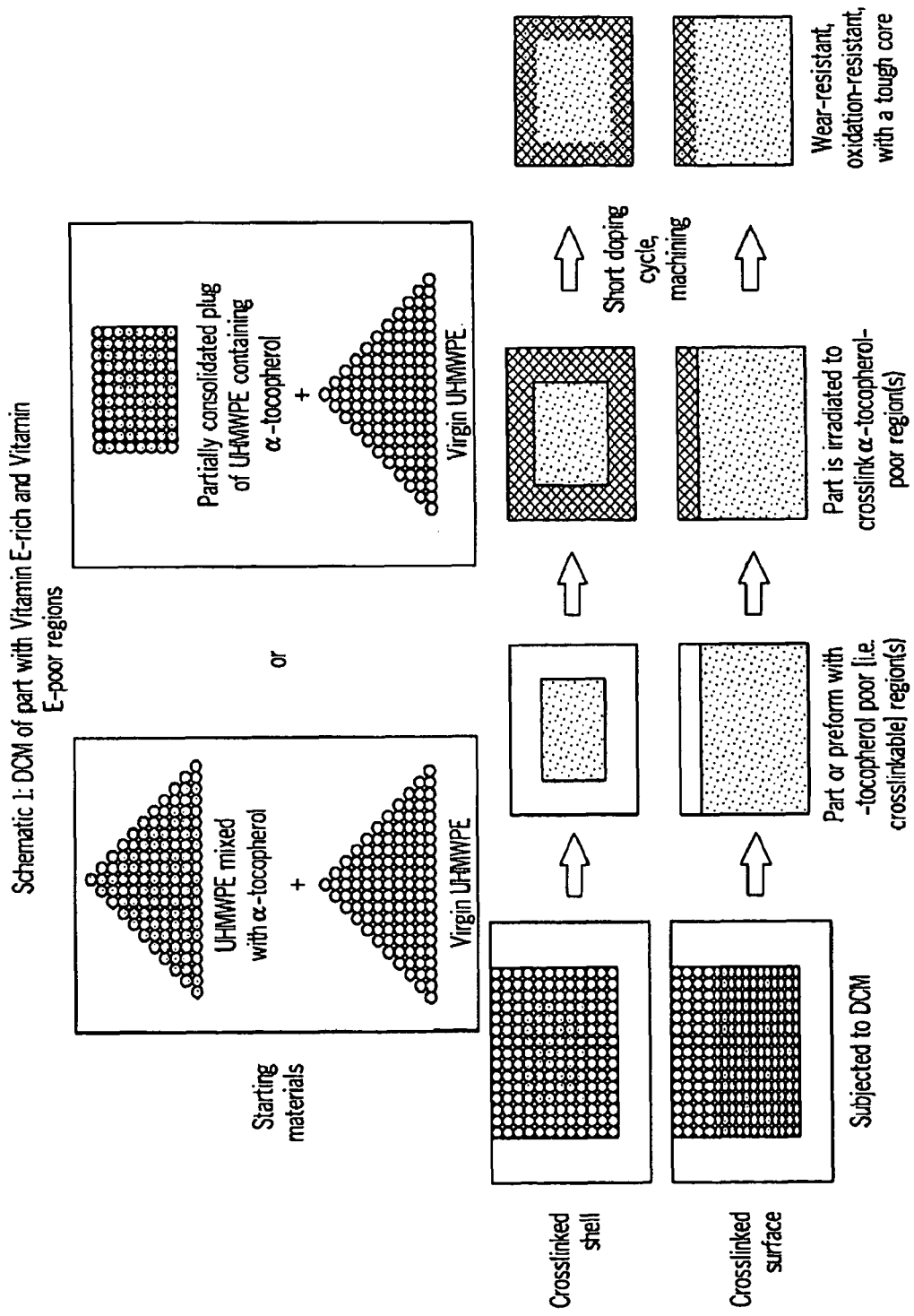
FIG. 1 shows schematic diagram of direct compression molding (DCM) of UHMWPE with Vitamin E rich and Vitamin E poor regions.

The present invention provides methods for making cross-linked oxidation-resistant polymeric materials and/or preventing or minimizing in vivo elution of antioxidant from the antioxidant-containing polymeric materials. The invention pertains to methods of doping consolidated polymeric materials, such as UHMWPE, with a spatial control of antioxidant distribution, for example, vitamin E, before, during, or after radiation cross-linking the polymeric materials, as well as materials made thereby. The invention also pertains to methods of extraction of antioxidants, for example, vitamin E (α-tocopherol), from antioxidant-containing consolidated polymeric materials, including cross-linked polymeric materials, as well as materials made thereby.

According to one aspect of the invention, the limitations of α-tocopherol diffusion in polymeric material are overcome by shortening the diffusion path of α-tocopherol necessary after irradiation. This is achieved by creating a polymeric article that has higher α-tocopherol concentration in the bulk (generally the interior regions) and lower α-tocopherol concentration on the surface (exterior regions). When this polymeric article is irradiated, the α-tocopherol-poor regions in the surface, in which wear reduction through cross-linking is necessary, can be as highly cross-linked as they would be in the absence of α-tocopherol. On the other hand, the surface contains either no α-tocopherol or lower concentrations of α-tocopherol. Therefore, the surface is cross-linked during irradiation and the wear rate is reduced. Cross-linking is only needed on and near the articular surfaces to improve the wear resistance of the implant. Although the surface and the bulk of a polymeric material generally refer to exterior regions and the interior regions, respectively, there generally is no discrete boundary between these two regions. The regions are more of a gradient-like transition, can differ based upon the size and shape of the object and the resin used.

Irradiation of UHMWPE with α-tocopherol reduces the cross-linking efficiency of polyethylene and also reduces the anti-oxidant potency of α-tocopherol. Therefore, in some embodiments, there is enough α-tocopherol in the bulk such that after the irradiation step(s) there is still enough antioxidant potency to prevent oxidation in the bulk of the polyethylene. Thus, after irradiation the polymeric article is oxidation-resistant in the bulk and is highly cross-linked on the surface. However the surface may contain unstabilized free radicals that can oxidize and reduce the mechanical properties of the article. To prevent oxidation on the α-tocopherol-poor surface region, the irradiated polymeric article can be treated by using one or more of the following methods:

(1) doping with an antioxidant through diffusion at an elevated temperature below or above the melting point of the irradiated polymeric material;

(2) melting of the article;

(3) mechanically deforming of the UHMWPE followed by heating below or above the melting point of the polymeric material; and (4) high pressure crystallization or high pressure annealing of the article;

After these treatments, the free radicals are stabilized in the article. Doping of α-tocopherol through diffusion at a temperature above the melting point of the irradiated polymeric material (for example, at a temperature above 137° C. for UHMWPE) can be carried out under sub-ambient pressure, ambient pressure, elevated pressure, and/or in a sealed chamber. Doping above the melting point can be done by soaking the article in vitamin E at a temperature above 137° C. for at least 10 seconds to about 100 hours or longer. At elevated pressures, the melting point of polymeric material can be elevated, therefore temperature ranges 'below' and 'above' the melting point may change under pressure.

In some embodiments none of the above mentioned four stabilization techniques are used because there is still enough antioxidant potency left in the polymeric material both at the surface and in the bulk so as not to compromise oxidation stability of the polymeric material in the long-term. For instance the polymeric material with spatially varying antioxidant concentration is irradiated at an elevated temperature above room temperature, preferably at about 40° C., at above 40° C., at 75° C., at above 75° C., at about 100° C., at about 110° C., or at about 120° C.

Another advantage of this approach where cross-linking is constrained to a thin surface layer is that the overall bulk mechanical properties of the polymeric article are not altered compared to unirradiated UHMWPE as they would be if the cross-links were uniformly distributed throughout the entire article.

Another added benefit of this invention is that the α-tocopherol doping can be carried out at elevated temperatures to shorten the diffusion time.

All of the embodiments are described with α-tocopherol as the antioxidant but any other antioxidant or mixtures of antioxidants also can be used.

According to one embodiment, the polymeric material is an article having a shape of an implant, a preform that can be machined to an implant shape, or any other shape.

In one embodiment, the polymeric article is prepared with α-tocopherol-rich and α-tocopherol-poor regions where the α-tocopherol-poor regions are located at one or more of the surface (exterior regions) and the α-tocopherol-rich regions are in the bulk (generally the interior regions).

An advantage of starting with α-tocopherol-rich and α-tocopherol-poor regions in the polymeric article is that the radiation cross-linking will primarily be limited to the α-tocopherol-poor regions (in most embodiments the articular surfaces) and therefore the reduction in the mechanical properties of the implant due to cross-linking will be minimized.

In another embodiment, the consolidated polymeric material is fabricated through direct compression molding (DCM). The DCM mold is filled with a combination of polyethylene powder containing α-tocopherol and with virgin polyethylene powder, that is without α-tocopherol (see schematic diagram in FIG. 1). The mold is then heated and to pressurized to complete the DCM process. The consolidated polymeric material thus formed consists of α-tocopherol rich and α-tocopherol-poor regions. The concentration of α-tocopherol in the initial α-tocopherol-containing powder may be sufficiently high to retain its antioxidant efficiency throughout the DCM process, and any subsequent irradiation and cleaning steps. This concentration is between about 0.0005 wt % and about 20 wt % or higher, preferably between 0.005 wt % and 5.0 wt %, preferably about 0.5 wt % or 1.0 wt %, preferably about 0.3 wt %, or preferably about 0.2 wt % or 0.1 wt %. The DCM mold is filled with either or both of the powders to tailor the spatial distribution of the α-tocopherol-rich and α-tocopherol-poor regions in the consolidated polymeric article. One issue is the diffusion of α-tocopherol from the blended powder regions to the virgin powder regions, especially during consolidation where high temperatures and durations are typical. Any such diffusion would reduce the efficiency of subsequent cross-linking in the affected virgin powder regions. One can control the diffusion process by precisely tailoring the spatial distribution of the α-tocopherol rich and α-tocopherol-poor regions, by optimizing the content of α-tocopherol in the blended regions, by reducing the temperature of consolidation, and/or reducing the time of consolidation.

In another embodiment, the consolidated polymeric material is fabricated through direct compression molding (DCM). The DCM mold is filled with a combination of polyethylene powder containing a high concentration of α-tocopherol and with polyethylene powder containing a low concentration of α-tocopherol (see schematic diagram in FIG. 32). The mold is then heated and pressurized to complete the DCM process. The consolidated polymeric material thus formed consists of α-tocopherol rich and α-tocopherol-poor regions. The concentration of α-tocopherol in the initial high α-tocopherol-containing powder region may be sufficiently high to retain its antioxidant efficiency throughout the DCM process, and any subsequent irradiation and cleaning steps. It can also be high enough to decrease crosslinking density after radiation compared to consolidated stock made from virgin UHMWPE. This concentration is between about 0.0005 wt % and about 20 wt % or higher, preferably between 0.005 wt % and 5.0 wt %, preferably about 0.5 wt % or 1.0 wt %, preferably about 0.3 wt %, or preferably about 0.2 wt % or 0.1 wt %. The concentration of α-tocopherol in the initial low α-tocopherol-containing powder region may be sufficiently high to retain its antioxidant efficiency throughout the DCM process, and any subsequent irradiation and cleaning steps. It can also be low enough not to change crosslinking density after radiation compared to consolidated stock made from virgin UHMWPE. This concentration is between about 0.0005 wt % and about 20 wt % or higher, preferably between 0.005 wt % and 5.0 wt %, preferably about 0.5 wt % or 1.0 wt %, preferably about 0.3 wt %, or preferably about 0.2 wt % or 0.1 wt %. The DCM mold is filled with either or both of the powders to tailor the spatial distribution of the α-tocopherol-rich and α-tocopherol-poor regions in the consolidated polymeric article. One issue is the diffusion of α-tocopherol from the blended powder regions containing high concentration of α-tocopherol to the blended powder regions containing low concentration of α-tocopherol, especially during consolidation where high temperatures and durations are typical. One can control the diffusion process by precisely tailoring the spatial distribution of the α-tocopherol-rich and α-tocopherol-poor regions, by optimizing the content of α-tocopherol in the blended regions, by reducing the temperature of consolidation, and/or reducing the time of consolidation or placing diffusion barrier in between the two regions such as a previously molded piece of UHMWPE, with or without antioxidant.

In some embodiments the α-tocopherol rich region is confined to the core of the polymeric article and the virgin polymer is confined to the outer shell whereby the thickness of the α-tocopherol-poor region is between about 0.01 mm and 20 mm, more preferably between about 1 mm and 5 mm, or more preferably about 3 mm.

In some embodiments the outer layer is limited to only one or more faces of the polymeric article. For example a polymeric article is made through DCM process by compression molding two layers of polyethylene powder, one containing 0.3 or 0.5 wt % α-tocopherol and one virgin with no α-tocopherol or containing a low concentration of α-tocopherol such as 0.02 or 0.05 wt %. The order in which the two powders are placed into the mold determines which faces of the polymeric article are α-tocopherol-poor and the thickness of the α-tocopherol-poor region is determined by the amount of virgin powder used. Alternatively, the thickness of the α-tocopherol-poor region is determined after consolidation or after any of the subsequent steps by machining away sample from the surface. This polymeric article is subsequently irradiated, doped with α-tocopherol, homogenized, machined on one or more of the faces to shape a polymeric implant, packaged and sterilized.

In some embodiments, the α-tocopherol-rich region is molded from a blend of α-tocopherol-containing powder and virgin polyethylene powder or a α-tocopherol-containing powder with a low concentration of α-tocopherol.

In some embodiments, the powder containing α-tocopherol and the virgin polyethylene powder or α-tocopherol-containing powder with a low concentration of α-tocopherol are dry-mixed prior to molding, thereby creating a distribution of α-tocopherol-rich and α-tocopherol-poor regions throughout the polyethylene article.

In some embodiments, the virgin polyethylene region is confined to the articular bearing surface of the implant.

In some embodiments, the powder containing α-tocopherol undergoes partial or complete consolidation prior to the DCM process (see FIG. 1). This preformed piece of α-tocopherol-containing polyethylene allows more precise control over the spatial distribution of α-tocopherol in the finished part. For example, the partially or completely consolidated powder is placed in a mold surrounded by virgin powder or α-tocopherol-containing powder with a low concentration of α-tocopherol and further consolidated, creating a polyethylene article with an α-tocopherol-poor region on the outer shell and α-tocopherol-rich region in the bulk of the polyethylene article.

In another embodiment a polyethylene component is fabricated through DCM as described above with spatially-controlled α-tocopherol-rich and α-tocopherol-poor regions. This component is subsequently treated by e-beam irradiation. E-beam irradiation is known to have a gradient cross-linking effect in the direction of the irradiation, but this is not always optimized in components which have curved surfaces, such as acetabular cups, where the cross-linking will be different at different points on the articulating surface. The spatial distribution of α-tocopherol-rich regions is used in conjunction with e-beam irradiation to create uniform surface cross-linking which gradually decreases to minimal cross-linking in the bulk. After irradiation, the polyethylene component is doped with α-tocopherol. This component is cross-linked and stabilized at the surface and transitions to the uncross-linked and stabilized material with increasing depth from the surface.

In some embodiments the vitamin-E/polyethylene blended powder mixture has a very high vitamin-E concentration such that when this powder mixture is consolidated with neat powder there is a steep gradient of vitamin-E across the interface. The consolidated piece is then irradiated to cross-link the polymer preferably in the neat α-tocopherol-poor region. Subsequently, the piece is heated to drive diffusion of α-tocopherol from the α-tocopherol-rich bulk region to the α-tocopherol-poor surface region.

In some embodiments, a vitamin-E-polyethylene (for example, UHMWPE) blend and virgin polyethylene resin powder or α-tocopherol-containing powder with a low concentration of α-tocopherol are molded together to create an interface. The quantities of the high concentration blend and/or the low concentration blend or virgin resins are tailored to obtain a desired α-tocopherol-poor polyethylene thickness. Alternatively, the molded piece/material is machined to obtain the desired thickness of the virgin polyethylene layer. The machined-molded piece/material is irradiated followed by:

Either doping with vitamin E and homogenized below the melting point or above the melting point of the polyethylene, or heated above the melt without doping to eliminate the free radicals (for example, for different durations), or heated above the melt for long enough duration, which will also diffuse the bulk vitamin E from the vitamin E-rich blend layer into the vitamin E-poor layer (for example, for different durations, different blend compositions are used to accelerate the diffusion from the rich region to the poor region), or high pressure crystallized/annealed, thereby forming a medical implant. The medical implant can be used at this stage or can be machined further to remove any oxidized surface layers to obtain a net shaped implant. The implant also can be packaged and sterilized.

In another embodiment, the antioxidant-doped or -blended polymeric material is homogenized at a temperature below or above the melting point of the polymeric material for a desired period of time, for example, the antioxidant-doped or -blended polymeric material is homogenized for about an hour to several days to one week or more than one week at room temperature to about 400° C. Preferably, the homogenization is carried out above room temperature, preferably at about 90° C. to about 180° C., more preferably about 100° C. to about 137° C., more preferably about 120° C. to about 135° C., most preferably about 130° C.

A purpose of homogenization is to make the concentration profile of α-tocopherol throughout the interior of a consolidated polymeric material more spatially uniform. After doping of the polymeric material is completed, the consolidated polymeric material is removed from the bath of α-tocopherol and wiped thoroughly to remove excess α-tocopherol from the surfaces of the polymeric material. The polymeric material is kept in an inert atmosphere (nitrogen, argon, and/or the like) or in air during the homogenization process. The homogenization also can be preformed in a chamber with supercritical fluids such as carbon dioxide or the like.

Figure 2:
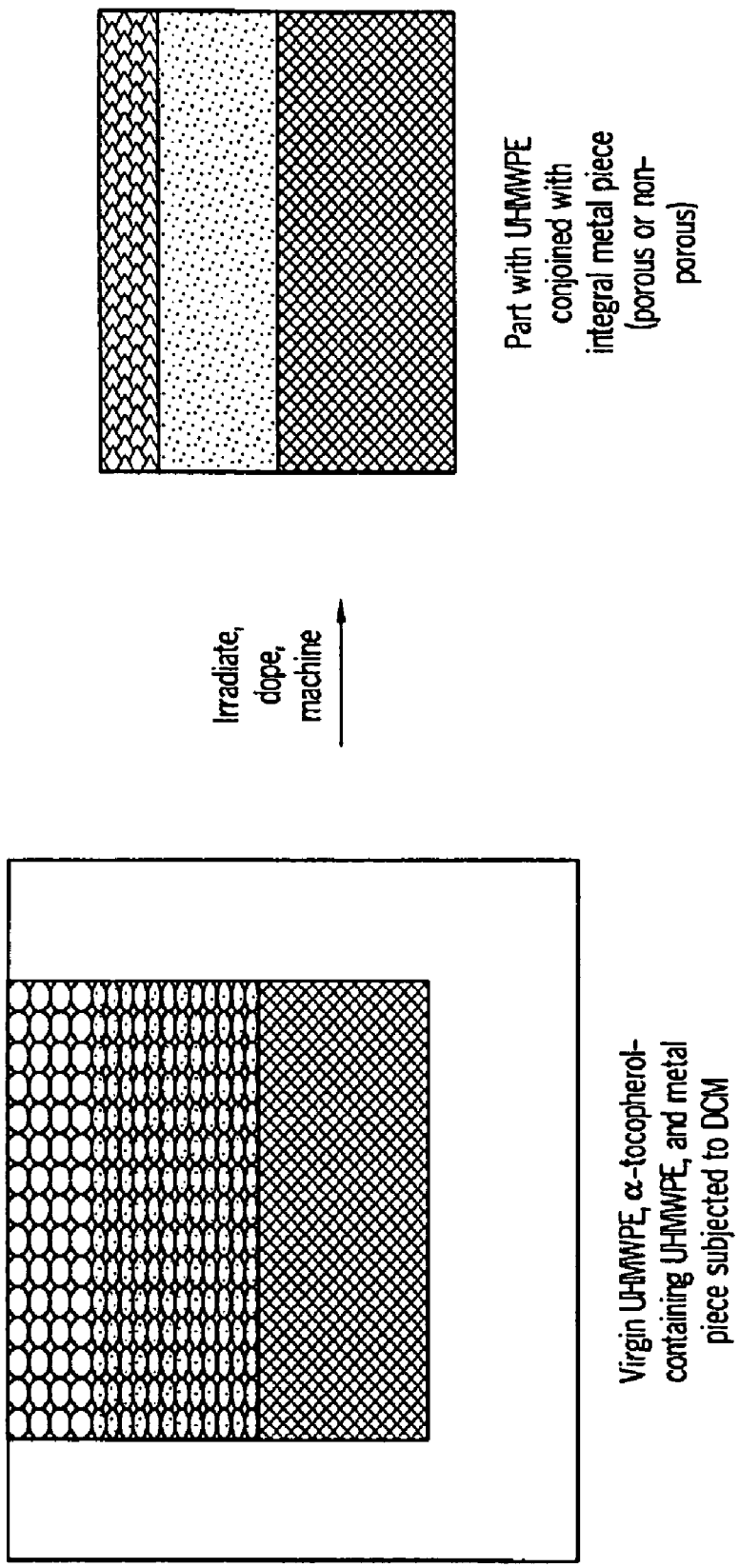
FIG. 2 shows schematic diagram of DCM of UHMWPE containing integral metal piece.

In another embodiment, the DCM process is conducted with a metal piece that becomes an integral part of the consolidated polyethylene article (see schematic diagram in FIG. 2). For example, a combination of α-tocopherol-containing polyethylene powder and virgin polyethylene powder is direct compression molded into a metallic acetabular cup or a tibial base plate with a spatially controlled distribution of α-tocopherol-rich and α-tocopherol-poor regions so that cross-linking of the polyethylene during the subsequent irradiation step is not hindered at the articular surfaces. For example, the porous tibial metal base plate is placed in the mold, α-tocopherol blended polyethylene powder is added on top and then virgin polyethylene powder is added last. Following consolidation the article is α-tocopherol-rich near the metal piece and also in the bulk but the articular surface is α-tocopherol-poor, which allows cross-linking of the surface layer during subsequent irradiation. Doping of the article with α-tocopherol is carried out after irradiation to stabilize the free radicals near the articular surface. Prior to the DCM consolidation the pores of the metal piece can be filled with a waxy substance through half the thickness to achieve polyethylene interlocking through the other unfilled half of the metallic piece. The pore filler is maintained through the irradiation and subsequent α-tocopherol doping steps to prevent infusion of α-tocopherol in to the pores of the metal. In some embodiments, the article is machined after doping to shape an implant.

Elution of vitamin E from irradiated and vitamin E doped/containing UHMWPE parts is observed during shelf storage at 40° C. or storage in water at 40° C. The latter simulated an in vivo environment and extraction of vitamin E from these parts in this simulated in vivo environment raised concerns as to the potential local tissue response to the exuding vitamin E and also as to the long-term oxidative stability of the implant when enough vitamin E is exuded out. Therefore, some experiments that are devised first also are disclosed herein, to determine the oxidative stability of irradiated and vitamin E doped/containing UHMWPE parts after forceful extraction/elution of vitamin E, for example, by soaking in boiling hexane for 72 hours; and second, developed methods to extract vitamin E from the irradiated and vitamin E doped/containing UHMWPE parts to prevent in vivo elution of the vitamin E.

The elution of α-tocopherol from an implanted device can potentially effect the surrounding tissues and joint spaces. Therefore, it is beneficial to extract the excess and elutable α-tocopherol from the surface region of antioxidant containing polymeric materials prior to placement and/or implantation to minimize the elution of α-tocopherol in vivo. The present invention provides several approaches as to how this can be achieved and provides methods of extraction of α-tocopherol from the surface region of antioxidant containing polymeric materials. The present invention also provides an example where all of the detectable α-tocopherol is extracted from an irradiated and α-tocopherol doped UHMWPE, which continued to be stable against oxidation even after the extraction, based on two weeks aging in oxygen at 5 atm at 70° C. (ASTM F2003-02). Therefore, removal of the excess or at least partial removal of the α-tocopherol can be used to minimize the in vivo elution of the α-tocopherol from irradiated and α-tocopherol-doped/containing UHMWPE parts.

In most of the embodiments, α-tocopherol is described as an antioxidant; however, any other antioxidants known in the art or a mixture thereof also can be used.

In an embodiment, the polymeric material, for example, UHMWPE, is used as an article having a shape of a medical implant, an implant preform that can be machined to an implant shape or any other desirable shape.

In an embodiment, the polymeric article is prepared with a gradient of α-tocopherol concentration (by elution, for example) where the surface (exterior regions) has less α-tocopherol than the bulk (interior regions).

Figure 14:
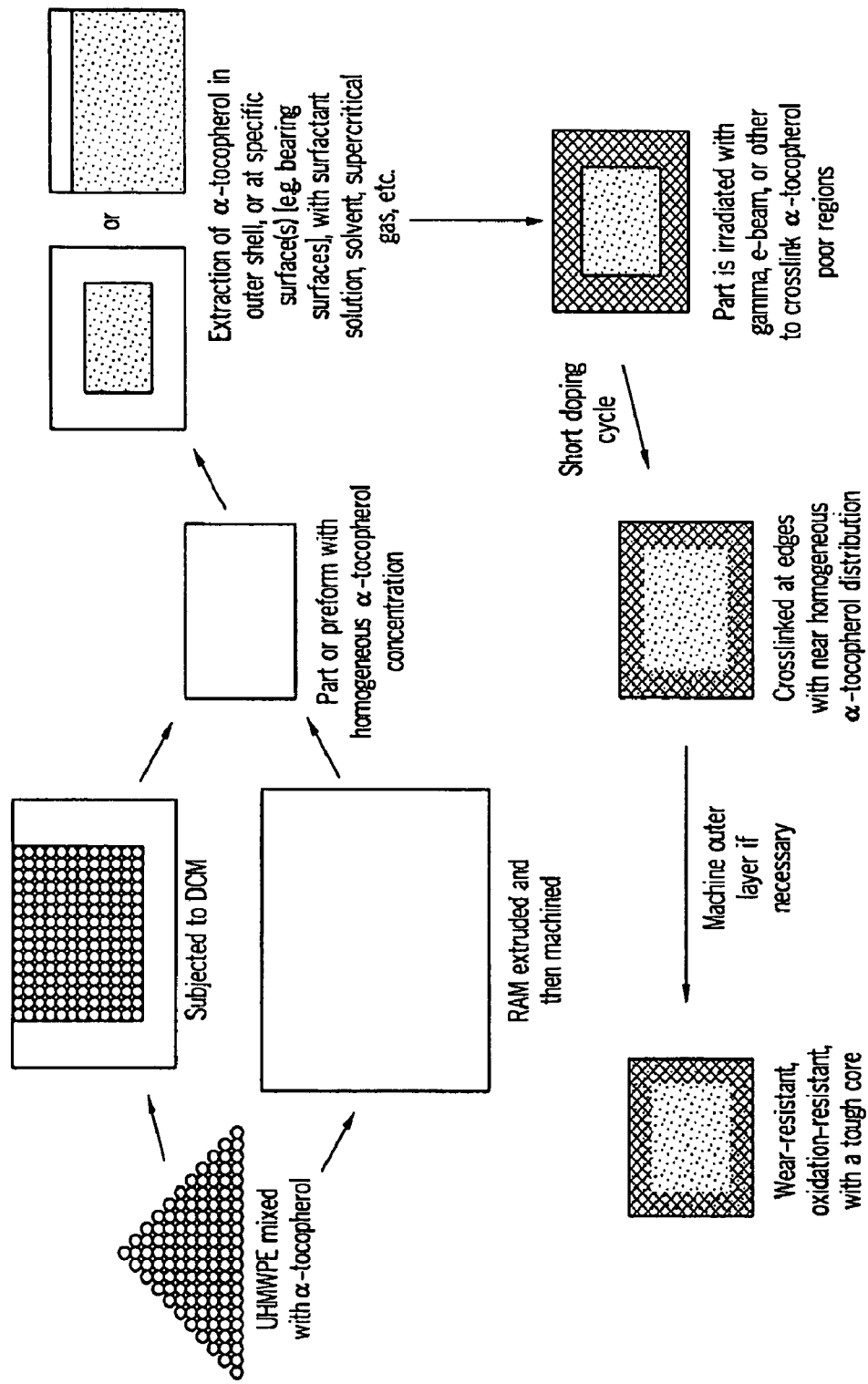
FIG. 14 shows schematic diagram of extraction of α-tocopherol from a doped UHMWPE.

In an embodiment, consolidated polymeric material with a gradient of α-tocopherol is prepared by the following method as illustrated in schematically (see FIG. 14): Consolidated polymeric material is formed by consolidating UHMWPE powder-α-tocopherol blend. The consolidation can be achieved through standard consolidation techniques such as ram extrusion, compression molding, or direct compression molding at elevated temperature and pressure, or other known approaches. Subsequently, the consolidated polyethylene article is extracted to remove the excess α-tocopherol or at least partially the α-tocopherol from the surface regions. The extraction can be carried out by placing the polyethylene in an alcohol, such as isopropyl alcohol (IPA), ethanol, or an aqueous solution of alcohol, in water, in water containing a surfactant such as tween-80, in an organic solvent such as xylene, hexane, toluene, or other, or a mixture thereof. The extraction also can be performed in supercritical fluids, such as water, $CO_2$, ethane, propane, other gases, or mixtures thereof.

The extraction can be carried out at room temperature or at elevated temperatures below or above the melting point of the polymeric material. At temperatures above the boiling point of the solvent or solvent mixtures used, pressure can be applied to achieve the desired temperature.

In another embodiment, a polyethylene article is doped or doped and homogenized with α-tocopherol and subsequently subjected to an extraction step to remove the excess α-tocopherol or at least a portion of the α-tocopherol from the surface regions.

Another advantage of starting with a gradient of α-tocopherol concentration in the polyethylene article is that the radiation cross-linking is primarily occurs in the α-tocopherol deficient regions (in most embodiments the articular surfaces) and therefore, the reduction in the mechanical properties of the implant due to cross-linking is minimized.

In another embodiment, an implant or a preform is made out of α-tocopherol and UHMWPE powder blend either by machining a large consolidate made from the powder blend or by direct compression molding the powder blend. The implant or preform is then placed in a solvent or solvent mixture or in a gas or gas mixture or in a supercritical fluid or fluid mixture to extract the α-tocopherol from near the outside surfaces. It is beneficial to have reduced the α-tocopherol concentration within 1 micrometer of the surface up to several millimeters or beyond. The implant or preform is then irradiated. The surface (exterior regions), which is depleted of α-tocopherol to a certain extent, will have a higher cross-link density than the bulk (interior regions). Following irradiation, the surface may not have enough α-tocopherol left because of the surface depletion step is performed prior to the irradiation. Therefore doping the implant after irradiation may be necessary to stabilize the free radicals, especially near the surface.

In another embodiment, the polyethylene article is fabricated through direct compression molding (DCM). The DCM mold is filled with polyethylene powder containing α-tocopherol. The mold is then heated and pressurized to complete the DCM process. The polyethylene article thus formed consists of α-tocopherol containing regions. The concentration of α-tocopherol in the α-tocopherol-containing powder may be sufficiently high to retain its antioxidant efficiency throughout the DCM process, and any subsequent irradiation, extraction and cleaning steps. This concentration is between about 0.0005 wt % and about 20 wt % or higher, preferably between 0.005 wt % and 5.0 wt %, preferably about 0.3 wt %, or preferably about 0.5 wt %. The DCM mold is filled with the UHMWPE powder to blend in α-tocopherol in the consolidated polyethylene article.

This polyethylene article is subsequently irradiated, doped with α-tocopherol, homogenized, subjected to an extraction step to remove the excess α-tocopherol or at least a portion of the α-tocopherol from the surface region(s), machined on one or more of the faces to shape a polyethylene implant, cleaned, packaged and sterilized.

This polyethylene article is subsequently irradiated, doped with α-tocopherol, homogenized, machined on one or more of the faces to shape a polyethylene implant subjected to an extraction step to remove the excess α-tocopherol or at least a portion of the α-tocopherol from the surface region(s), cleaned, packaged and sterilized.

In some embodiments, a vitamin-E-polyethylene (for example, UHMWPE) blend is molded together to create an interface. The machined-molded piece/material is then subjected to an extraction step, to remove the excess α-tocopherol or at least a portion of the α-tocopherol from the surface regions, and irradiated followed by:

Either doping with vitamin E and homogenized below the melting point or above the melting point of the polyethylene, or doping with vitamin E and homogenized below the melting point or above the melting point of the polyethylene, then subjected to an extraction step to remove the excess α-tocopherol or at least a portion of the α-tocopherol from the surface regions, or heated above the melt without doping to eliminate the free radicals (for example, for different durations), or heated above the melting temperature for long enough duration to form a homogeneous blend, thereby forming a medical implant. The medical implant can be used at this stage or can be machined further to remove any oxidized surface layers to obtain a net shaped implant. The implant also can be packaged and sterilized.

In another embodiment, the antioxidant-doped or -blended polymeric material is homogenized at a temperature below or above the melting point of the polymeric material for a desired period of time, for example, the antioxidant-doped or -blended polymeric material is homogenized for about an hour to several days (1 to 28 days), preferably for 24 hours. After doping/blending of polyethylene with α-tocopherol, the homogenization step is employed. A purpose of homogenization is to make the concentration profile of α-tocopherol throughout the interior of the polyethylene sample more spatially uniform. After doping is completed, the polyethylene is removed from the bath of α-tocopherol and wiped thoroughly to remove excess α-tocopherol from the surfaces of the polyethylene. The polyethylene is then homogenized at a temperature between room temperature and about 400° C. Preferably, the homogenization is carried out above room temperature, preferably at about 90° C. to about 180° C., more preferably about 100° C. to about 137° C., more preferably about 120° C. to about 135° C., most preferably about 130° C. The polyethylene is kept in an inert atmosphere (nitrogen, argon, and/or the like) or in air during the homogenization process. The homogenization also can be performed in a chamber with supercritical fluids such as carbon dioxide or the like.

In another embodiment, there are more than one metal pieces integral to the polyethylene article.

In another embodiment, one or some or all of the metal pieces integral to the polyethylene article is a porous metal piece that allows bone in-growth when implanted into the human body.

In some embodiments, one or some or all of the metal pieces integral to the polyethylene article is a non-porous metal piece.

In one embodiment, the consolidated polyethylene article is irradiated using ionizing radiation such as gamma, electron-beam, or x-ray to a dose level between about 1 and about 10,000 kGy, preferably about 25 to about 250 kGy, preferably about 50 to about 150 kGy, preferably about 65 kGy, preferably about 85 kGy, or preferably about 100 kGy.

In another embodiment, the irradiated polyethylene article is doped with α-tocopherol by placing the article in an α-tocopherol bath at room temperature or at an elevated temperature for a given amount of time.

In another embodiment, the doped polyethylene article is heated above or below the melting point of the polyethylene.

In another embodiment, the doped polyethylene article is heated above or below the melting point of the polyethylene under pressure. Pressure can be applied in water, any fluid, an inert gas, a non-inert gas, or a supercritical fluid. Pressure also can be applied mechanically.

In one embodiment, the metal mesh of the implant is sealed using a sealant to prevent or reduce the infusion of α-tocopherol into the pores of the mesh during the selective doping of the implant. Preferably the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch.

In another embodiment, the polyethylene-porous metal mono-block is doped so that the polyethylene is fully immersed in α-tocopherol but the porous metal is either completely above the α-tocopherol surface or only partially immersed during doping. This reduces infusion of α-tocopherol into the pores of the metal mesh.

In yet another embodiment, the doped polyethylene article is machined to form a medical implant. In some embodiments, the machining is carried out on sides with no metallic piece if at least one is present.

In most embodiments, the medical devices are packaged and sterilized.

In another aspect of the invention, the medical device is cleaned before packaging and sterilization.

In other embodiments, the antioxidant, for example, vitamin E, concentration profiles in implant components can be controlled in several different ways, following various processing steps in different orders, for example:

I. Blending the antioxidant and polyethylene resin, powder, or flakes, consolidating the blend, machining of implants, radiation cross-linking (at a temperature above or below the melting point of the polymeric material), and doping with the antioxidant;

II. Blending the antioxidant and polyethylene resin, powder, or flakes, consolidating the blend, machining of implants, radiation cross-linking (at a temperature above or below the melting point of the polymeric material), doping with the antioxidant and homogenizing;

III. Blending the antioxidant and polyethylene resin, powder, or flakes, consolidating the blend, machining of implants, radiation cross-linking (at a temperature above or below the melting point of the polymeric material), doping with the antioxidant and homogenizing, extracting/eluting out the excess antioxidant or at least a portion of the antioxidant;

IV. Blending the antioxidant and polyethylene resin, powder, or flakes, consolidating the blend, machining of preforms, radiation cross-linking (at a temperature above or below the melting point of the polymeric material), doping with the antioxidant, machining of implants;

V. Blending the antioxidant and polyethylene resin, powder, or flakes, consolidating the blend, machining of preforms, radiation cross-linking (at a temperature above or below the melting point of the polymeric material), doping with the antioxidant and homogenizing, machining of implants;

VI. Blending the antioxidant and polyethylene resin, powder, or flakes, consolidating the blend, machining of preforms, radiation cross-linking (at a temperature above or below the melting point of the polymeric material), doping with the antioxidant and homogenizing, machining of implants, extraction of the antioxidant;

VII. Radiation cross-linking of consolidated polymeric material (at a temperature above or below the melting point of the polymeric material), machining implant, doping with the antioxidant, extracting/eluting out the excess antioxidant or at least a portion of the antioxidant;

VIII. Radiation cross-linking of consolidated polymeric material (at a temperature above or below the melting point of the polymeric material), machining implants, doping with the antioxidant and homogenizing, extracting/eluting out the excess antioxidant or at least a portion of the antioxidant;

IX. Radiation cross-linking of consolidated polymeric material (at a temperature to above or below the melting point of the polymeric material), machining preforms, doping with the antioxidant, extraction of the antioxidant, machining of implants;

X. Radiation cross-linking of consolidated polymeric material (at a temperature above or below the melting point of the polymeric material), machining preforms, doping with the antioxidant and homogenizing, extracting/eluting out the excess antioxidant or at least a portion of the antioxidant, machining of implants;

XI. Radiation cross-linking of consolidated polymeric material (at a temperature above or below the melting point of the polymeric material), machining preforms, doping with the antioxidant, machining of implants, extracting/eluting out the excess antioxidant or at least a portion of the antioxidant; and/or XII. Radiation cross-linking of consolidated polymeric material (at a temperature above or below the melting point of the polymeric material), machining preforms, doping with the antioxidant and homogenizing, machining of implants, homogenizing, extracting/eluting out the excess antioxidant or at least a portion of the antioxidant.

In another embodiment, all of the above processes are further followed by cleaning, packaging and sterilization (gamma irradiation, e-beam irradiation, ethylene oxide or gas plasma sterilization).

According to another embodiment, in all of the above steps, the extraction can be done with a compatible solvent that dissolves the antioxidant. Such solvents include a hydrophobic solvent, such as hexane, heptane, or a longer chain alkane; an alcohol such as ethanol, any member of the propanol or butanol family or a longer chain alcohol; or an aqueous solution in which the antioxidant is soluble. Such solvents also can be made by using an emulsifying agent, such as Tween 80 or ethanol.

In some embodiments, antioxidant is extracted/eluted from an antioxidant-doped/containing consolidated polymeric material by contacting the consolidated polymeric material with a solvent in which the antioxidant is soluble or at least partially soluble.

High pressure crystallization is generally referred to as all of the methods of allowing the formation of extended chain crystals in the hexagonal phase. This transformation can be used alone or in combination with any of the methods described above. A method used for high pressure crystallization is by heating to a temperature above the melting point of the polyethylene at ambient pressure, then pressurizing so that the sample is in the melt during the pressurization until the conditions are met for the melt-to-hexagonal transformation to occur. Also, stepwise heating and pressurization can be performed such that the sample is not always in the melt until close to the hexagonal phase. The sample heating and pressurization can be done in a variety of manners such that when the hexagonal phase transformation occurs, the UHMWPE does not have a substantial amount of crystals and is considered in the melt phase.

Once the conditions are met for the hexagonal phase to be achieved and the extended chain crystals are formed, the sample cannot be allowed to completely melt because the desired crystalline structure would be lost. Therefore, any cooling and depressurization scheme allowing the sample to stay in the hexagonal or orthorhombic regions could be used. For example, a sample high pressure crystallized at about 200° C. and 380 MPa (55,000 psi) can be cooled down to approximately below the melting point of polyethylene at room temperature (about 135-140° C.), then the pressure can be released. Also, a stepwise cooling and depressurization method can be used as long as the sample does not melt substantially.

The ratio of folded to extended crystals may be dependent on the time spent in the hexagonal phase and whether or not the sample has melted. If a sample is fully crystallized in the hexagonal phase, is cooled down and/or depressurized to a pressure such that it encounters the melt phase partially or completely, and solely decreasing the temperature at the new pressure would not cause the sample to be in the hexagonal phase, then some or all of the crystals would be converted to folded chain crystals when the sample is further cooled down and depressurized.

1. High pressure crystallization of polyethylene can be achieved through the melt-phase (high pressure crystallization) or through the solid phase (high pressure annealing):
   A. High pressure crystallization (Route I): Heat to the desired temperature, for example, above the melt (for example, about 140° C., about 160° C., about 180° C., about 200° C., about 250° C., or about 300° C.); then pressurize; then hold pressure at about the same pressure, for one minute to a day or more, preferably about 0.5 hours to 12 hours, more preferably 1 to 6 hours; then release the pressure (pressure has to be released after cooling down to below the melting point of the polymeric material to avoid melting of the crystals achieved under high pressure).
   B. High pressure annealing (Route II): Pressurize to the desired pressure; then heat to the desired temperature, for example, below the melt of pressurized polyethylene (for example, about 150° C., about 160° C., about 180° C., about 195° C., about 225° C., about 300° C., and about 320° C.); then hold pressure at about the same pressure, for one minute to a day or more, preferably about 0.5 hours to 12 hours, more preferably 1 to 6 hours; then cool to room temperature; then release the pressure (pressure has to be released after cooling down to below the melting point of the polymeric material to avoid melting of the crystals achieved under high pressure).

Methods and Sequence of Irradiation:

The selective, controlled manipulation of polymers and polymer alloys using radiation chemistry can, in another aspect, be achieved by the selection of the method by which the polymer is irradiated. The particular method of irradiation employed, either alone or in combination with other aspects of the invention, such as the polymer or polymer alloy chosen, contribute to the overall properties of the irradiated polymer.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

According to certain embodiments, the cross-linked polymeric material can have a melt history, meaning that the polymeric material is melted concurrently with or subsequent to irradiation for cross-linking. According to other embodiments, the cross-linked polymeric material has no such melt history.

Various irradiation methods including IMS, CIR, CISM, WIR, and WIAM are defined and described in greater detail below for cross-linked polymeric materials with a melt history, that is irradiated with concurrent or subsequent melting:

(i) Irradiation in the Molten State (IMS):

Melt-irradiation (MIR), or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours. For UHMWPE, the polymer may be heated to a temperature between about 145° C. and about 230° C., preferably about 150° C. to about 200° C.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm.sup.3, which leads to the penetration of about 1 cm with a beam energy of 2-3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

The temperature of melt-irradiation for a given polymer depends on the DSC (measured at a heating rate of 10° C./min during the first heating cycle) peak melting temperature ("PMT") for that polymer. In general, the irradiation temperature in the IMS process is at least about 2° C. higher than the PMT, more preferably between about 2° C. and about 20° C. higher than the PMT, and most preferably between about 5° C. and about 10° C. higher than the PMT.

The total dose of irradiation also may be selected as a parameter in controlling the properties of the irradiated polymer. In particular, the dose of irradiation can be varied to control the degree of cross-linking and crystallinity in the irradiated polymer. The total dose may range from about 0.1 Mrad to as high as the irradiation level where the changes in the polymer characteristics induced by the irradiation reach a saturation point. For instance the high end of the dose range could be 20 Mrad for the melt-irradiation of UHMWPE, above which dose level the cross-link density and crystallinity are not appreciably affected with any additional dose. The preferred dose level depends on the desired properties that will be achieved following irradiation. Additionally, the level of crystallinity in polyethylene is a strong function of radiation dose level. See Dijkstra et al., Polymer 30: 866-73 (1989). For instance with IMS irradiation, a dose level of about 20 Mrad would decrease the crystallinity level of UHMWPE from about 55% to about 30%. This decrease in crystallinity may be desirable in that it also leads to a decrease in the elastic modulus of the polymer and consequently a decrease in the contact stress when a medical prosthesis made out of the IMS-treated UHMWPE gets in contact with another surface during in vivo use. Lower contact stresses are preferred to avoid failure of the polymer through, for instance, subsurface cracking, delamination, fatigue, etc. The increase in the cross-link density is also desirable in that it leads to an increase in the wear resistance of the polymer, which in turn reduces the wear of the medical prostheses made out of the cross-linked polymer and substantially reduces the amount of wear debris formed in vivo during articulation against a counterface. In general, the melt-irradiation and subsequent cooling will lead to a decrease in the crystallinity of the irradiated polymer.

Exemplary ranges of acceptable total dosages are disclosed in greater detail in U.S. Pat. No. 5,879,400 and International Application WO 97/29793. For example, preferably a total dose of about or greater than 1 MRad is used. More preferably, a total dose of greater than about 20 Mrad is used.

In electron beam IMS, the energy deposited by the electrons is converted to heat. This primarily depends on how well the sample is thermally insulated during the irradiation. With good thermal insulation, most of the heat generated is not lost to the surroundings and leads to the adiabatic heating of the polymer to a higher temperature than the irradiation temperature. The heating could also be induced by using a high enough dose rate to minimize the heat loss to the surroundings. In some circumstance, heating may be detrimental to the sample that is being irradiated. Gaseous by-products, such as hydrogen gas when PE is irradiated, are formed during the irradiation. During irradiation, if the heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the temperature rise can be controlled by determining an upper dose rate for the irradiation. For instance for the IMS of UHMWPE the dose rate should be less than about 5 Mrad/pass (only applicable for the e-beam and not gamma as gamma is inherently a low dose rate process). These considerations for optimization for a given polymer of a given size are readily determined by the person of skill in view of the teachings contained herein.

In embodiments of the present invention in which electron radiation is utilized, the energy of the electrons can be varied to alter the depth of penetration of the electrons, thereby controlling the degree of cross-linking and crystallinity following irradiation. The range of suitable electron energies is disclosed in greater detail in International Application WO 97/29793. In one embodiment, the energy is about 0.5 MeV to about 12 MeV. In another embodiment the energy is about 1 MeV to 10 MeV. In another embodiment, the energy is about 10 MeV.

(ii) Cold Irradiation (CIR):

Cold irradiation is described in detail in WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough to total dose and/or at a fast enough dose rate to generate enough heat in the polymer to result in at least a partial melting of the crystals of the polymer.

Gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels.

The total dose of irradiation may be selected as a parameter in controlling the properties of the irradiated polymer. In particular, the dose of irradiation can be varied to control the degree of cross-linking and crystallinity in the irradiated polymer. The preferred dose level depends on the molecular weight of the polymer and the desired properties that will be achieved following irradiation. For instance, to achieve maximum improvement in wear resistance using UHMWPE and the WIAM (warm irradiation and adiabatic melting) or CISM (cold irradiation and subsequent melting) processes, a radiation dose of about 10 Mrad is suggested. To achieve maximum improvement in wear resistance using LDPE and LLDPE, a dose level greater than about 10 Mrad is suggested. In general, increasing the dose level with CIR would lead to an increase in wear resistance. If the CIR is carried out without further post-irradiation melting, the crystallinity and elastic modulus of the polymer would increase. Following melting, however, these would decrease to values lower than those prior to irradiation.

Exemplary ranges of acceptable total dosages are disclosed in greater detail in International Application WO 97/29793. In the embodiments below, UHMWPE is used as the starting polymer. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially cross-linked with gradient in cross-link density as a function of distance away from the surface.

(iii) Warm Irradiation (WIR):

Warm irradiation is described in detail in WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM." In a theoretical sense, adiabatic heating means an absence of heat transfer to the surroundings. In a practical sense, such heating can be achieved by the combination of insulation, irradiation dose rates and irradiation time periods, as disclosed herein and in the documents cited herein. However, there are situations where irradiation causes heating, but there is still a loss of energy to the surroundings. Also, not all warm irradiation refers to an adiabatic heating. Warm irradiation also can have non-adiabatic or partially (such as about 10-75% of the heat generated is lost to the surroundings) adiabatic heating. In all embodiments of WIR, the polymer may be irradiated at a high enough total dose and/or a high enough dose rate to generate enough heat in the polymer to result in at least a partial melting of the crystals of the polymer.

The polymer may be provided at any temperature below its melting point but preferably above room temperature. The temperature selection depends on the specific heat and the enthalpy of melting of the polymer and the total dose level that will be used. The equation provided in International Application WO 97/29793 may be used to calculate the preferred temperature range with the criterion that the final temperature of polymer maybe below or above the melting point. Preheating of the polymer to the desired temperature, for example, about 50° C., about 60° C., about 70° C., about 80° C., about 85° C., about 90° C., about 95° C., about 105° C., about 110° C., about 115° C., or about 125° C., may be done in an inert or non-inert environment.

Exemplary ranges of acceptable total dosages are disclosed in greater detail in International Application WO 97/29793. In one embodiment, the UHMWPE is preheated to about room temperature (about 25° C.) to about 135° C. In one embodiment of WIAM, the UHMWPE is preheated to about 100° C. to just below the melting temperature of the polymer. In another embodiment of WIAM, the UHMWPE is preheated to a temperature of about 100° C. to about 135° C. In yet other embodiments of WIAM, the polymer is preheated to about 120° C. or about 130° C.

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is preheated to about 90° C. In another embodiment, the polymer is heated to about 100° C. In another embodiment, the polymer is preheated to about 30° C. below PMT and 2° C. below PMT. In another embodiment, the polymer is preheated to about 12° C. below PMT.

In the WIAM embodiment of WIR, the temperature of the polymer following irradiation is at or above the melting temperature of the polymer. Exemplary ranges of acceptable temperatures following irradiation are disclosed in greater detail in International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. In another embodiment, the temperature following irradiation is about 145° C. to about 190° C. In yet another embodiment, the temperature following irradiation is about 145° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

The total dose of irradiation may also be selected as a parameter in controlling the properties of the irradiated polymer. In particular, the dose of irradiation can be varied to control the degree of cross-linking and crystallinity in the irradiated polymer. Exemplary ranges of acceptable total dosages are disclosed in greater detail in International Application WO 97/29793.

The dose rate of irradiation also may be varied to achieve a desired result. The dose rate is a prominent variable in the WIAM process. In the case of WIAM irradiation of UHMWPE, higher dose rates would provide the least amount of reduction in toughness and elongation at break. The preferred dose rate of irradiation would be to administer the total desired dose level in one pass under the electron-beam. One also can deliver the total dose level with multiple passes under the beam, delivering a (equal or unequal) portion of the total dose at each time. This would lead to a lower effective dose rate.

Ranges of acceptable dose rates are exemplified in greater detail in International Application WO 97/29793. In general, the dose rates will vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

(iv) Subsequent Melting (SM)—Substantial Elimination of Detectable Residual Free Radicals:

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped in the crystalline regions and/or at crystalline lamellae surfaces leading to oxidation-induced instabilities in the long-term (see Kashiwabara, H. S. Shimada, and Y. Hori, Free Radicals and Cross-linking in Irradiated Polyethylene, Radiat. Phys. Chem., 1991, 37(1): p. 43-46; Jahan, M. S, and C. Wang, Combined Chemical and Mechanical Effects on Free radicals in UHMWPE Joints During Implantation, Journal of Biomedical Materials Research, 1991, 25: p. 1005-1017; Sutula, L. C., et al., Impact of gamma sterilization on clinical performance of polyethylene in the hip", Clinical Orthopedic Related Research, 1995, 3129: p. 1681-1689.). The elimination of these residual, trapped free radicals through heating can be, therefore, desirable in precluding long-term oxidative instability of the polymer. Jahan M. S. and C. Wang, "Combined chemical and mechanical effects on free radicals in UHMWPE joints during implantation", Journal of Biomedical Materials Research, 1991, 25: p. 1005-1017; Sutula, L. C., et al., "Impact of gamma sterilization on clinical performance of polyethylene in the hip", Clinical Orthopedic Related Research, 1995, 319: p. 28-4.

Residual free radicals may be reduced by heating the polymer above the melting to point of the polymer used. The heating allows the residual free radicals to recombine with each other. If for a given system the preform does not have substantially any detectable residual free radicals following irradiation, then a later heating step may be omitted. Also, if for a given system the concentration of the residual free radicals is low enough to not lead to degradation of device performance, the heating step may be omitted. In some of the lower molecular weight and lower density polyethylenes, the residual free radicals may recombine with each other even at room temperature over short periods of time, for example, few hours to few days, to few months. In such cases, the subsequent heating may be omitted if the increased crystallinity and modulus resulting from the irradiation is preferred. Otherwise, the subsequent heating may be carried out to decrease the crystallinity and modulus. In the case where the heating is omitted, the irradiated preform can be directly machined into the final medical device. The subsequent heating is also omitted if the polymer contains sufficient antioxidant to prevent oxidation in the long-term.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and degradation temperature ($T_d$) of the polymer, more preferably between about 3° C. above PMT and $T_d$, more preferably between about 10° C. above PMT and 50° C. above PMT, more preferably between about 10° C. and 12° C. above PMT and most preferably about 15° C. above PMT.

Preferably, for UHMWPE the polymer is heated to a temperature of about 137° C. to about 300° C., more preferably about 140° C. to about 300° C., more preferably yet about 140° C. to about 190° C., more preferably yet about 145° C. to about 300° C., more preferably yet about 145° C. to about 190° C., more preferably yet about 145° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, for example, in air, in an inert gas, e.g., nitrogen, argon or helium, in a sensitizing atmosphere, for example, acetylene, or in a vacuum. It is preferred that for the longer heating times, that the heating be carried out in an inert gas or under vacuum to avoid in-depth oxidation.

In certain embodiments, there may be an acceptable level of residual free radicals in which case, the post-irradiation annealing also can be carried out below the melting point of the polymer, the effects of such free radicals can be minimized or eliminated by an antioxidant.

(v) Sequential Irradiation:

The polymer is irradiated with either gamma or e-beam radiation in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be heating below the melting point or at the melting point of the polymer. The irradiation at any of the steps can be warm irradiation, cold irradiation, or melt irradiation, as described above. For example the polymer is irradiated with 30 kGy at each step of the cross-linking and it is first heated to about 120° C. and then annealed at about 120° C. for about 5 hours after each irradiation cycle.

(vi) Blending and Doping:

As stated above, the cross-liked polymeric material can optionally have a melt history, meaning it is melted concurrent with or subsequent to irradiation. The polymeric material can be blended with an antioxidant prior to consolidation and irradiation. Also, the consolidated polymeric material can be doped with an antioxidant prior to or after irradiation, and optionally can have been melted concurrent with or subsequent to irradiation. Furthermore, a polymeric material can both be blended with an antioxidant prior to consolidation and doped with an antioxidant after consolidation (before or after irradiation and optional melting). The polymeric material can be subjected to extraction at different times during the process, and can be extracted multiple times as well.

Definitions

"Antioxidant" refers to what is known in the art as (see, for example, WO 01/80778, U.S. Pat. No. 6,448,315). Alpha- and delta-tocopherol; propyl, octyl, or dedocyl gallates; lactic, citric, ascorbic, tartaric acids, and organic acids, and their salts; orthophosphates, tocopherol acetate. Vitamin E is a preferred antioxidant.

"High-pressure crystallization" refers to a method of making high pressure crystallized polyethylene, according to the invention, as described herein.

"High-pressure annealing" refers to a method of making high pressure crystallized polyethylene, according to the invention, as described herein.

The phrase "spatially controlled antioxidant distribution" refers to distribution of antioxidant in a controlled manner, such as a desired amount of an antioxidant or a mixture of antioxidants is(are) diffused in or blended in a polymeric material, in order to have a gradient of antioxidant distribution. A spatial distribution of the antioxidant allows formation of regions within a polymeric material having some regions rich and other regions poor in antioxidant content, which also can be termed as a medical implant or preform containing the spatially controlled antioxidant distribution.

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed; and then evaporate $CO_2$ from the mixture, UHMWPE doped with an antioxidant is obtained (see, for example, U.S. Pat. No. 6,448,315 and WO 02/26464)

The term "compression molding" as referred herein related generally to what is known in the art and specifically relates to high temperature molding polymeric material wherein polymeric material is in any physical state, including powder form, is compressed into a slab form or mold of a medical implant, for example, a tibial insert, an acetabular liner, a glenoid liner, a patella, or an unicompartmental insert, an interpositional device for any joint can be machined.

The term "direct compression molding" (DCM) as referred herein related generally to what is known in the art and specifically relates to molding applicable in polyethylene-based devices, for example, medical implants wherein polyethylene in any physical state, including powder form, is compressed to solid support, for example, a metallic back, metallic mesh, or metal surface containing grooves, undercuts, or cutouts. The compression molding also includes high temperature compression molding of polyethylene at various states, including resin powder, flakes and particles, to make a component of a medical implant, for example, a tibial insert, an acetabular liner, a glenoid liner, a patella, an interpositional device for any joint or an unicompartmental insert.

The term "mechanically interlocked" refers generally to interlocking of polyethylene and the counterface, that are produced by various methods, including compression molding, heat and irradiation, thereby forming an interlocking interface, resulting into a 'shape memory' of the interlocked polyethylene. Components of a device having such an interlocking interface can be referred to as a "hybrid material". Medical implants having such a hybrid material contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA).

"High temperature compression molding" refers to the compression molding of polyethylene in any form, for example, resin powder, flakes or particles, to impart new geometry under pressure and temperature. During the high temperature (above the melting point of polyethylene) compression molding, polyethylene is heated to above its melting point, pressurized into a mold of desired shape and allowed to cool down under pressure to maintain a desired shape.

"Shape memory" refers to what is known in the art as the property of polyethylene, for example, an UHMWPE, that attains a preferred high entropy shape when melted. The preferred high entropy shape is achieved when the resin powder is consolidated through compression molding.

The phrase "substantially no detectable residual free radicals" refers to a state of a polyethylene component, wherein enough free radicals are eliminated to avoid oxidative degradation, which can be evaluated by electron spin resonance (ESR). The phrase "detectable residual free radicals" refers to the lowest level of free radicals detectable by ESR or more. The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of cross-linking and/or a desired lack or quenching of free radicals, as is apparent to the skilled person from the teachings contained herein. This is due, at least in part, to the varying properties of polymer compositions. Thus these terms encompass values beyond those resulting from systematic error. These terms make explicit what is implicit.

"Polymeric materials" include polyethylene, for example, Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" generally refers to articles comprising any "polymeric material" disclosed herein.

"Polymeric materials" also include hydrogels, such as poly (vinyl alcohol), poly (acrylamide), poly (acrylic acid), poly (ethylene glycol), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" can be in the form of resin, flakes, powder, consolidated stock and can contain additives such as anti-oxidant(s). The "polymeric material" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

In one embodiment UHMWPE flakes are blended with α-tocopherol; preferably the UHMWPE/α-tocopherol blend is heated to diffuse the α-tocopherol into the flakes. The UHMWPE/α-tocopherol blend is further blended with virgin UHMWPE flakes to obtain a blend of UHMWPE flakes where some flakes are poor in α-tocopherol and others are rich in α-tocopherol. This blend is then consolidated and irradiated. During irradiation the α-tocopherol-poor regions are more highly cross-linked than the α-tocopherol-poor regions. Following irradiation the blend is homogenized to diffuse α-tocopherol from the α-tocopherol rich to α-tocopherol-poor regions and achieve oxidative stability throughout the polymer.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly (ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

"Cross-linking Polymeric Materials" refers to polymeric materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE also can be obtained through cold irradiation, warm irradiation, or melt irradiation according to the teachings of U.S. Pat. Nos. 5,879,400, 6,641, 617, and PCT/US97/02220.

"Consolidated polymeric material refers" to a solid, consolidated bar stock, solid material machined from stock, or semi-solid form of polymeric material derived from any forms as described herein, for example, resin powder, flakes, particles, or a mixture thereof, that can be consolidated. The consolidated polymeric material also can be in the form of a slab, block, solid bar stock, machined component, film, tube, balloon, pre-form, implant, finished medical device or unfinished device.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Pharmaceutical compound", as described herein, refers to a drug in the form of a powder, suspension, emulsion, particle, film, cake, or molded form. The drug can be free-standing or incorporated as a component of a medical device.

The term "pressure chamber" refers to a vessel or a chamber in which the interior pressure can be raised to levels above atmospheric pressure.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "sealing" refers to the process of isolating a chamber or a package from the outside atmosphere by closing an opening in the chamber or the package. Sealing can be accomplished by a variety of means, including application of heat (for example, thermally-sealing), use of adhesive, crimping, cold-molding, stapling, or application of pressure.

The term "blister packs" refers to a packaging comprised of a rigid plastic bowl with a lid or the like that is either peeled or punctured to remove the packaged contents. The lid is often made of aluminum, or a gas-permeable membrane such as a Tyvek. The blister packs are often blow-molded, a process where the plastic is heated above its deformation temperature, at which point pressurized gas forces the plastic into the required shape.

The term "heat-shrinkable packaging" refers to plastic films, bags, or tubes that to have a high degree of orientation in them. Upon application of heat, the packaging shrinks down as the oriented chains retract, often wrapping tightly around the medical device.

The term "intervertebral disc system" refers to an artificial disc that separates the vertebrae in the spine. This system can either be composed of one type of material, or can be a composite structure, for example, cross-linked UHMWPE with metal edges.

The term "balloon catheters" refers to what is known in the art as a device used to expand the space inside blood vessels or similar. Balloon catheters are usually thin wall polymeric devices with an inflatable tip, and can expand blocked arteries, stents, or can be used to measure blood pressure. Commonly used polymeric balloons include, for example, polyether-block co-polyamide polymer (PeBAX®), Nylon, and polyethylene terephthalate (PET) balloons. Commonly used polymeric material used in the balloons and catheters include, for example, co-polymers of polyether and polyamide (for example, PeBAX®), Polyamides, Polyesters (for example, PET), and ethylene vinyl alcohol (EVA) used in catheter fabrication.

Medical device tubing: Materials used in medical device tubing, including an intravenous tubing include, polyvinyl chloride (PVC), polyurethane, polyolefins, and blends or alloys such as thermoplastic elastomers, polyamide/imide, polyester, polycarbonate, or various fluoropolymers.

The term "stent" refers to what is known in the art as a metallic or polymeric cage-like device that is used to hold bodily vessels, such as blood vessels, open. Stents are usually introduced into the body in a collapsed state, and are inflated at the desired location in the body with a balloon catheter, where they remain.

"Melt transition temperature" refers to the lowest temperature at which all the crystalline domains in a material disappear.

The term "interface" in this invention is defined as the niche in medical devices formed when an implant is in a configuration where a component is in contact with another piece (such as a metallic or a non-metallic component), which forms an interface to between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process.

"Irradiation", in one aspect of the invention, the type of radiation, preferably ionizing, is used. According to another aspect of the invention, a dose of ionizing radiation ranging from about 25 kGy to about 1000 kGy is used. The radiation dose can be about 25 kGy, about 50 kGy, about 65 kGy, about 75 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any value thereabout or therebetween. Preferably, the radiation dose can be between about 25 kGy and about 150 kGy or between about 50 kGy and about 100 kGy. These types of radiation, including gamma and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a vacuum. The irradiation also can be carried out at room temperature, or at between room temperature and the melting point of the polymeric material, or at above the melting point of the polymeric material.

In accordance with a preferred feature of this invention, the irradiation may be carried out in a sensitizing atmosphere. This may comprise a gaseous substance which is of sufficiently small molecular size to diffuse into the polymer and which, on irradiation, to acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

"Metal Piece", in accordance with the invention, the piece forming an interface with polymeric material is, for example, a metal. The metal piece in functional relation with polyethylene, according to the present invention, can be made of a cobalt chrome alloy, stainless steel, titanium, titanium alloy or nickel cobalt alloy, for example.

"Non-metallic Piece", in accordance with the invention, the piece forming an interface with polymeric material is, for example, a non-metal. The non-metal piece in functional relation with polyethylene, according to the present invention, can be made of ceramic material, for example.

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refer to an inert gas, inert fluid, or inert liquid medium, such as nitrogen gas or silicon oil.

"Anoxic environment" refers to an environment containing gas, such as nitrogen, with less than 21%-22% oxygen, preferably with less than 2% oxygen. The oxygen concentration in an anoxic environment also can be at least about 1%, 2%, 4%, 6%, 8%, 10%, 12% 14%, 16%, 18%, 20%, or up to about 22%, or any value thereabout or therebetween.

The term "vacuum" refers to an environment having no appreciable amount of gas, which otherwise would allow free radicals in polymeric materials to form cross links is without oxidation during a process of sterilization. A vacuum is used to avoid $O_2$, which would otherwise oxidize the medical device comprising a polymeric material, such as UHMWPE. A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

"Residual free radicals" refers to free radicals that are generated when a polymer is exposed to ionizing radiation such as gamma or e-beam irradiation. While some of the free radicals recombine with each other to from cross-links, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals.

"Sterilization", one aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from 25-200 kGy. The dose level of sterilization is higher than standard levels used in irradiation. This is to allow cross-linking or further cross-linking of the medical implants during sterilization.

In another aspect, the invention discloses a process of sterilizing medical implants containing polymeric material, such as cross-linked UHMWPE, that is in contact with another piece, including polymeric material consolidated by compression molding to another piece, thereby forming an interface and an interlocked hybrid material, comprising sterilizing an interface by ionizing radiation; heating the medium to above the melting point of the irradiated UHMWPE (above about 137° C.) to eliminate the crystalline matter and allow for the recombination/elimination of the residual free radicals; and sterilizing the medical implant with a gas, for example, ethylene oxide or gas plasma.

One aspect of the present invention discloses a process of increasing the uniformity of the antioxidant following doping in polymeric component of a medical implant during the manufacturing process by heating for a time period depending on the melting temperature of the polymeric material. For example, the preferred temperature is about 137° C. or less. Another aspect of the invention discloses a heating step that can be carried in the air, in an atmosphere, containing oxygen, wherein the oxygen concentration is at least about 1%, 2%, 4%, or up to about 22%, or any value thereabout or therebetween. In another aspect, the invention discloses a heating step that can be carried while the implant is in contact with an inert atmosphere, wherein the inert atmosphere contains gas selected from the group consisting of nitrogen, argon, helium, neon, or the like, or a combination thereof. In another aspect, the invention discloses a heating step that can be carried while the implant is in contact with a non-oxidizing medium, such as an inert fluid medium, wherein the medium contains no more than about 1% oxygen. In another aspect, the invention discloses a heating step that can be carried while the implant is in a vacuum.

In theoretical thermodynamics, "adiabatic heating" refers to an absence of heat transfer to the surroundings. In the practice, such as in the creation of new polymeric materials, adiabatic heating refers to situations where the vast majority of thermal energy is imparted on the starting material and is not transferred to the surroundings. Such can to be achieved by the combination of insulation, irradiation dose rates and irradiation time periods, as disclosed herein and in the documents cited herein. Thus, what may approach adiabatic heating in the theoretical sense achieves it in the practical sense. However, not all warm irradiation refers to an adiabatic heating. Warm irradiation also can have non-adiabatic or partially (such as 10-75% of the heat generated are lost to the surroundings) adiabatic heating.

In another aspect of this invention, there is described the heating method of implants to increase the uniformity of the antioxidant. The medical device comprising a polymeric raw material, such as UHMWPE, is generally heated to a temperature of about 137° C. or less following the step of doping with the antioxidant. The medical device is kept heated in the inert medium until the desired uniformity of the antioxidant is reached.

The term "below melting point" or "below the melt" refers to a temperature below the melting point of a polymeric material, for example, polyethylene such as UHMWPE. The term "below melting point" or "below the melt" refers to a temperature less than about 145° C., which may vary depending on the melting temperature of the polyethylene, for example, about 145° C., 140° C. or 135° C., which again depends on the properties of the polyethylene being treated, for example, molecular weight averages and ranges, batch variations, etc. The melting temperature is typically measured using a differential scanning calorimeter (DSC) at a heating rate of 10° C. per minute. The peak melting temperature thus measured is referred to as melting point, also referred as transition range in temperature from crystalline to amorphous phase, and occurs, for example, at approximately 137° C. for some grades of UHMWPE. It may be desirable to conduct a melting study on the starting polyethylene material in order to determine the melting temperature and to decide upon an irradiation and annealing temperature. Generally, the melting temperature of polymeric material is increased when the polymeric material is under pressure.

The term "annealing" refers to a thermal treatment condition in accordance with the invention. Annealing generally refers to heating the polymeric material at a temperature below or above its peak melting point. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention.

The term "contacted" includes physical proximity with or touching such that the sensitizing agent can perform its intended function. Preferably, a polyethylene composition or pre-form is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below the melting point of the material. The contact period ranges from at least about 1 minute to several weeks and the duration depending on the temperature of the environment.

The term "non-oxidizing" refers to a state of polymeric material having an oxidation index (A. U.) of less than about 0.5 following aging polymeric materials for 5 weeks in air at 80° C. oven. Thus, a non-oxidizing cross-linked polymeric material generally shows an oxidation index (A. U.) of less than about 0.5 after the aging period.

The term "surface" of a polymeric material refers generally to the exterior region of the material having a thickness of about 1.0 µm to about 2 cm, preferably about 1.0 mm to about 5 mm, more preferably about 2 mm of a polymeric material or a polymeric sample or a medical device comprising polymeric material.

The term "bulk" of a polymeric material refers generally to an interior region of the material having a thickness of about 1.0 µm to about 2 cm, preferably about 1.0 mm to about 5 mm, more preferably about 2 mm, from the surface of the polymeric material to the center of the polymeric material. However, the bulk may include selected sides or faces of the polymeric material including any selected surface, which may be contacted with a higher concentration of antioxidant.

Although the terms "surface" and "bulk" of a polymeric material generally refer to exterior regions and the interior regions, respectively, there generally is no discrete boundary between the two regions. But, rather the regions are more of a gradient-like transition. These can differ based upon the size and shape of the object and the resin used.

The term "doping" refers to a general process well known in the art (see, for example, U.S. Pat. Nos. 6,448,315 and 5,827,904). In general, it refers to incorporating an additive 'dopant' into the polymeric material in quantities less than 50%. In this connection, doping generally refers to contacting a polymeric material with an antioxidant under certain conditions, as set forth herein, for example, doping UHMWPE with an antioxidant under supercritical conditions.

In certain embodiments of the present invention in which doping of antioxidant is carried out at a temperature above the melting point of the polymeric material, the antioxidant-doped polymeric material can be further heated above the melt or annealed to eliminate residual free radicals after irradiation. Melt-irradiation of polymeric material in presence of an antioxidant, such as vitamin E, can change the distribution of the vitamin E concentration and also can change the mechanical properties of the polymeric material. These changes can be induced by changes in crystallinity and/or by the plasticization effect of vitamin E at certain concentrations.

According to one embodiment, the surface of the polymeric material is contacted with little or no antioxidant and bulk of the polymeric material is contacted with a higher concentration of antioxidant.

According to another embodiment, the surface of the polymeric material is contacted with no antioxidant and bulk of the polymeric material is contacted with a higher concentration of antioxidant.

According to one embodiment, the bulk of the polymeric material is contacted with little or no antioxidant and surface of the polymeric material is contacted with a higher concentration of antioxidant.

According to another embodiment, the bulk of the polymeric material is contacted with no antioxidant and surface of the polymeric material is contacted with a higher concentration of antioxidant.

According to another embodiment, the surface of the polymeric material and the bulk of the polymeric material are contacted with the same concentration of antioxidant.

According to one embodiment, the surface of the polymeric material may contain from about 0 wt % to about 50 wt % antioxidant, preferably about 0.001 wt % to about 10 wt %, preferably between about 0.01 wt % to about 0.5 wt %, more preferably about 0.2 wt %. According to another embodiment, the bulk of the polymeric material may contain from about 0 wt % to about 50 wt %, preferably about 0.001 wt % to about 10 wt %, preferably between about 0.01 wt % to about 0.5 wt %, more preferably about 0.2 wt %, preferably between about 0.2 wt % and about 1% wt %, preferably about 0.5 wt %.

According to another embodiment, the surface of the polymeric material and the bulk of the polymeric material contain the same concentration of antioxidant.

More specifically, consolidated polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid.

The antioxidant can be diffused to a depth of about 5 mm or more from the surface, for example, to a depth of about 3-5 mm, about 1-3 mm, or to any depth thereabout or therebetween.

The doping process can involve soaking of a polymeric material, medical implant or device with an antioxidant, such as vitamin E, for about half an hour up to several days, preferably for about one hour to 24 hours, more preferably for one hour to 16 hours. The antioxidant can be at room temperature or heated up to about 137° C. and the doping can be carried out at room temperature or at a temperature up to about 137° C. Preferably the antioxidant solution is heated to a temperature between about 100° C. and 135° C. or to between about 110° C. and 130° C., and the doping is carried out at a temperature between about 100° C. and 135° C. or between about 110° C. and 130° C. More preferably, the antioxidant solution is heated to about 120° C. and the doping is carried out at about 120° C.

Doping with α-tocopherol through diffusion at a temperature above the melting point of the irradiated polyethylene (for example, at a temperature above 137° C.) can be carried out under reduced pressure, ambient pressure, elevated pressure, and/or in a sealed chamber, for about 0.1 hours up to several days, preferably for about 0.5 hours to 6 hours or more, more preferably for about 1 hour to 5 hours. The antioxidant can be at a temperature of about 137° C. to about 400° C., more preferably about 137° C. to about 200° C., more preferably about 137° C. to about 160° C.

The doping and/or the irradiation steps can be followed by an additional step of "homogenization", which refers to a heating step in air or in anoxic environment to improve the spatial uniformity of the antioxidant concentration within the polymeric material, medical implant or device. Homogenization also can be carried out before and/or after the irradiation step. The heating may be carried out above or below or at the peak melting point. Antioxidant-doped or -blended polymeric material can be homogenized at a temperature below or above or at the peak melting point of the polymeric material for a desired period of time, for example, the antioxidant-doped or -blended polymeric material can be homogenized for about an hour to several days at room temperature to about 400° C. Preferably, the homogenization is carried out at 90° C. to 180° C., more preferably 100° C. to 137° C., more preferably 120° C. to 135° C., most preferably 130° C. Homogenization is preferably carried out for about one hour to several days to two weeks or more, more preferably about 12 hours to 300 hours or more, more preferably about 280 hours, or more preferably about 200 hours. More preferably, the homogenization is carried out at about 130° C. for about 36 hours or at about 120° C. for about 24 hours. The polymeric material, medical implant or device is kept in an inert atmosphere (nitrogen, argon, and/or the like), under vacuum, or in air during the homogenization process. The homogenization also can be performed in a chamber with supercritical fluids such as carbon dioxide or the like. The pressure of the supercritical fluid can be about 1000 to about 3000 psi or more, more preferably about 1500 psi. It is also known that pressurization increases the melting point of UHMWPE. A higher temperature than 137° C. can be used for homogenization below the melting point if applied pressure has increased the melting point of UHMWPE.

The polymeric material, medical implant or device is kept in an inert atmosphere (nitrogen, argon, and/or the like), under vacuum, or in air during the homogenization process. The homogenization also can be performed in a chamber with supercritical fluids such as carbon dioxide or the like. The pressure of the supercritical fluid can be 1000 to 3000 psi or more, more preferably about 1500 psi. The homogenization can be performed before and/or after and/or during the diffusion of the antioxidant.

The terms "extraction" or "elution" of antioxidant from antioxidant containing consolidated polymeric material refers to partial or complete removal of the antioxidant, for example, vitamin E, from the consolidated polymeric material by various processes disclosed herein. For example, the extraction or elution of antioxidant can be done with a compatible solvent that dissolves the antioxidant contained in the consolidated polymeric material. Such solvents include, but not limited to, a hydrophobic solvent, such as hexane, heptane, or a longer chain alkane; an alcohol such as ethanol, any member of the propanol or butanol family or a longer chain alcohol; or an aqueous solution in which an antioxidant, such as vitamin E is soluble. Such a solvent also can be made by using an emulsifying agent such as Tween 80 or ethanol. The extraction or elution of antioxidant from antioxidant containing consolidated polymeric material is generally done prior to placement and/or implantation of the polymeric material, or a medical implant comprising the antioxidant containing consolidated polymeric material, into the body.

Extraction of α-tocopherol from a polyethylene at a temperature below the melting temperature of the polyethylene can be achieved by placing the polyethylene in an open or in a sealed chamber. A solvent or an aqueous solution also can be added in order to extract the α-tocopherol from polyethylene. The chamber is then heated below the melting point of the polyethylene, preferably between about room temperature to near the melting point, more preferably about 100° C. to about 137° C., more preferably about 120° C., or more preferably about 130° C. If a sealed chamber is used, there will be an increase in pressure during heating. Because the polyethylene is cross-linked, only the crystalline regions melt. The chemical cross-links between chains remain intact and allow the polyethylene to maintain its shape throughout the process despite surpassing its melting temperature. Increasing pressure increases the melting temperature of the polymeric material. In this case, homogenization below the melt is performed under pressure above 137° C., for example at about 145° C.

Extraction of α-tocopherol from a polyethylene at a temperature above the melting temperature of the polyethylene can be achieved by placing the polyethylene in an open or in a sealed chamber. A solvent or an aqueous solution also can be added in order to extract the α-tocopherol from polyethylene. The chamber is then heated above the melting point of the polyethylene, preferably between about 137° C. to about 400° C., more preferably about 137° C. to about 200° C., more preferably about 137° C., or more preferably about 160° C. If a sealed chamber is used, there will be an increase in pressure during heating. Because the polyethylene is cross-linked, only the crystalline regions melt. The chemical cross-links between chains remain intact and allow the polyethylene to maintain its shape throughout the process despite surpassing its melting temperature. Since crystallites pose a hindrance to diffusion of α-tocopherol in polyethylene, increasing the temperature above the melting point should increase the rate of extraction of α-tocopherol. Increasing pressure increases the melting temperature of the polymeric material.

The term "plasticizing agent" refers to what is known in the art, a material with a molecular weight less than that of the base polymer, for example vitamin E α-tocopherol) in unirradiated or cross-linked ultrahigh molecular weight polyethylene or low molecular weight polyethylene in high molecular weight polyethylene, in both cases ultrahigh molecular weight polyethylene being the base polymer. The plasticizing agent is typically added to the base polymer in less than about 20 weight percent. The plasticizing agent generally increases flexibility and softens the polymeric material.

The term "plasticization" or "plasticizing" refers to the properties that a plasticizing agent imparts on the polymeric material to which it has been contacted with. These properties may include but are not limited to increased elongation at break, reduced stiffness and increased ductility.

The invention is further described by the following examples, which do not limit the invention in any manner.

EXAMPLES

Vitamin E: Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

Example 1

Figure 3A:
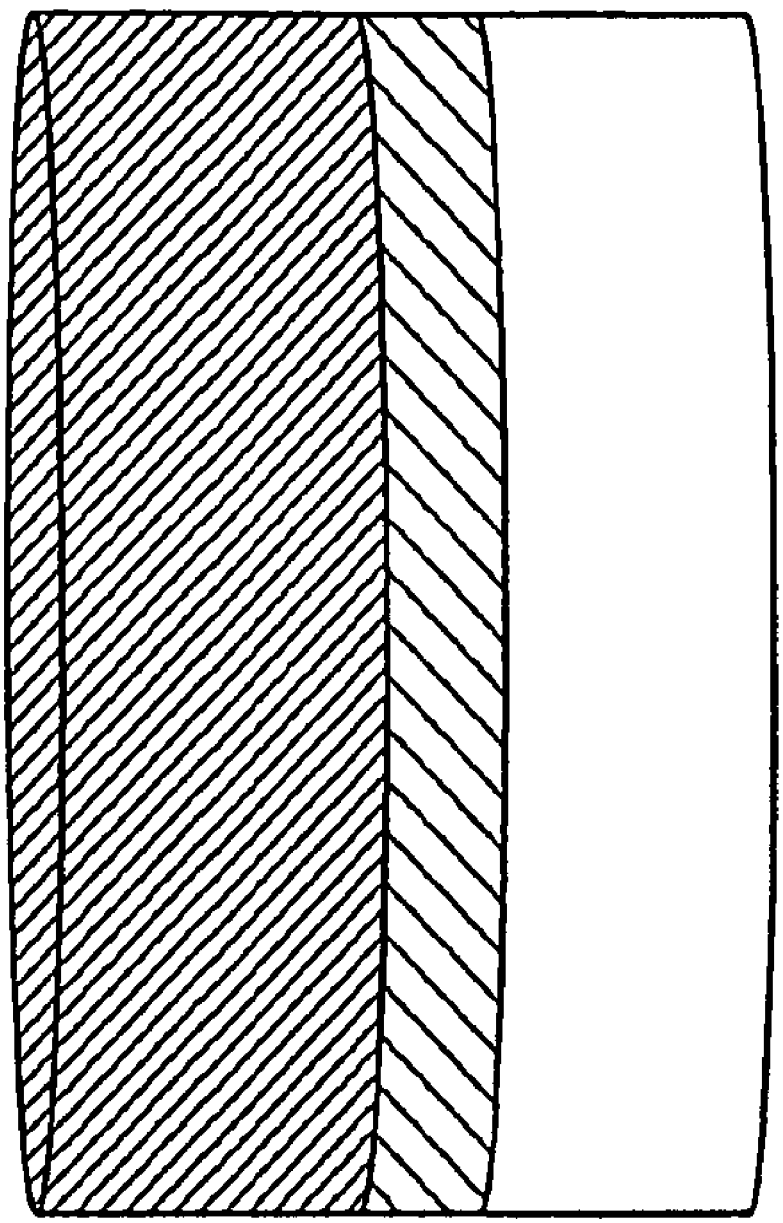
FIG. 3A shows a 1.5" thick UHMWPE puck. The puck was made from half GUR 1050 blended with 0.5 wt % α-tocopherol and half virgin GUR 1050 powder (1.5" thick and 2.5" in diameter). The light brown half on the left contains α-tocopherol.

DCM of UHMWPE Pucks Containing α-Tocopherol-Rich Regions and α-Tocopherol-Poor Regions Two puck-shaped pieces of UHMWPE, both 2.5" in diameter, were direct compression molded (DCM). One puck was 1" thick, the other one was 1.5" thick. The 1" thick puck was produced using a standard molding cycle in which the bottom half of the mold was filled with GUR 1050 powder containing 0.5 wt % α-tocopherol and the top half with virgin GUR 1050 powder. The 1.5" thick puck was produced using a modified molding cycle, in which the bottom half of the mold was filled with GUR 1050 powder containing 0.5 wt % α-tocopherol and compressed at room temperature under a pressure of 1220 psi. Following release of the pressure, the top half of the mold was filled with virgin GUR 1050 powder followed by a standard DCM cycle. A picture of the 1.5" thick puck is shown in FIG. 3A.

A thin film was microtomed across the sample from both of the pucks for FTIR analysis of the Vitamin E Index (VEI) as a function of depth within the sample. The thin cross-section was then analyzed using an infrared microscope. Infrared spectra were collected as a function of depth away from one of the edges that coincided with the free surface of the sample. The absorbance between 1226 and 1295 $cm^{-1}$ is characteristic of α-tocopherol (vitamin E) and polyethylene does not absorb near these frequencies. For polyethylene, the 1895 $cm^{-1}$ wave number for the $CH_2$ rocking mode is a typical choice as an internal reference. The normalized value, which is the ratio of the integrated absorbances of 1260 $cm^{-1}$ and 1895 $cm^{-1}$, is an index that provides a relative metric of α-tocopherol composition in polyethylene and is termed the vitamin E index.

Figure 3B:
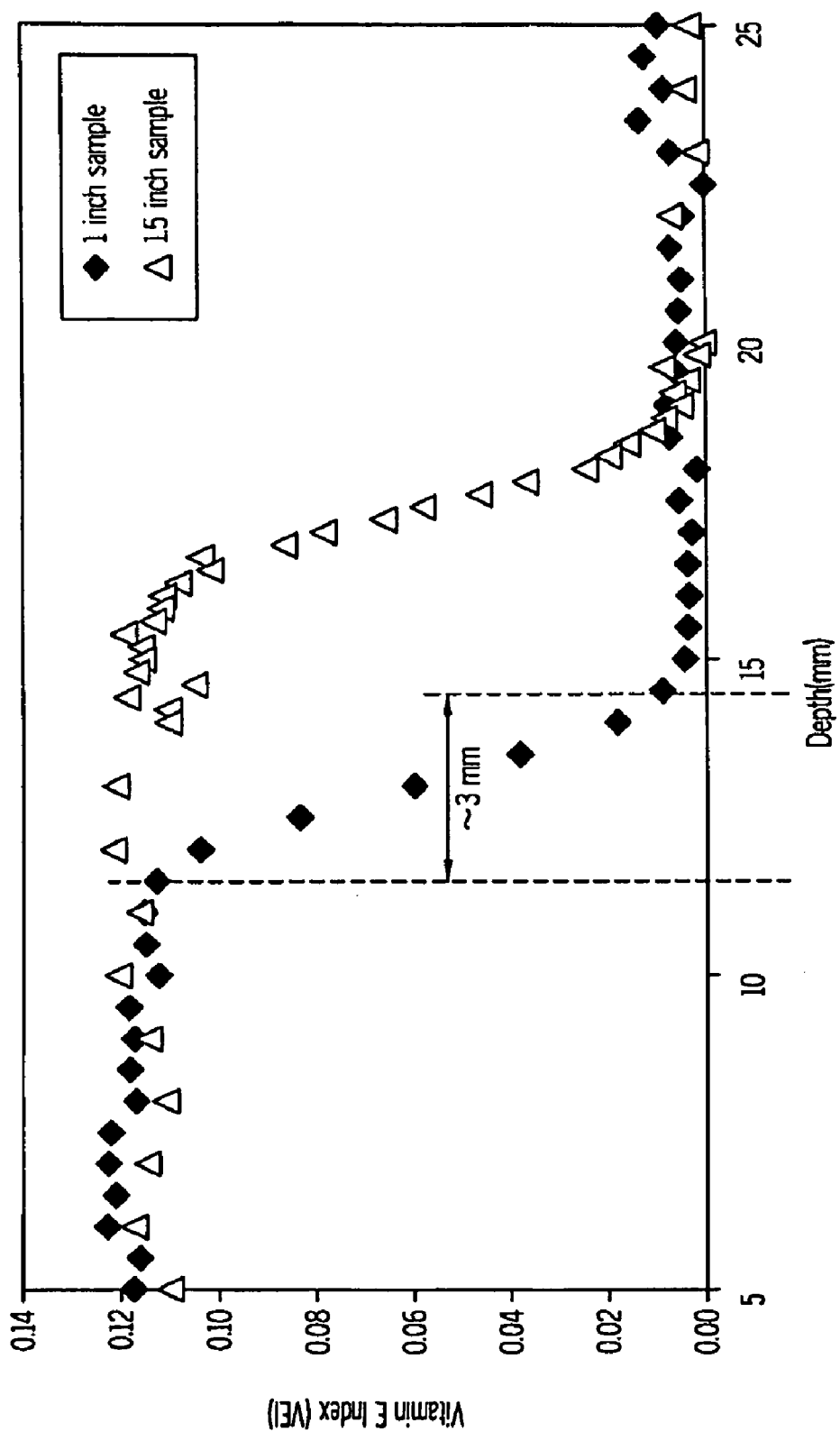
FIG. 3B illustrates a plot of Vitamin E Index (VEI) vs. depth (measured through the thickness of the puck). There is a smooth transition from constant Vitamin E content at the left side of the plot to virgin UHMWPE on the right side of the plot. The transition occurs over a relatively small range of 3 mm.

A plot of VEI as a function of depth (measured through the thickness of the puck) is shown in FIG. 3B. For both samples, the data show a smooth, linear transition from a constant VEI (~0.12) at the left of the plot to a VEI value of zero at the right of the plot. The distance over which the VEI transitions to zero is approximately 3 mm, which is relatively small and indicates that parts with α-tocopherol-rich and α-tocopherol-poor regions can be molded using a standard DCM cycle without excessive bleeding of the α-tocopherol from the blended to the virgin regions.

The pucks were subjected to a series of processing steps, which included:
 1. Irradiation via electron beam to a dose of 100 kGy;
 2. Annealing (1.5" puck) or doping/homogenization (1" puck) to infuse virgin polyethylene regions with α-tocopherol; and
 3. Accelerated aging for 2 weeks in oxygen at a pressure of 5 atm (ASTM F2003-02).

Following aging, the samples were subjected to pin-on-disk wear testing, with the articulating surface of the pin corresponding to the initially virgin polyethylene side of the puck.

Figure 4A:
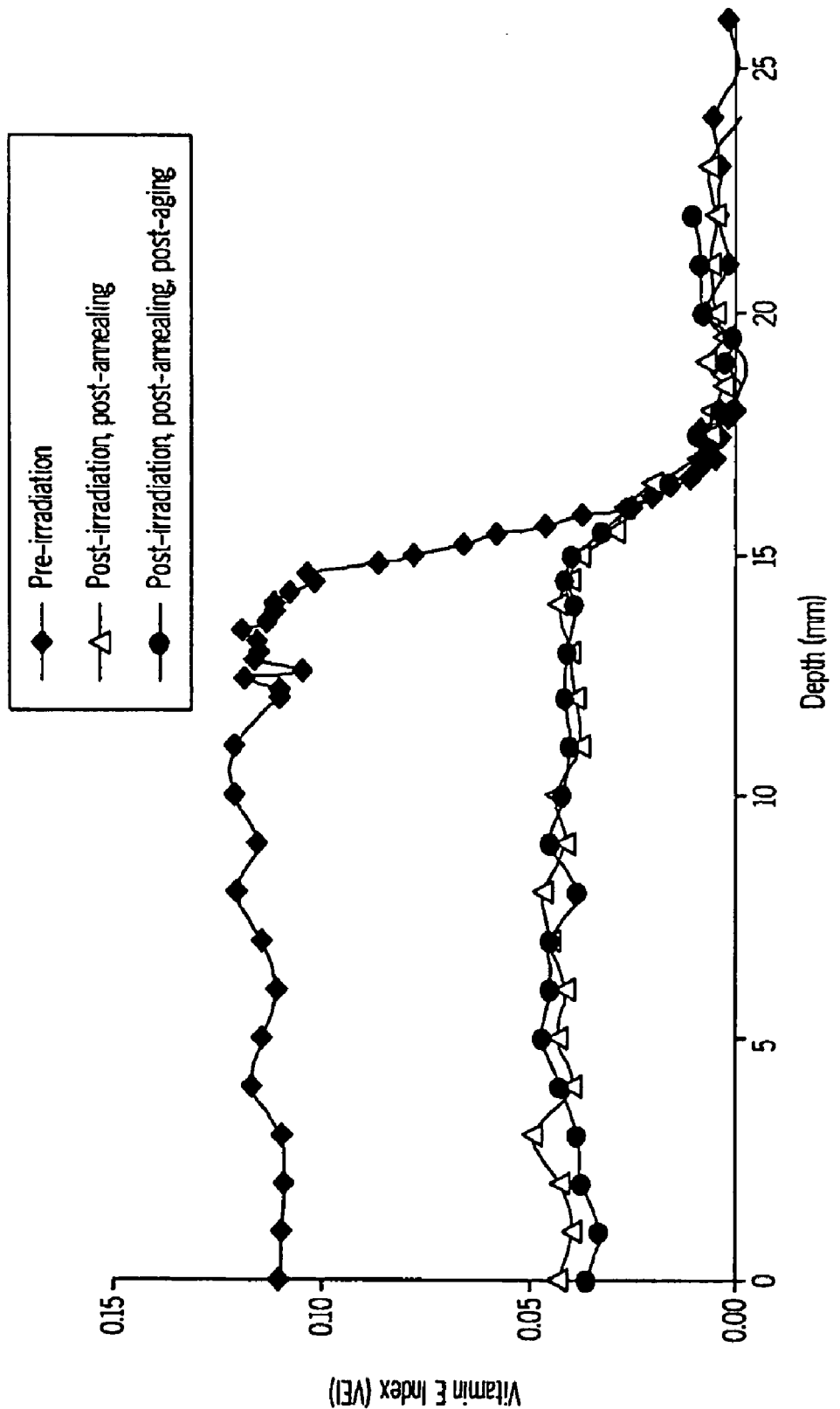
FIG. 4A shows Vitamin E Index (VEI) for 1.5" thick UHMWPE puck made with both α-tocopherol containing UHMWPE powder and virgin UHMWPE powder before and after irradiation.
Figure 4B:
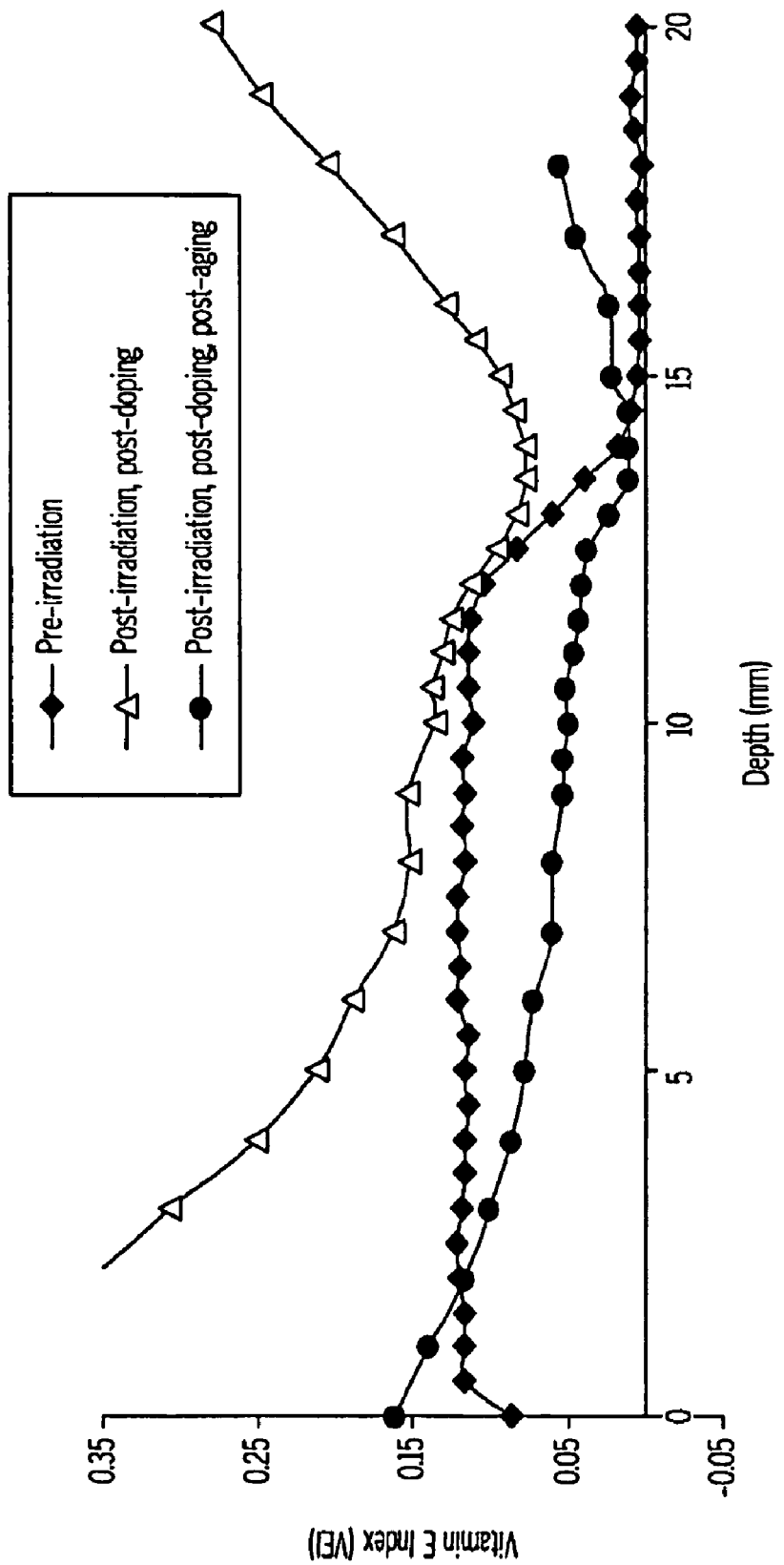
FIG. 4B shows VEI for 1" thick UHMWPE puck made with both α-tocopherol containing UHMWPE powder and virgin UHMWPE powder before and after irradiation.

In FIG. 4A, the Vitamin E Index (VEI) for the 1.5" thick puck at various stages of processing is shown. The effect of irradiation to 100 kGy is to reduce significantly the measured Vitamin E Index in the region with α-tocopherol, from a value of 0.11-0.12 before irradiation to a value of approximately 0.04 after irradiation. Subjecting the sample to an annealing step, whereby the sample was heated to 130° C. under Argon and held for 62 hours, did not lead to significant penetration of α-tocopherol into the virgin polyethylene region. This indicates that irradiation may facilitate attachment of the α-tocopherol to the UHMWPE chains, thereby stopping diffusion of α-tocopherol in this sample. In FIG. 4B, VEI data are plotted for the 1" thick puck, which was subjected to irradiation, followed by doping in α-tocopherol at 120° C. for 3 hours and homogenization at 130° C. for 36 hours. The VET data show that α-tocopherol diffused into the sample from both sides, and the side that already contained α-tocopherol has higher VEI values after doping. There is complete penetration of the part by α-tocopherol after this relatively short doping and homogenization cycle. (For comparison, complete penetration of an initially virgin puck of UHMWPE would require approximately 200 hours of homogenization). The effect of aging, in this case, is to reduce significantly the values of the Vitamin E index throughout the entire sample.

Figure 5:
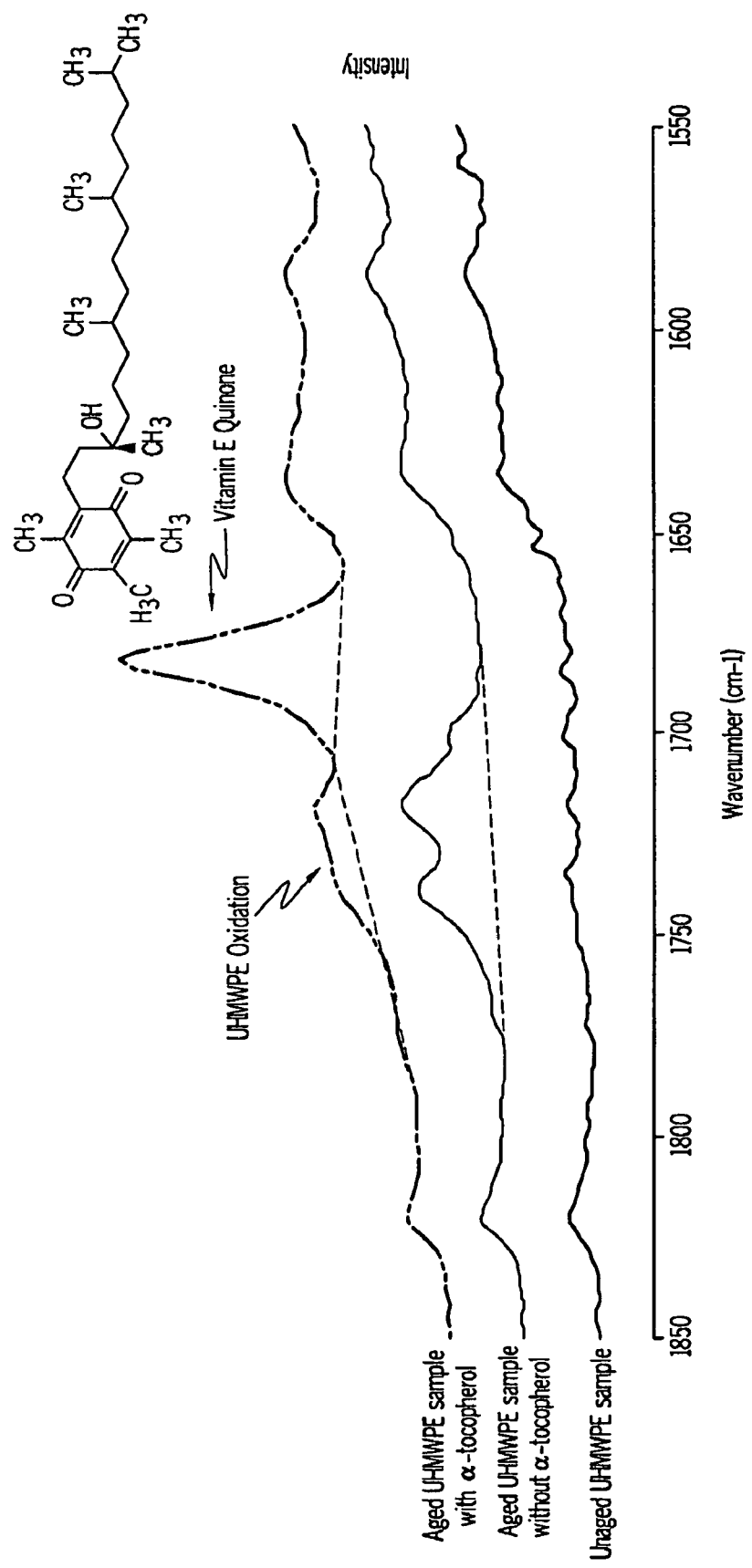
FIG. 5 depicts FTIR spectra for UHMWPE highlighting the difference between aged UHMWPE with and without α-tocopherol.

In order to determine the extent of oxidation in the samples, a modified calculation protocol was utilized, which is illustrated in FIG. 5. There are three FTIR spectra plotted in FIG. 5: one shows a typical spectrum for an unaged UHMWPE sample, one shows for an aged UHMWPE sample containing no α-tocopherol, and finally one shows for an aged sample containing a significant amount of α-tocopherol. The effect of oxidation on the FTIR spectrum of UHMWPE in the absence of α-tocopherol is manifested as a broad peak in the wavenumber range of 1680 $cm^{-1}$-1780 $cm^{-1}$ (due to the formation of carbonyl groups on the UHMWPE chains). In the unaged sample, no peaks are observed within this wavenumber range, indicating no measurable oxidation. In the aged sample containing no α-tocopherol, a broad peak is observed within the range 1680 $cm^{-1}$-1780 $cm^{-1}$. The spectrum for the UHMWPE sample containing α-tocopherol has an additional peak at 1680 $cm^{-1}$, which is due to the formation of the quinone version of α-tocopherol (as shown in FIG. 5). The lower wavenumber associated with the quinone is due to the conjugated nature of its carbonyl groups. The value of the oxidation index of UHMWPE was determined to be the integrated region between 1705 $cm^{-1}$-1780 $cm^{-1}$, thereby avoiding the quinone peak. An additional parameter was calculated, here referred to as the Vitamin E Quinone Index (VEQI), which was the integrated region between 1660 $cm^{-1}$-1700 $cm^{-1}$.

Figure 6A:
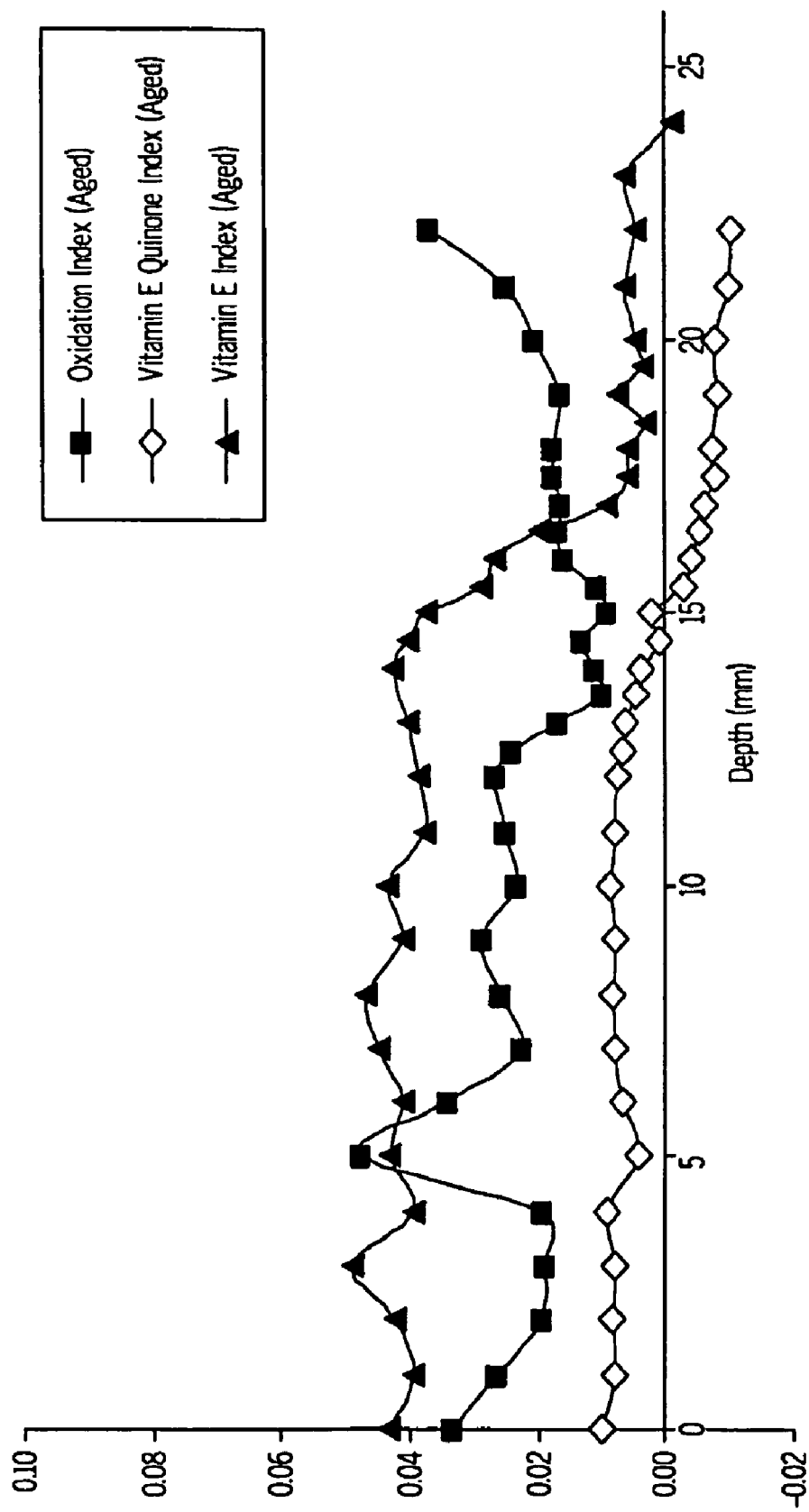
FIG. 6A shows Oxidation index (OI), Vitamin E Index (VEI), and Vitamin E Quinone Index (VEQI) for a 1.5" UHMWPE puck that was subjected to annealing and aging. The trend between VEI and VEQI is notable as compared to FIG. 6B.
Figure 6B:
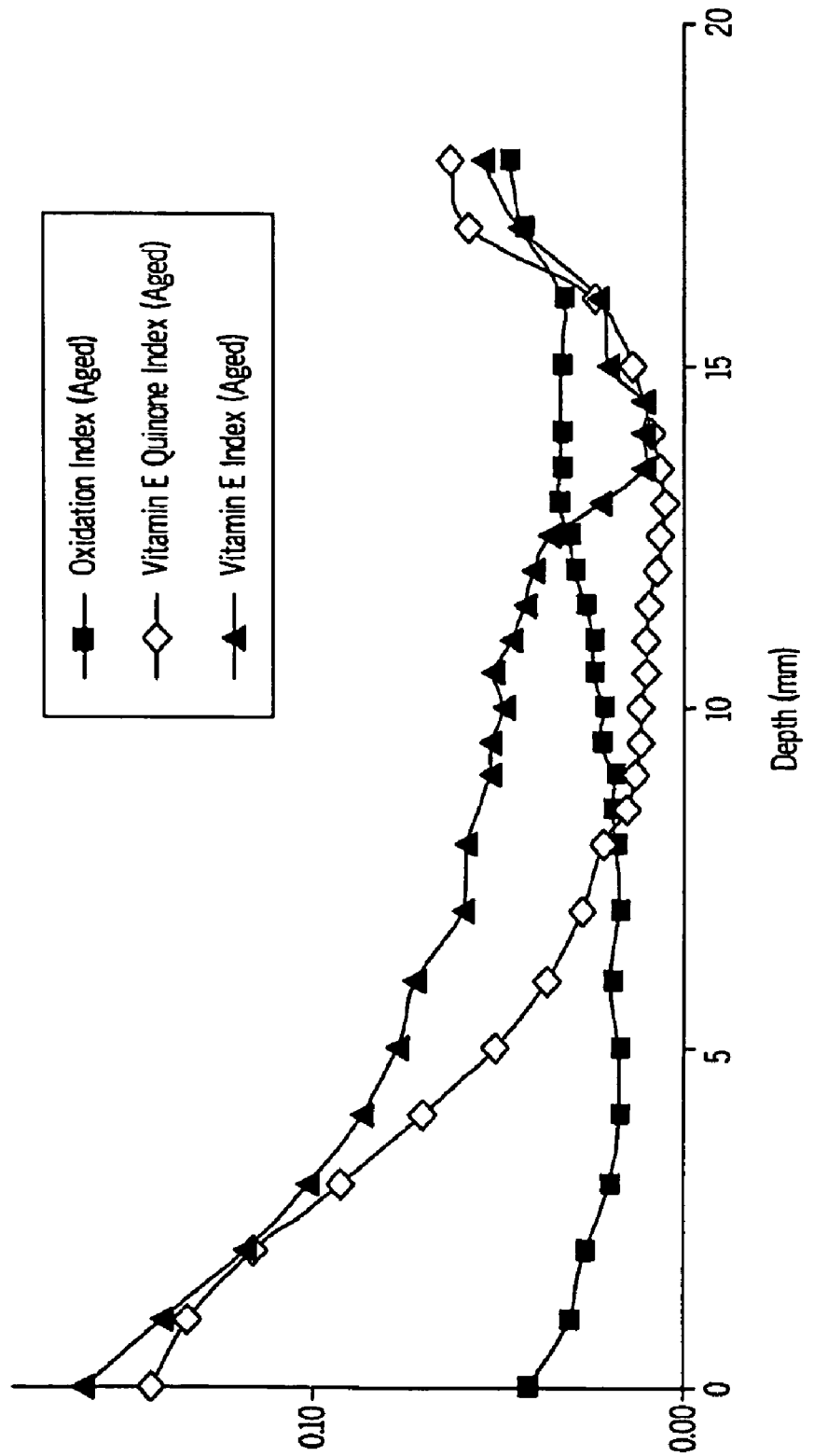
FIG. 6B shows Oxidation index (OI), Vitamin E Index (VEI), and Vitamin E Quinone Index (VEQI) for a 1" UHMWPE puck that was subjected to doping, homogenization, and aging. The trend between VEI and VEQI is notable as compared to FIG. 6A.

In FIG. 6, the values of the oxidation index (OI) of UHMWPE, the Vitamin E Index (VEI), and the Vitamin E Quinone Index (VEQI) are plotted for both the 1.5" annealed sample after aging (see FIG. 6A) and for the 1" doped sample after aging (see FIG. 6B). In FIG. 6A, the VEI values, as shown earlier, are relatively constant for the 10, first 15 mm, followed by a gradual drop to zero and a subsequent region of virgin UHMWPE. The effect of accelerated aging on the OI appears to be insignificant. In the α-tocopherol-containing region of the sample, the OI values are relatively constant, centered around a value of ~0.03. Only at the edge of the sample containing no α-tocopherol (19-22 mm) is there a trend in OI. This is the portion of the sample containing no α-tocopherol, thus an increase in OI is not surprising, however it is not large. Regarding the VEQI, all values are very small (≦0.01), however there is a trend from a higher, slightly positive value in the region containing α-tocopherol, to a slightly negative value in the region without α-tocopherol. Thus it appears that there is conversion of the α-tocopherol to its quinone form at a relatively small rate during the aging process.

In FIG. 6B, the VEQI values show a more significant correlation with the VEI values. In particular, in the region where the VEI values are highest, near the surfaces, the VEQI values are also highest, indicating greater conversion to the quinone form of α-tocopherol with greater concentrations of α-tocopherol. The OI values do not show a significant trend; they are slightly higher toward the right-hand side of the plot, where the virgin UHMWPE region was initially, but overall they are small, much like the value in FIG. 6A for the annealed sample. Perhaps the most significant result is that oxidation of the UHMWPE does not occur in the regions containing α-tocopherol, even after accelerated aging.

Figure 7:
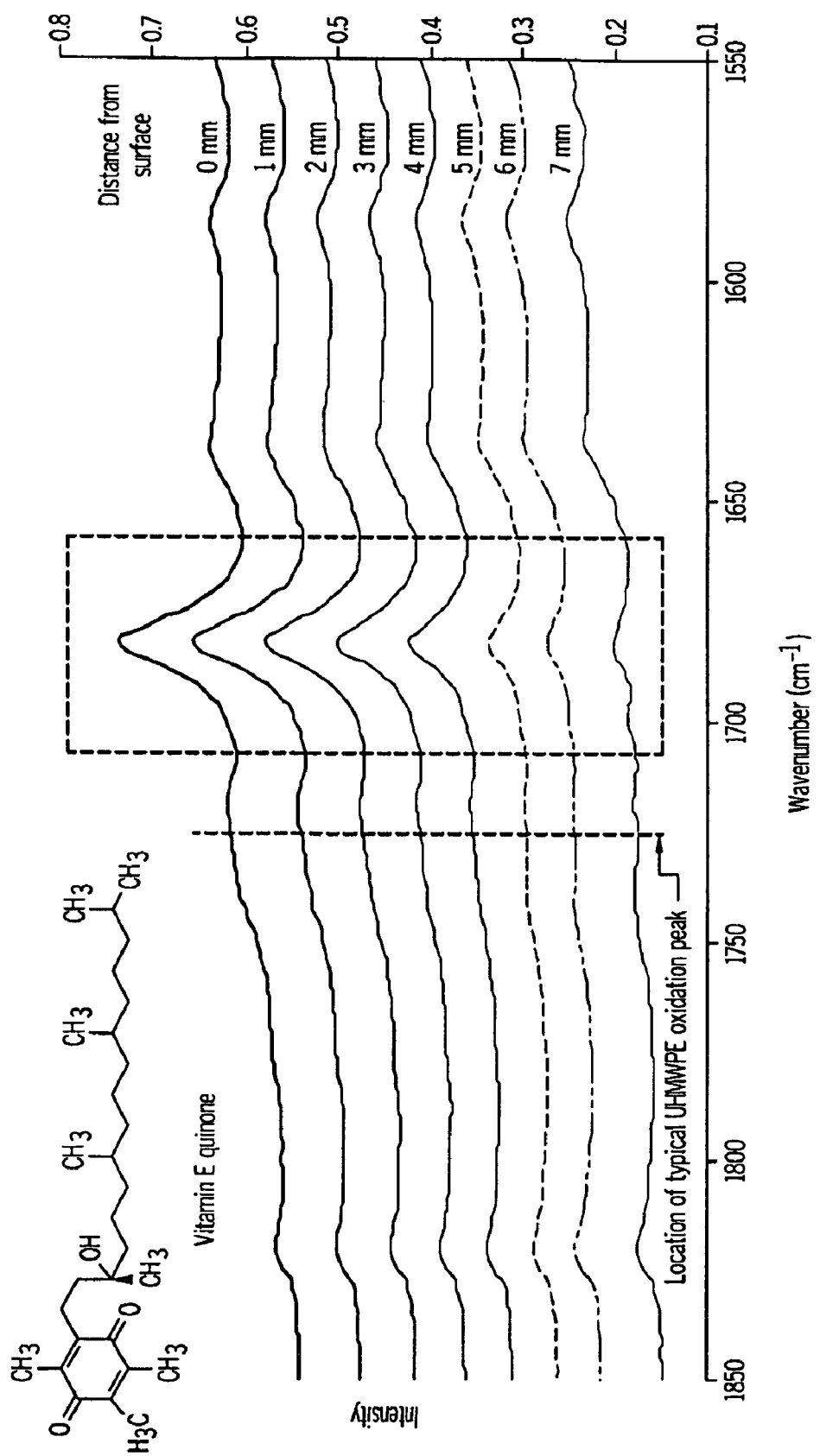
FIG. 7 illustrates the peak associated with Vitamin E quinone at 1680 $cm^{-1}$ as a function of depth.

In FIG. 7, FTIR spectra for the 1.5" annealed sample after aging are plotted to show the size of the quinone peak as a function of depth. One can see a monotonic trend in the size of the peak, as distance into the sample is increased. It is also apparent that the typical oxidation peak for UHMWPE (1730 $cm^{-1}$) is not significant, definitively showing the efficacy of α-tocopherol stabilization of UHMWPE.

Pin-on-disk wear test data for aged pins after 0.5 million cycles are shown in Table 1. Data for the sample annealed at 130° C. and the sample that was doped and homogenized are shown. An additional sample, which was annealed at 145° C., followed by aging, is also shown. Overall, the wear rates are relatively similar, with the values close to a weight loss of 2 mg/MC. These values are comparable to what is observed in highly cross-linked UHMWPE without α-tocopherol (S. M. Kurtz; O.K. Muratoglu; M. Evans; A. A. Eddin, "Advances in the processing, sterilization, and cross-linking of ultra-high molecular weight polyethylene for total joint arthroplasty", Biomaterials, 20 (1999) 1659-1688).

TABLE 1

| Pin-on-disk wear data for aged pins after 0.5 million cycles | | |
| --- | --- | --- |
| Processing steps | Weight Loss | Projected Wear Rate |
| Annealed at 130° C. | −0.80 mg | −1.60 mg/MC |
| Doped and homogenized | −0.90 mg | −1.80 mg/MC |
| Melt-annealed at 145° C. | −1.03 mg | −2.06 mg/MC |

Example 2

DCM of Acetabular Component with Wear-Resistant Bearing Surface and Tough Interior An acetabular shell of a porous metal such as tantalum, titanium, or other, or a non-porous metal, is used. GUR 1050 UHMWPE powder blended with α-tocopherol is fully consolidated or partially consolidated into the metal shell. UHMWPE diffusion into the metal is self-limiting. Other UHMWPE resins such as GUR 1020 are also used. The concentration of α-tocopherol in the powder blend is between about 0.005 and about 20 wt %, preferably between 0.05 and 5.0 wt %, preferably about 0.3 wt %, preferably about 0.5 wt %, or preferably about 1 wt %. The plunger used to pack the blended powder into the metal component is large enough to allow additional powder to be added in a second consolidation process, during which virgin GUR 1050 powder or GUR1050 with low amount of vitamin E is added over the blended GUR 1050 layer already in the shell. The second consolidation process is then performed using a plunger that is smaller than the final cup size of the component. The time of consolidation and the thickness of the virgin UHMWPE layer are controlled so that the thickness of the virgin layer is between about 0.1 mm and 10 mm, preferably 1 mm, preferably 2 mm, preferably 3 mm, or preferably 5 mm, or preferably more than 10 mm.

The fully consolidated component is irradiated using ionizing radiation such as gamma, electron-beam, or x-ray to a dose level between about 1 and about 10,000 kGy, preferably 25 to 200 kGy, preferably 50 to 150 kGy, preferably 65 kGy, preferably 85 kGy, or preferably 100 kGy. The irradiated acetabular component is then doped with α-tocopherol by placing the component in an α-tocopherol bath at room temperature or at an elevated temperature for a given amount of time, followed by a homogenization step under inert gas at room temperature or at an elevated temperature for a given amount of time. Table 2 is a list of preferred doping and homogenization times for select virgin UHMWPE layer thicknesses doped and homogenized at T=120° C. At higher temperatures the doping times are shorter and the homogenization times are shorter as well. Doping and homogenization times are longer if more α-tocopherol is desirable to have in the polyethylene.

After doping/homogenization, the UHMWPE is machined to its final shape. The machining is done in such a way that the thickness of the wear-resistant cross-linked UHMWPE layer at the acetabular cup surface is at least 0.1 mm, at least 0.2 mm, at least 1 mm, at least 2 mm, or at least 5 mm. The thickness of the uncross-linked, tough bulk layer is at least 0.5 mm, at least 1 mm, at least 2 mm, at least 5 mm, at least 10 mm, or at least 15 mm.

The finished component is then packaged under inert gas or under vacuum and subjected to sterilization. Sterilization is performed using ionizing radiation such as gamma, electron-beam, or x-ray to a dose level between 1 and 1000 kGy, preferably 10 to 200 kGy, preferably 25 kGy, preferably 40 kGy, or preferably 50 kGy. Alternatively the implant is packaged with gas permeable packaging and sterilized using a gas such as ethylene oxide or gas plasma.

TABLE 2

Doping and homogenization times for different virgin UHMWPE layer thickness. (For doping and homogenization performed at 120° C.)

| Thickness of virgin layer (mm) | Doping time (hr) | Homogenization time (hr) |
|---|---|---|
| 1 | 0.17 | 4 |
| 3 | 0.33 | 9 |
| 6 | 2.5 | 40 |
| 9 | 3 | 45 |

Example 3

DCM of Tibial Component with Wear-Resistant Bearing Surface and Tough Interior

A tibial base plate made from a porous metal such as tantalum, titanium, or other, or a non-porous metal, is used. GUR 1050 UHMWPE powder blended with α-tocopherol is fully consolidated or partially consolidated onto the base plate. UHMWPE diffusion into the porous metal is self-limiting. Other UHMWPE resins such as GUR 1020 are also used. The concentration of α-tocopherol in the powder blend is between about 0.005 and about 20 wt %, preferably between 0.05 and 5.0 wt %, preferably about 0.3 wt %, preferably about 0.5 wt %, or preferably about 1 wt %. Virgin GUR 1050 powder or GUR1050 powder blended with low amount of vitamin E is then added over the blended GUR 1050 layer already present. A second consolidation process is then performed using to produce a total UHMWPE layer that is larger the final UHMWPE thickness in the finished component. The time of consolidation and the thickness of the virgin UHMWPE layer is controlled so that the thickness of the virgin layer is between about 0.1 mm and 10 mm, preferably 1 mm, preferably 2 mm, preferably 3 mm, or preferably 5 mm, or preferably more than 10 mm.

The fully consolidated component is irradiated using ionizing radiation such as gamma, electron-beam, or x-ray to a dose level between 1 and 10,000 kGy, preferably 25 to 200 kGy, preferably 50 to 150 kGy, preferably 65 kGy, preferably 85 kGy, or preferably 100 kGy. The irradiated tibial component is then doped with α-tocopherol by placing the component in an α-tocopherol bath at room temperature or at an elevated temperature for a given amount of time, followed by a homogenization step under inert gas at room temperature or at an elevated temperature for a given amount of time. Table 1 is a list of preferred doping and homogenization times for select virgin UHMWPE layer thicknesses doped and homogenized at T=120° C. At higher temperatures the doping times are shorter and the homogenization times are shorter as well. Doping and homogenization times are longer if more α-tocopherol is desirable to have in the polyethylene.

After doping/homogenization, the UHMWPE is machined to its final shape. The machining is done in such a way that the thickness of the wear-resistant cross-linked UHMWPE layer at the articular surface of the tibial component is at least 0.1 mm, at least 0.2 mm, at least 1 mm, at least 2 mm, or at least 5 mm. The thickness of the uncross-linked, tough bulk layer is at least 0.5 mm, at least 1 mm, at least 2 mm, at least 5 mm, at least 10 mm, at least 15 mm, or at least 25 mm.

The finished component is then packaged under inert gas or under vacuum and subjected to sterilization. Sterilization is performed using ionizing radiation such as gamma, electron-beam, or x-ray to a dose level between 1 and 1000 kGy, preferably 10 to 200 kGy, preferably 25 kGy, preferably 40 kGy, or preferably 50 kGy. Alternatively the implant is packaged with gas permeable packaging and sterilized using a gas such as ethylene oxide or gas plasma.

Example 4

Consolidation of UHMWPE/Vitamin E in Anoxic Environment

α-tocopherol is dissolved in ethanol to create a solution. GUR1050 polyethylene resin is degassed either in vacuum or is kept in an anoxic environment to substantially remove the dissolved oxygen. The α-tocopherol-ethanol solution is then dry-blended with GUR1050 polyethylene resin. Two batches are prepared, one with degassed GUR1050 and the other with the as-received GUR1050 polyethylene resin. The dry-blended mixtures are then separately consolidated on a Carver laboratory bench press. Consolidation can be carried out in an anoxic environment to minimize the discoloration of the consolidated stock.

Example 5

Cross-Link Density of Blended and Irradiated UHMWPE (2003)

GUR 1050 powder was blended with α-tocopherol and consolidated. Consolidated GUR 1050 UHMWPE powder (consolidated without α-tocopherol) was used as virgin (control) material. The concentrations at which α-tocopherol was incorporated in the UHMWPE were 0.02, 0.05, 0.1, 0.3 and 1.0 wt/wt %. The blends were first prepared in 5 wt % for consistency, after which they were diluted down to their respective concentrations by adding UHMWPE powder. The molded blocks containing 0.1, 0.3 and 1.0 wt % were packaged under vacuum and γ-irradiated to 25, 65, 100, 150 and 200 kGy and the molded blocks containing 0.02 and 0.05 wt % were packaged and γ-irradiated to 150 and 200 kGy.

Cross-link density measurements were performed with a thermal mechanical analyzer (TMA) (DMA 7e, Perkin Elmer, Wellesley, Mass.). Thin sections were machined out of virgin, and α-tocopherol-blended and irradiated UHMWPE (thickness 3.2 mm). These thin sections were melted at 170° C. under flowing nitrogen to remove residual stresses from the consolidation process that might result in additional swelling. Small sections were cut out by razor blade from these thin sections to be analyzed (approximately 3 mm by 3 mm). These small pieces were placed under the quartz probe of the TMA and the initial height of the sample was recorded. Then, the probe was immersed in xylene, which was subsequently heated to 130° C. and held for at least 100 minutes. The UHMWPE samples swelled in hot xylene until equilibrium was reached. The final height was recorded. The cross-link density of the blends was calculated as described previously (see Muratoglu et al., *Unified Wear Model for Highly Crosslinked Ultra-high Molecular Weight Polyethylenes* (*UHMWPE*). *Biomaterials*, 1999. 20(16): p. 1463-1470) and are reported as mol/m$^3$.

Figure 8:
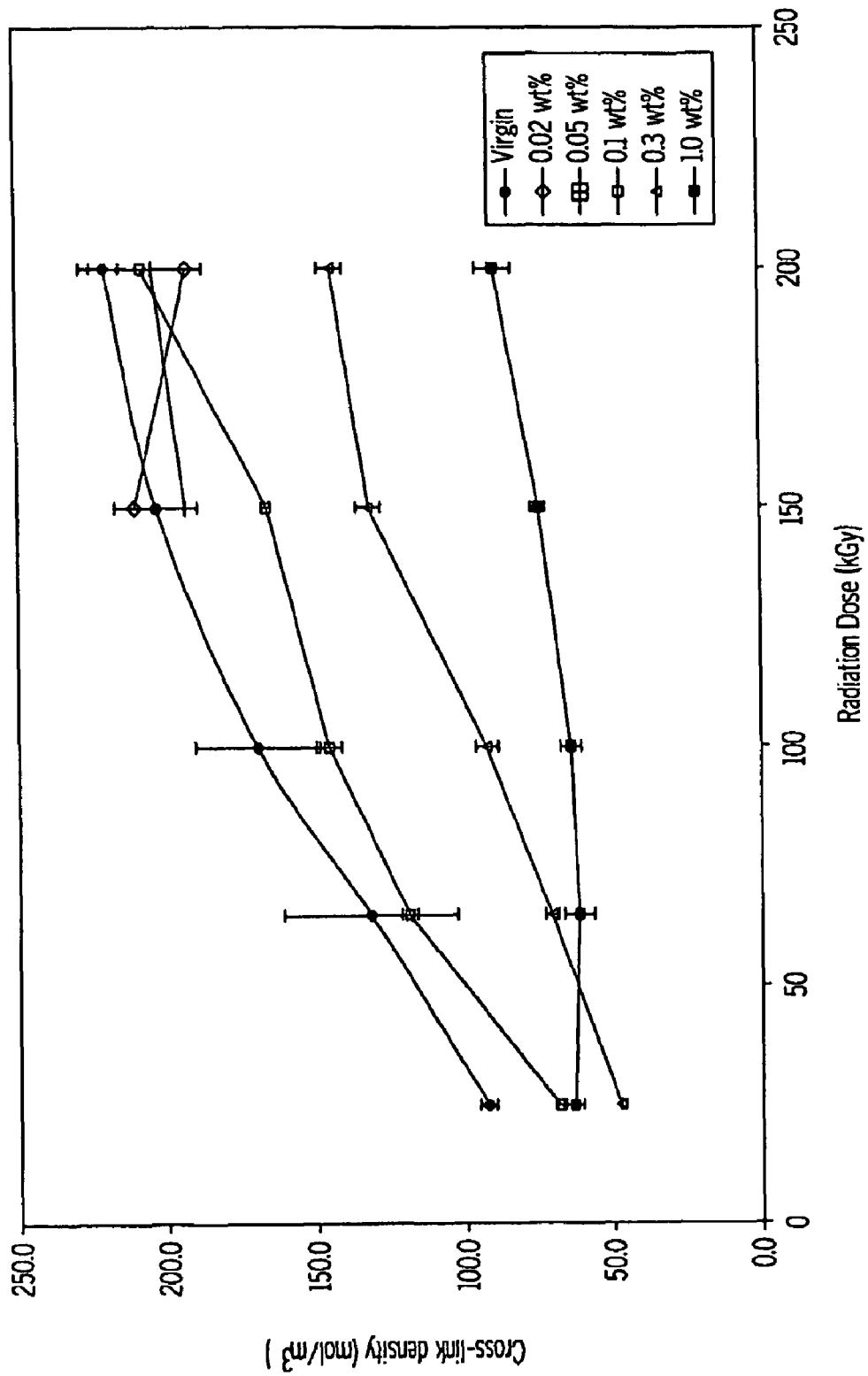
FIG. 8 shows the cross-link density of vitamin E-blended and subsequently irradiated UHMWPE as a function of radiation dose and vitamin E concentration.

The cross-link density of these virgin and blended and subsequently irradiated UHMWPE are shown in FIG. 8. These results show clearly that increasing vitamin E concentration decreases cross-linking in UHMWPE when present during irradiation. It also showed that at 0.05 wt %, the presence of vitamin E did not significantly affect cross-linking at 150 and 200 kGy compared to virgin UHMWPE (p=0.6 and 0.3, respectively). Since wear rate is dependent on cross-link density, the wear rate of this UHMWPE would be expected to be similar to virgin, irradiated UHMWPE.

Example 6

Wear Rate of Blended and Irradiated UHMWPE

GUR 1050 powder was blended with α-tocopherol and consolidated. Consolidated GUR 1050 UHMWPE powder (consolidated without α-tocopherol) was used as virgin (control) material. The concentrations at which α-tocopherol was incorporated in the UHMWPE were 0.1, and 0.3 wt/wt %. The blends were first prepared in 5 wt % for consistency, after which they were diluted down to their respective concentrations by adding UHMWPE powder. These molded blocks were packaged and γ-irradiated to 100 kGy.

Three cylindrical samples (9 mm in diameter and 13 mm in length) out of each of the three irradiated blocks (virgin, 0.1%, and 0.3 wt %) were used for POD wear testing. These pins were accelerated aged at 80° C. in air for 5 weeks and tested on a bi-directional POD tester at a frequency of 2 Hz for 2 million cycles with gravimetric assessment of wear at every 0.5 million cycles. Undiluted bovine serum was used as lubricant with 0.3 wt % sodium azide as antibacterial agent and 1 mM EDTA as chelating agent. The wear rate was determined by linear regression of the weight change of each pin over number of cycles from 0.5 to 2 million cycles.

The pin-on-disc (POD) wear rates of 0.1 and 0.3 wt % blended and irradiated UHMWPE were both higher than the wear rates that were published for 100-kGy irradiated and melted UHMWPE (see Muratoglu et al., *Effect of Radiation, Heat, and Aging on In Vitro Wear Resistance of Polyethylene. Clinical Orthopaedics & Related Research*, 2003. 417: p. 253-262). The in vitro wear rates obtained from POD testing for 0.1 and 0.3 wt % α-tocopherol-blended, and 100-kGy irradiated UHMWPE following accelerated aging were 2.10±0.17 and 5.01±0.76 mg/million cycle (MC), respectively. The wear rate for the 0.3 wt % blended UHMWPE was higher than that for 0.1 wt % blended UHMWPE (p=0.018).

Example 7

Mechanical Properties of Blended and Irradiated UHMWPE as a Function of Vitamin E Concentration and Radiation Dose GUR 1050 powder was blended with α-tocopherol and consolidated. Consolidated GUR 1050 UHMWPE powder (consolidated without α-tocopherol) was used as virgin (control) material. The concentrations at which α-tocopherol was incorporated in the UHMWPE were 0.02, 0.05, 0.1, 0.3 and 1.0 wt/wt %. The blends were first prepared in 5 wt % for consistency, after which they were diluted down to their respective concentrations by adding UHMWPE powder. The molded blocks containing 0.1, 0.3 and 1.0 wt % were packaged under vacuum and γ-irradiated to 25, 65, 100, 150 and 200 kGy.

Dog-bone shaped specimens (n=5 each) were stamped from virgin, 0.1 and 0.3 wt % α-tocopherol-blended and irradiated UHMWPE in accordance with ASTM D638, standard test method for tensile properties of plastics. These samples were then tested in accordance with ASTM D-638 using a MTS II machine (Eden Prarie, Minn.) at a crosshead speed of 10 mm/min.

Figure 9A:
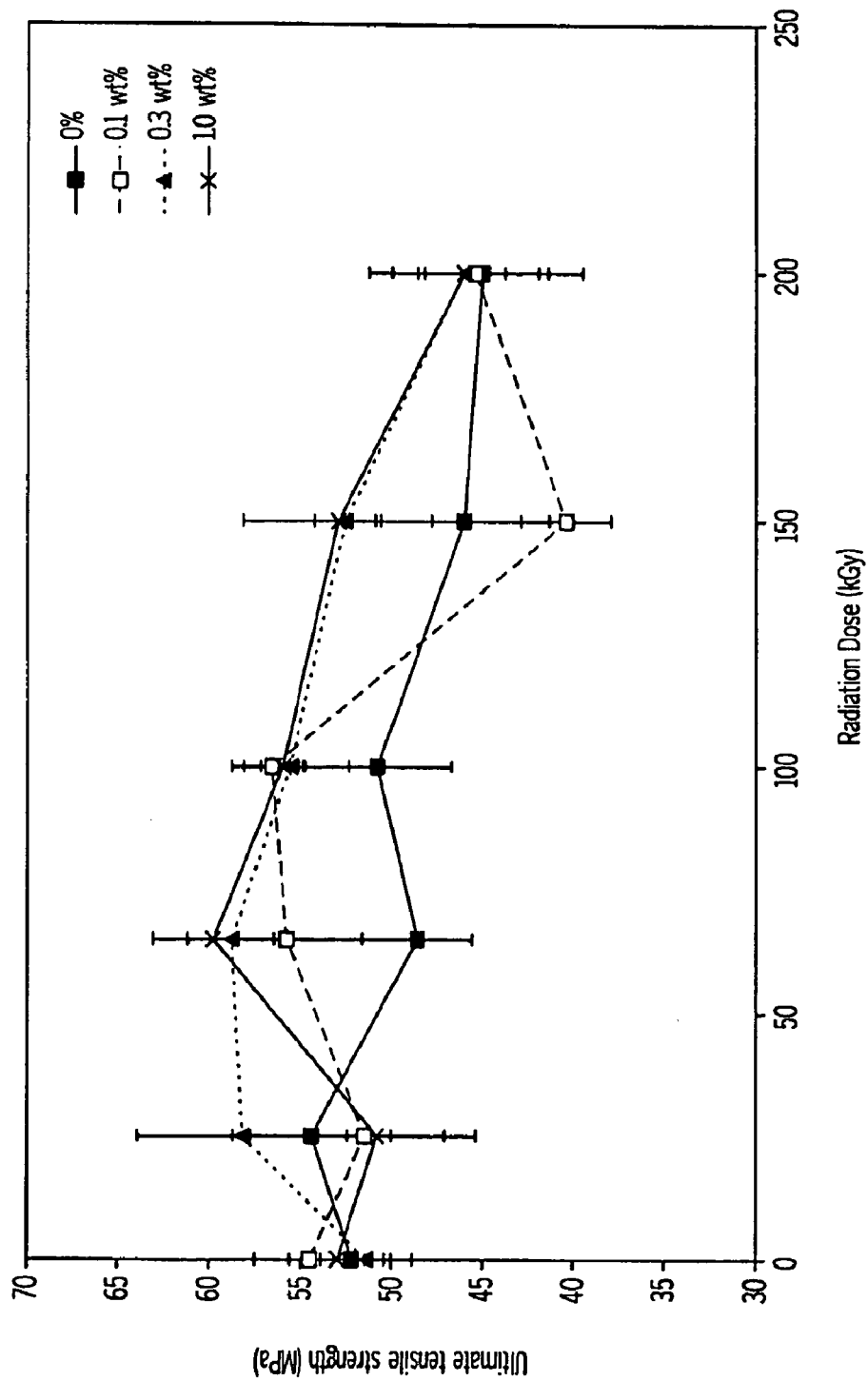
FIG. 9 shows the ultimate tensile strength (UTS) (9A), elongation-at-break (EAB) (9B), and work-to-failure (WF) (9C) of vitamin E blended and subsequently irradiated UHMWPE as a function of radiation dose and vitamin E concentration.
Figure 9B:
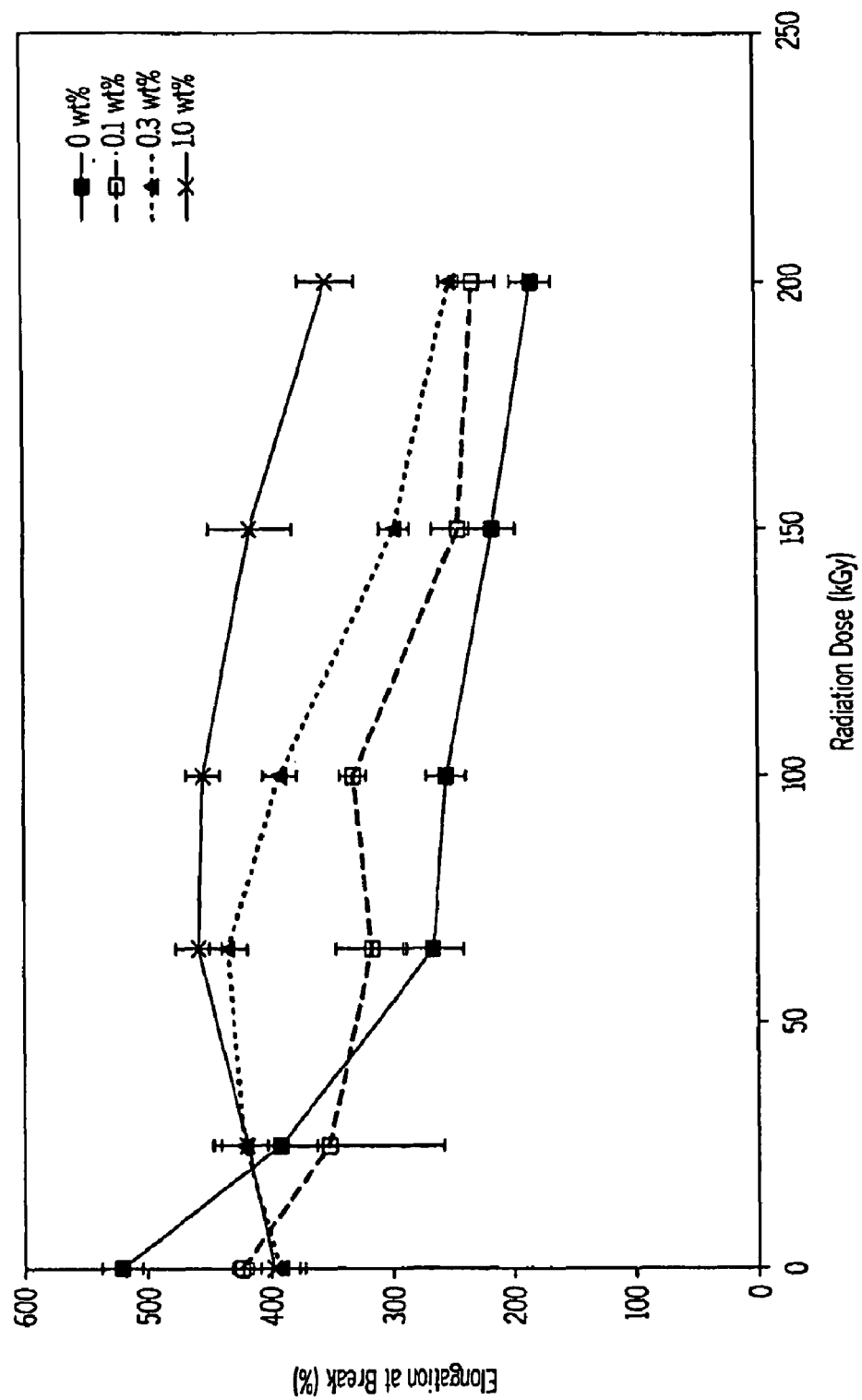
Figure 9C:
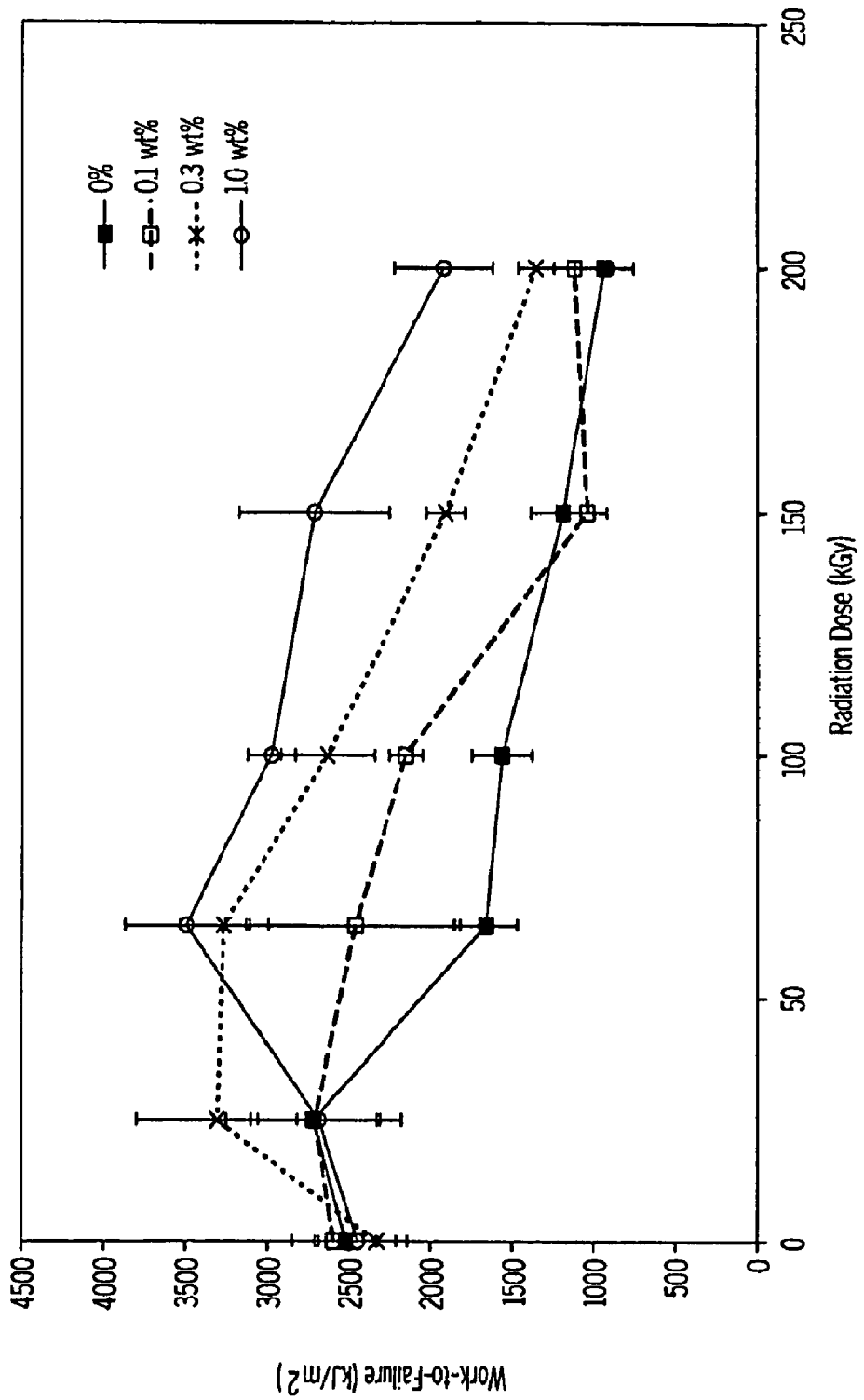

The mechanical strength of virgin UHMWPE (indicators are ultimate tensile strength (UTS), elongation at break (EAB) and work to failure (WF)) decreased with increasing radiation dose (FIGS. 9A, 9B, and 9C). In contrast, these indicators stayed the same or increased with increasing radiation dose until about 100 kGy irradiation for vitamin E-blended and irradiated UHMWPEs. These results suggested that the presence of vitamin E during irradiation not only decreased cross-linking but also increased the scissioning of polyethylene chains. This resulted in higher elongation-to-break than the virgin UHMWPEs.

These results further suggested that the mechanical properties of UHMWPE can be manipulated by the presence and concentration of vitamin E in UHMWPE during the irradiation as well as the radiation dose.

Example 8

Gradient Cross-Linking by Irradiating Vitamin E-Doped Conventional UHMWPE

Cylinders (3 cm diameter, 3.75 cm length) were machined from slab compression molded GUR1050 UHMWPE.

A bath of vitamin E (D,L-α-tocopherol) was heated to 170° C. One cylinder of UHMWPE was placed in the vitamin E bath and kept for 15 minutes. During this time, the surface of the cylinder (about 2-3 mm) became transparent, showing melting at the surface. In this way, the surface of the UHMWPE block was doped with vitamin E in the melt phase, enhancing the diffusion rate above that which would occur at below the melting point (approximately 137° C.).

The block was packaged in vacuum after doping and irradiated by gamma irradiation to 100 kGy.

Fourier Transform Infrared Spectroscopy (FTIR) was performed on thin sections (approximately 150 μm) cut using a sledge microtome. Infrared spectra were collected from one edge of the sample to the other in 100 μm and 500 μm intervals, with each spectrum recorded as an average of 32 individual scans. The infrared spectra were analyzed to calculate a vitamin E index as the ratio of the areas under the α-tocopherol absorbance at 1262 cm$^{-1}$ (1245-1275 cm$^{-1}$) and the polyethylene skeletal absorbance at 1895 cm$^{-1}$ (1850-1985 cm$^{-1}$). The vitamin E index was plotted as a function of distance away from the surface to present the vitamin E concentration profiles of the doped samples.

Likewise, a transvinylene index (TVI) was calculated as the ratio of the areas under the transvinylene absorbance at 965 cm$^{-1}$ and the polyethylene skeletal absorbance at 1895 cm$^{-1}$ (1850-1985 cm$^{-1}$). TVI has been shown to increase with increasing radiation dose and is about 0.12-0.15 for a virgin, 100-kGy irradiated UHMWPE.

Figure 10:
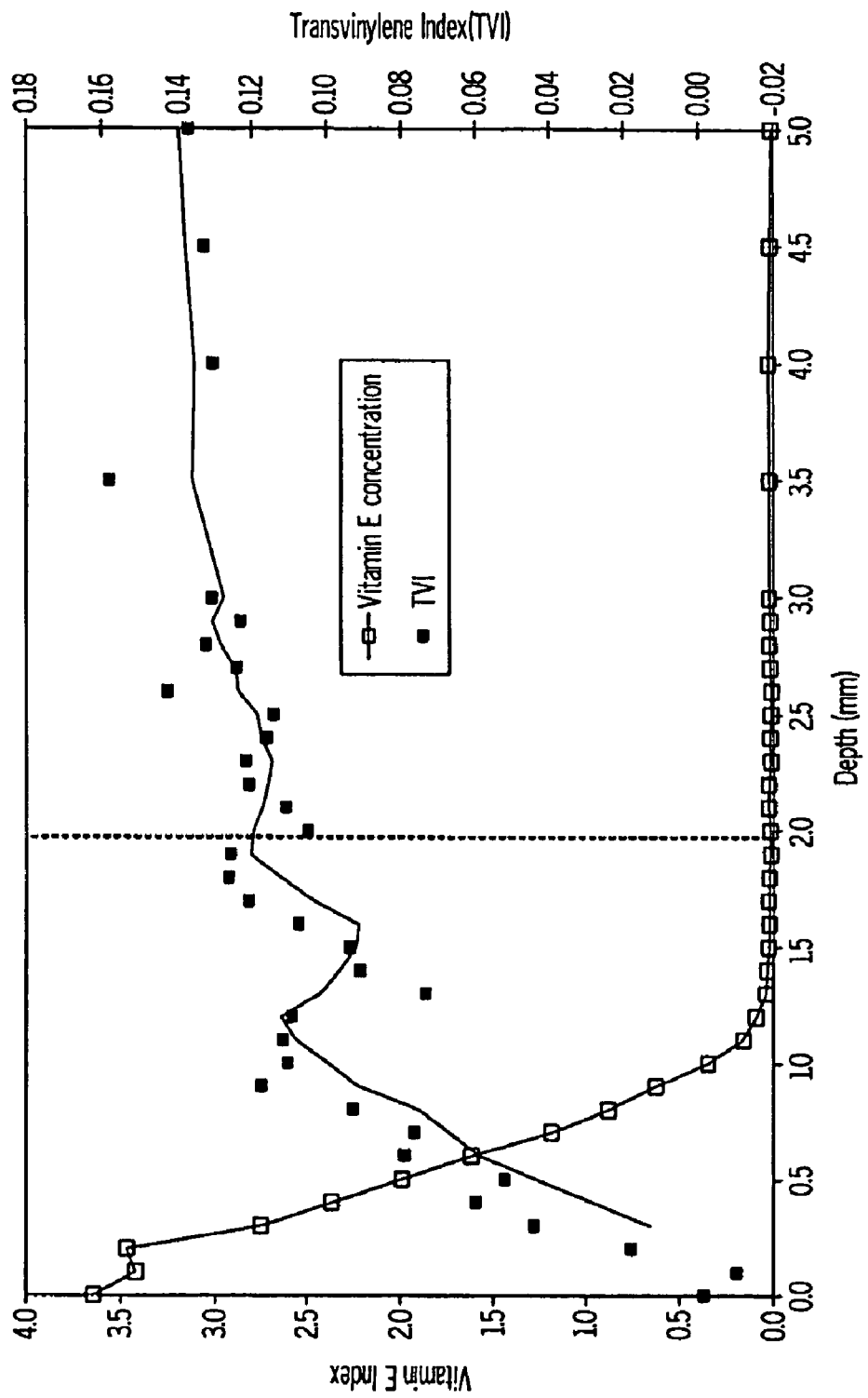
FIG. 10 shows vitamin E index and transvinylene index (TVI) of UHMWPE doped with vitamin E and subsequently irradiated. The graph shows the concentration profile before irradiation and TVI profile after 100-kGy irradiation of a GUR1050 UHMWPE block, whose surface was doped for 15 minutes by placing in a vitamin E bath at 170° C.

The vitamin E concentration profile of the block before irradiation and the transvinylene groups after irradiation are shown as a function of depth from the surface in FIG. 10.

Vitamin E inhibited cross-linking in doped UHMWPE, as shown by the decrease in TVI in the vitamin E-rich surface region of the doped, then irradiated UHMPE block. Vitamin E penetration, defined as an index level of 0.02 was until about 2 mm into the sample and the TVI reached those observed for a virgin UHMWPE at about 2-3.0 mm.

These results show that the cross-link density of a UHMWPE can be manipulated by the presence of diffused vitamin E.

Similarly, one cylinder was doped in a vitamin E bath at 132° C. below the melting point of UHMWPE for 4 hours and subsequently irradiated by gamma irradiation to 100 kGy.

Example 9

Mechanical Properties of Doped UHMWPE with Subsequent Cold Irradiation, and Cold Irradiation and Melting Consolidated GUR 1050 (3" diameter) was machined into thin sections (3.2 mm thickness). These samples were then doped with vitamin E (D,L-α-tocopherol) in 0.5 atm partial nitrogen/vacuum at 132° C. Following doping, they were taken out of vitamin E, wiped clean with ethanol to remove excess, and placed in 0.5 atm partial nitrogen/vacuum at 132° C. for homogenization. Doping and homogenization conditions of the four study groups are shown in Table 3 as well as the average vitamin E index levels along the sample depth. The vitamin E index was determined by using FTIR spectroscopy as described in Example 8.

TABLE 3

Processing parameters and amount of α-tocopherol in samples I-IV.

| Sample ID | Doping Temperature (° C.) | Doping Duration (h) | Homogenization Temperature (° C.) | Homogenization Duration (h) | Average vitamin E index |
|---|---|---|---|---|---|
| I | 132 | 5 | 132 | 48 | 0.92 ± 0.10 |
| II | 132 | 24 | 132 | 48 | 1.98 ± 0.07 |
| III | 132 | 48 | 132 | 72 | 3.80 ± 0.13 |
| IV | 132 | 96 | 132 | 96 | 4.62 ± 0.12 |

Subsequent to doping and homogenization, thin sections were processed in the following manner.
1. No irradiation.
2. Cold e-beam irradiation to 100 kGy in air.
3. Cold e-beam irradiation to 100 kGy in air with subsequent melting at 155° C.

Two other controls used in this study were previously tested 100 kGy γ-irradiated in N$_2$ GUR 1050 (CI) and 100 kGy e-beam irradiated in N$_2$ GUR 1050 (CISM). Electron beam irradiation was performed at the High Voltage Laboratories at Massachusetts Institute of Technology (Cambridge, Mass.) using a 2.5 MeV Van de Graff generator.

For the doped/homogenized and irradiated samples, it was established that the profiles of α-tocopherol after irradiation were uniform by using FTIR spectroscopy.

Dog-bone shaped samples (n=5) were stamped out of the thin sections in accordance with ASTM D-638 Standard method for tensile properties of plastics. These tensile specimens were tested on a MTS II Machine (Eden Prarie, Minn.) at a crosshead speed of 10 mm/min until failure.

Some important mechanical properties of study materials are shown in Table 4.

TABLE 4

Mechanical properties of α-tocopherol doped test samples and controls.

| Sample | Vitamin E index before irradiation | UTS* (MPa) | Engineering Strain at Break (%) | YS (MPa) |
|---|---|---|---|---|
| Unirradiated | | | | |
| GUR 1050 | — | 54 ± 7 | 970 ± 66 | 23 ± 3 |
| 100 kGy irradiated (CI) | | | | |
| 100 kGy | — | 45 ± 1 | NA | 24 ± 1 |
| Vitamin E doped/not irradiated | | | | |
| I | 0.92 ± 0.10 | 59 ± 2 | 1107 ± 36 | 21.8 ± 0.4 |
| II | 1.98 ± 0.07 | 56 ± 2 | 1046 ± 43 | 21.2 ± 0.8 |
| III | 3.80 ± 0.13 | 54 ± 1 | 988 ± 24 | 20 ± 0 |
| IV | 4.62 ± 0.12 | 53 ± 1 | 953 ± 22 | 19 ± 0 |
| Vitamin E doped/100 kGy irradiated | | | | |
| I | 0.92 ± 0.10 | 53 ± 3 | 1072 ± 60 | 23 ± 0 |
| II | 1.98 ± 0.07 | 53 ± 4 | 1081 ± 87 | 22 ± 0.7 |
| III | 3.80 ± 0.13 | 48 ± 3 | 1013 ± 78 | 20.8 ± 0.4 |
| IV | 4.62 ± 0.12 | 48 ± 2 | 1058 ± 66 | 19.6 ± 0.5 |
| Vitamin E doped/100 kGy irradiated/melted | | | | |
| I | 0.92 ± 0.10 | 59 ± 2 | 1505 ± 87 | 21 ± 0 |
| II | 1.98 ± 0.07 | 54 ± 4 | 1493 ± 136 | 19.6 ± 0.5 |
| III | 3.80 ± 0.13 | 50 ± 3 | 1397 ± 94 | 18.8 ± 0.4 |
| IV | 4.62 ± 0.12 | 50 ± 5 | 1440 ± 162 | 18.8 ± 0.4 |

*UTS: Ultimate tensile strength, EAB: Elongation at break, YS: Yield strength.

The effect of irradiation alone was observed by comparing unirradiated and 100 kGy irradiated UHMWPE. While the yield strength remains similar, all mechanical properties were decreased as a result of irradiation to this high dose level. Doped/not irradiated UHMWPE was compared to unirradiated UHMWPE to observe the effect of vitamin E on unirradiated UHMWPE. The engineering strain at break, which is an indicator of plasticity was similar to that of unirradiated GUR 1050 (p>0.05).

All mechanical properties of doped/irradiated UHMWPE have higher values than that for irradiated material. The engineering strain is especially significant showing that doped/irradiated UHMWPE shows higher plasticity than irradiated UHMWPE.

The engineering strain for doped/irradiated/melted UHMWPE was significantly higher than that for irradiated/melted samples (p<0.0001).

Example 10

Mechanical Properties of Vitamin E-Containing UHMWPE with Subsequent Melt-Irradiation Consolidated GUR 1050 (3" diameter) was machined into thin sections (3.2 mm thickness). These samples were then doped with vitamin E (D,L-α-tocopherol) in 0.5 atm partial nitrogen/vacuum at 132° C. Following doping, they were taken out of vitamin E, wiped clean with ethanol to remove excess, and placed in 0.5 atm partial nitrogen/vacuum at 132° C. for homogenization. Doping and homogenization conditions of the four study groups are shown in Table 3 as well as the average vitamin E index levels along the sample depth. The vitamin E index was determined by using FTIR spectroscopy as described in Example 8.

Then these samples were irradiated to 100-kGy by electron beam irradiation under flowing nitrogen (12.5 kGy/pass, HVRL, MIT, Cambridge, Mass.) at 180° C.

The mechanical properties of vitamin E-doped and melt irradiated UHMWPE are shown in Table 5. The elongation-at-break of doped and melt-irradiated UHMWPE was similar to that of virgin UHMWPE.

TABLE 5

Mechanical properties of vitamin E doped and melt-irradiated test samples and controls. EAB is the true elongation at break.

| Sample | Vitamin E index before irradiation | UTS* (MPa) | EAB (%) | YS (MPa) |
|---|---|---|---|---|
| Unirradiated | | | | |
| GUR 1050 | — | 54 ± 7 | 481 | 23 ± 3 |
| 100 kGy irradiated (CI) | | | | |
| 100 kGy | — | 45 ± 1 | | 24 ± 1 |
| Vitamin E doped/100 kGy melt-irradiated | | | | |
| I | 0.92 ± 0.10 | 40 ± 1 | 481 ± 7 | 20 ± 1 |
| II | 1.98 ± 0.07 | 42 ± 1 | 506 ± 16 | 20 ± 1 |
| III | 3.80 ± 0.13 | 40 ± 2 | 515 ± 24 | 18 ± 0 |
| IV | 4.62 ± 0.12 | 42 ± 4 | 507 ± 17 | 18 ± 0 |

Example 11

Mechanical Properties of Melt-Doped and Irradiated UHMWPE

Consolidated GUR 1050 (3" diameter) was machined into thin sections (3.2 mm thickness). These samples were then doped with vitamin E (D,L-α-tocopherol) in 0.5 atm partial nitrogen/vacuum at 170° C. for 22 hours. Following doping, they were taken out of vitamin E, wiped clean with ethanol to remove excess, and placed in 0.5 atm partial nitrogen/vacuum at 132° C. for homogenization for 48 hours.

TABLE 6

Mechanical properties of α-tocopherol doped test samples and controls.

| Sample | α-tocopherol index | UTS* (MPa) | Engineering Strain at Break (%) | Yield Strength (MPa) |
|---|---|---|---|---|
| Unirradiated | | | | |
| GUR 1050 | — | 54 ± 7 | 970 ± 66 | 23 ± 3 |
| 100 kGy irradiated (CI) | | | | |
| 100 kGy | — | 45 ± 1 | | 24 ± 1 |
| α-tocopherol doped/not irradiated | | | | |
| V | 12.7 ± 1.4 | 27 ± 7 | 1116 ± 88 | 10 ± 2 |
| α-tocopherol doped/100 kGy irradiated | | | | |
| V | 12.7 ± 1.4 | 27 ± 2 | 1174 ± 73 | 9 ± 1 |
| α-tocopherol doped/100 kGy irradiated/melted | | | | |
| V | 12.7 ± 1.4 | 24 ± 4 | 1406 ± 219 | 9 ± 1 |
| α-tocopherol doped/100 kGy melt irradiated | | | | |
| V | 12.7 ± 1.4 | 28 ± 3 | 1355 ± 256 | 12 ± 1 |

One such melt-doped and homogenized thin section was cold irradiated to 100 kGy by electron beam irradiation (2.5 MeV beam, 12.5 kGy/pass, HVRL, MIT, Cambridge, Mass.). One was cold irradiated to 100 kGy, then melted. And finally, one was irradiated to 100 kGy at 170° C.

The ultimate tensile strength of all melt-doped and processed UHMWPE were much lower than that of virgin and virgin irradiated UHMWPE (see Table 6). The results as shown in Table 6 suggest that melt-doping UHMWPE resulted in a UHMWPE with low strength and high plasticity. Further melting after irradiation increased the elongation further.

Example 12

Mechanical Properties of Cross-Linked, Vitamin E Diffused and Irradiated UHMWPE(2005)

Electron-beam irradiated UHMWPE (100-kGy; Unmelted Longevity) was machined into 3.2 mm-thick sections. These sections were doped with vitamin E at 120° C. for 20 minutes under argon and subsequently homogenized for 24 hours in argon. The resulting vitamin E profile was determined using Fourier Transform Infrared Spectroscopy. These thin sections were then irradiated to 65 and 100 kGy by electron beam irradiation (2.5 MeV Van-de-Graff generator (HVRL, Massachusetts Institute of Technology, Cambridge, Mass.) at a dose rate of 12.5 kGy/pass) or 100 and 200 kGy by gamma irradiation (Steris Isomedix, Northborough, Mass.). Dogbone shaped tensile specimens (Type V) were stamped out of these thin sections and they were tested per ASTM D638.

The average vitamin E index of 65-kGy irradiated, vitamin E-doped UHMWPE was 0.13. There were no appreciable changes in the mechanical properties of 100-kGy irradiated, vitamin E-doped UHMWPE with subsequent high dose irradiation (Table 7).

Example 13

Gradient Vitamin E Profile by Diffusion

Slab compression molded GUR1050 UHMWPE was packaged in aluminum foil packaging in vacuum and irradiated to 65 kGy using $^{60}$Co gamma irradiation (Steris Isomedix, Northbrough, Mass.). Unirradiated UHMWPE was used without irradiation.

Cubes of unirradiated, and 65 kGy irradiated UHMWPE (2 cm) were machined from the stock. Three cubes each were doped in vitamin E by soaking in the bath at 120° C., 2, 8 and 24 hours.

Figure 11A:
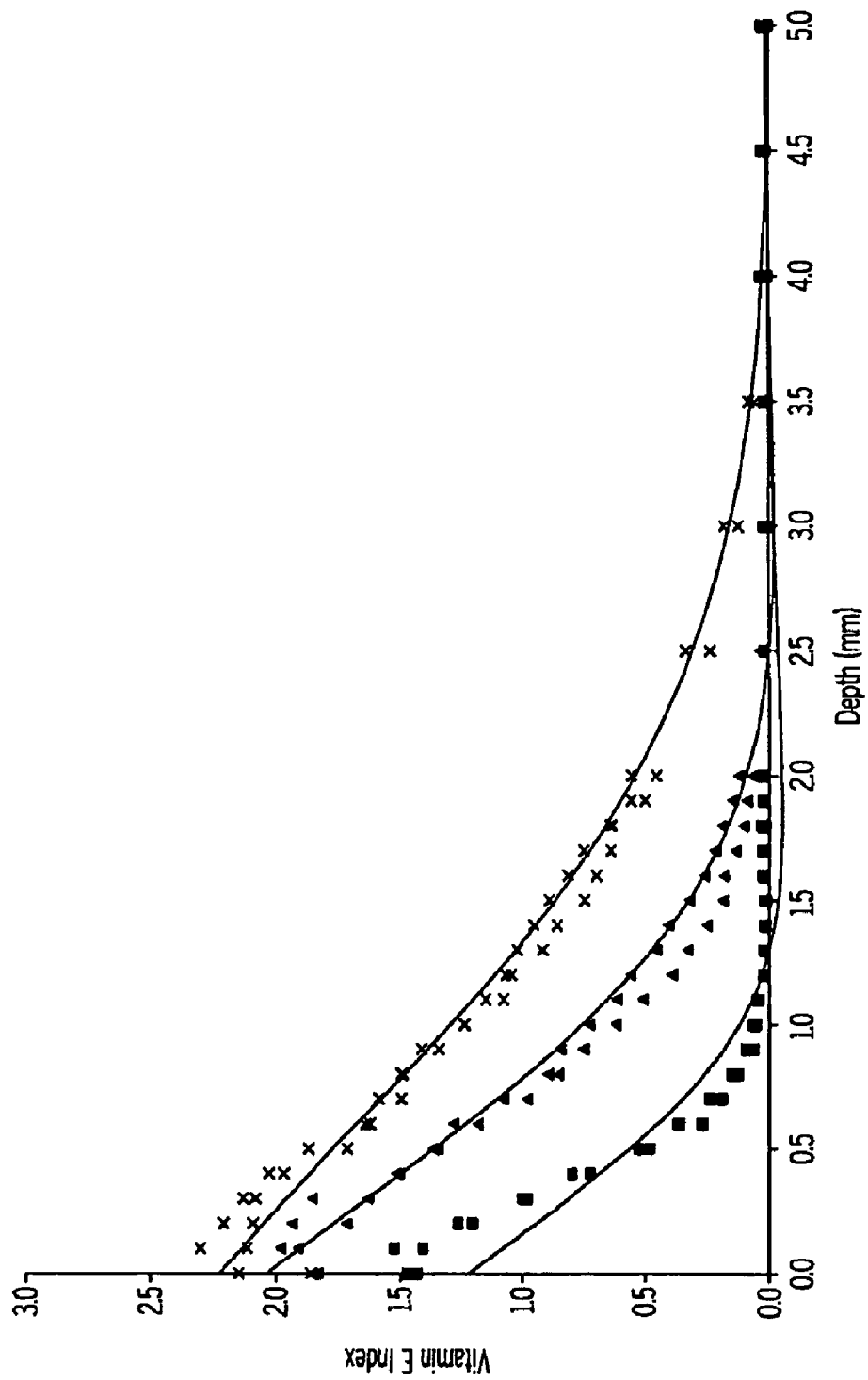
FIG. 11A shows vitamin E concentration profiles of unirradiated UHMWPE doped with vitamin E at 120° C. for 2, 8 and 24 hours.
Figure 11B:
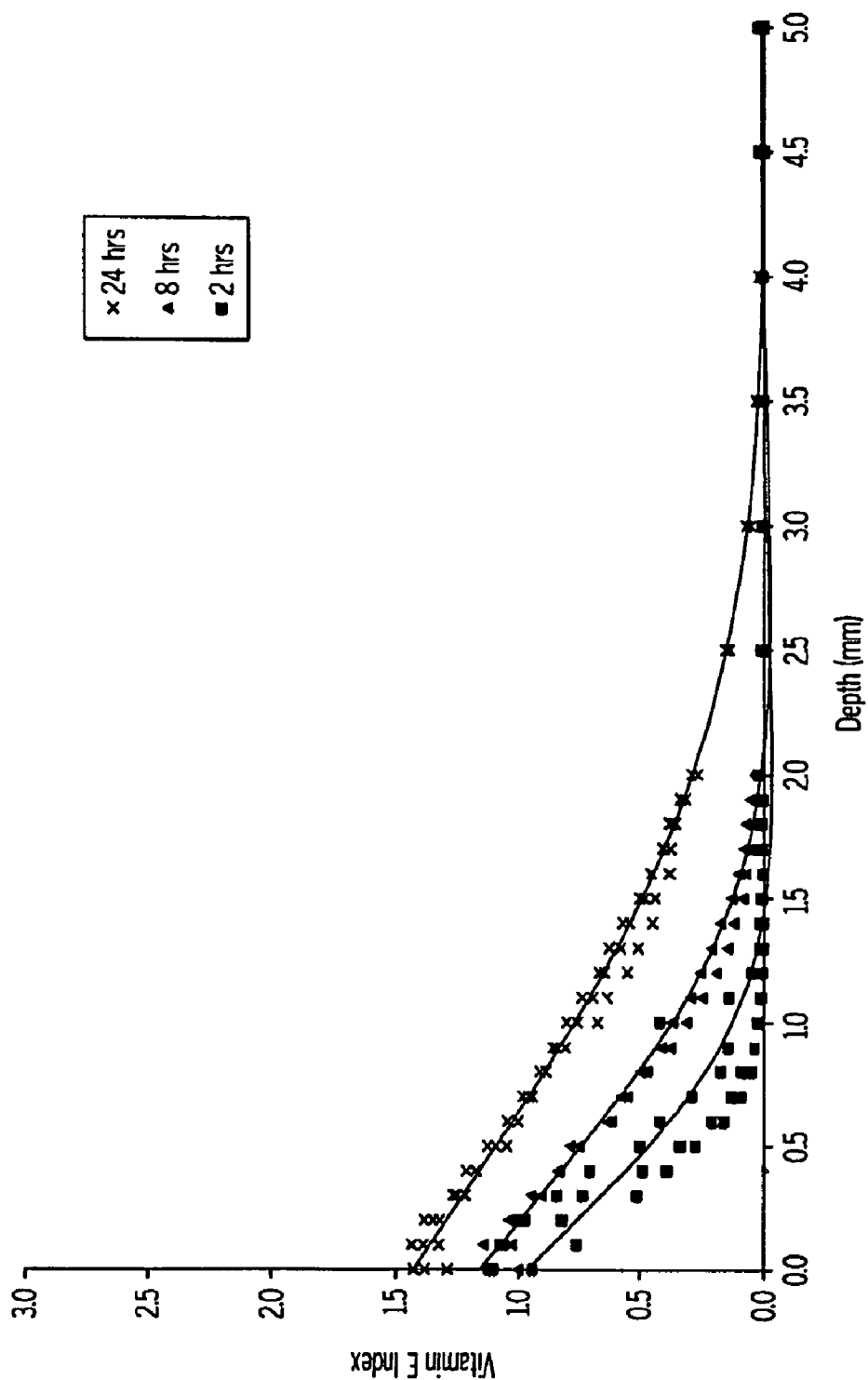
FIG. 11B shows Vitamin E concentration profiles of 65-kGy irradiated UHMWPE doped with vitamin E at 120° C. for 2, 8 and 24 hours.

Both surface concentration and penetration depth increased with increasing doping time. The overall weight gain due to vitamin E also increased as a function of doping time. The vitamin E concentration profiles are shown in FIGS. 11A and 11B. The vitamin E concentration showed a gradient from a vitamin E-rich surface to a vitamin E-poor bulk.

TABLE 7

Mechanical properties of cross-linked, vitamin E-diffused and high dose irradiated UHMWPEs.

| Sample | UTS range (MPa) | UTS (MPa) | YS (MPa) | WF (kJ/m$^2$) |
|---|---|---|---|---|
| 65 kGy | | 49 ± 3 | 22 ± 0 | 1663 ± 191 |
| 65 kGy + Vitamin E | | 39 ± 3 | 24 ± 1 | 1414 ± 178 |
| 65 kGy + Vitamin E + 65 kGy e-beam | | 42 ± 4 | 23 ± 1 | 1516 ± 304 |
| 65 kGy + Vitamin E + 100 kGy e-beam | | 42 ± 4 | 23 ± 2 | 1563 ± 226 |
| 100 kGy | | 46 ± 4 | 21 ± 1 | 1397 ± 211 |
| 100 kGy + Vitamin E | 33-45 | 40 ± 6 | 21 ± 2 | 1285 ± 287 |
| 100 kGy + Vitamin E + 100 kGy e-beam | 36-52 | 44 ± 7 | 22 ± 1 | 1318 ± 355 |
| 100 kGy + Vitamin E + 100 kGy gamma | 28-50 | 42 ± 9 | 24 ± 1 | 1242 ± 411 |
| 100 kGy + Vitamin E + 200 kGy gamma | 35-46 | 40 ± 9 | 25 ± 0 | 1131 ± 191 |

Example 14

Gradient and Uniform Vitamin E Profile by Doping and Homogenization

GUR1050 UHMWPE bar stock (thickness 4 cm) was irradiated to 100-kGy by e-beam irradiation (Iotron Inc., Vancouver, BC) under vacuum in foil packaging. Approximately 45×90×25 mm blocks were machined out of this irradiated stock. Two blocks was doped in vitamin E at 120° C. for 6 hours. Excess vitamin E was wiped from the surfaces. Subsequently, one was homogenized in argon for 50 hrs at 130° C. and the other was homogenized in argon for 216 hrs at 130° C.

Figure 12:
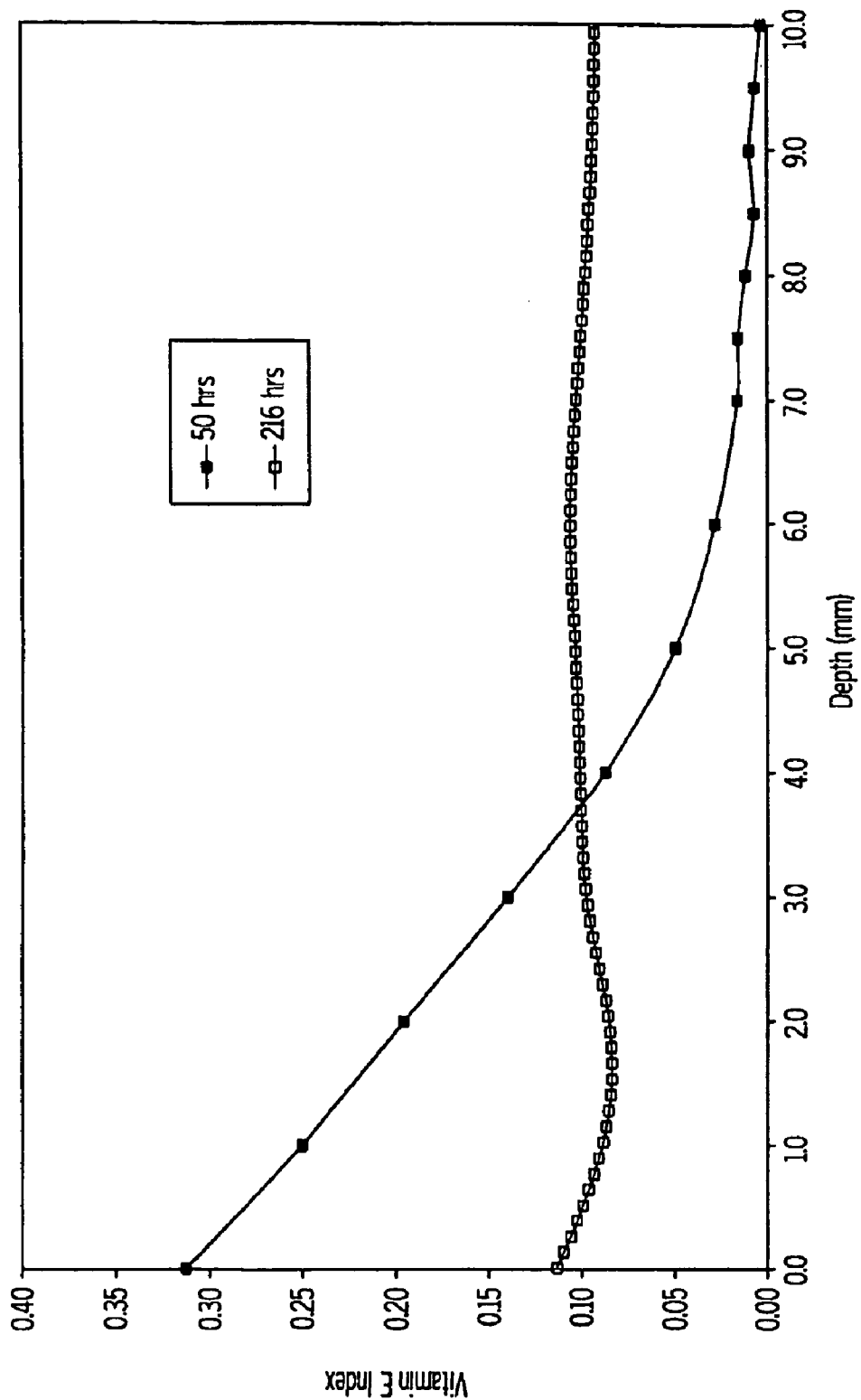
FIG. 12 illustrates vitamin E concentration profiles of 100-kGy irradiated UHMWPE doped at 120° C. for 6 hours and homogenized at 130° C. for 50 or 216 hours.

The vitamin E concentration profiles for these two doped and homogenized UHMWPEs are shown in FIG. 12. Homogenizing for 50 hrs resulted in a gradient vitamin E profile and homogenization for 216 hours resulted in a uniform profile.

Example 15

The Cross-Linking Density of Blended/Virgin Compression Molded and Irradiated Puck Two puck-shaped pieces of UHMWPE, both 2.5" in diameter, were direct compression molded (DCM). One puck was 1" thick, the other one was 1.5" thick. The 1" thick puck was produced using a standard molding cycle in which the bottom half of the mold was filled with GUR 1050 powder containing 0.5 wt % α-tocopherol and the top half with virgin GUR 1050 powder. The 1.5" thick puck was produced using a modified molding cycle, in which the bottom half of the mold was filled with GUR 1050 powder containing 0.5 wt % α-tocopherol and compressed at room temperature under a pressure of 1220 psi. Following release of the pressure, the top half of the mold was filled with virgin GUR 1050 powder followed by a standard DCM cycle. The pucks were subjected to 100-kGy e-beam irradiation at 5 kGy/pass at about room temperature.

A 3 mm-thick sample (approximately 3 mm by 3 mm in crossection) was cut from the virgin UHMWPE surface and a similar sample was cut from the core of the blended UHMWPE bulk after irradiation. These samples were tested on a swell ratio tester by injecting xylene at 130° C. into a chamber where the sample height is recorded prior to injection and continuously while the sample swells in hot xylene. The cross-link density of the irradiated samples was calculated as described previously (see Muratoglu et al., *Unified Wear Model for Highly Crosslinked Ultra-high Molecular Weight Polyethylenes (UHMWPE). Biomaterials*, 1999. 20(16): p. 1463-1470) and are reported as mol/m$^3$.

The cross-link density of the highly cross-linked virgin UHMWPE taken from the surface was 271 mol/m$^3$ and the low cross-linked blended UHMWPE taken from the bulk was 84 mol/m$^3$.

Example 16

Elimination of Free Radicals in Irradiated UHMWPE by High Pressure Crystallization or High Pressure Annealing Six blocks (approximately 1.5 by 1.5 in, 2 in thickness) of GUR1050 UHMWPE were machined from 65- and 100-kGy irradiated stock. One block of each stock were separately high pressure annealed by pressurizing in a high pressure chamber to 55,000 psi and heating to 200° C. and 220° C. to transition into the hexagonal phase from the solid orthorhombic phase. They were also separately high pressure crystallized by heating first to 200° C., then pressurizing to 55,000 psi to transition into the hexagonal phase from the melt phase. Two blocks without high pressure crystallization or annealing were used as controls.

Small samples (approximately 3 by 3 mm in cross-section, 2 cm in length) were tested for electron spin resonance measurements to determine the amount of free radicals in the samples.

Figure 13A:
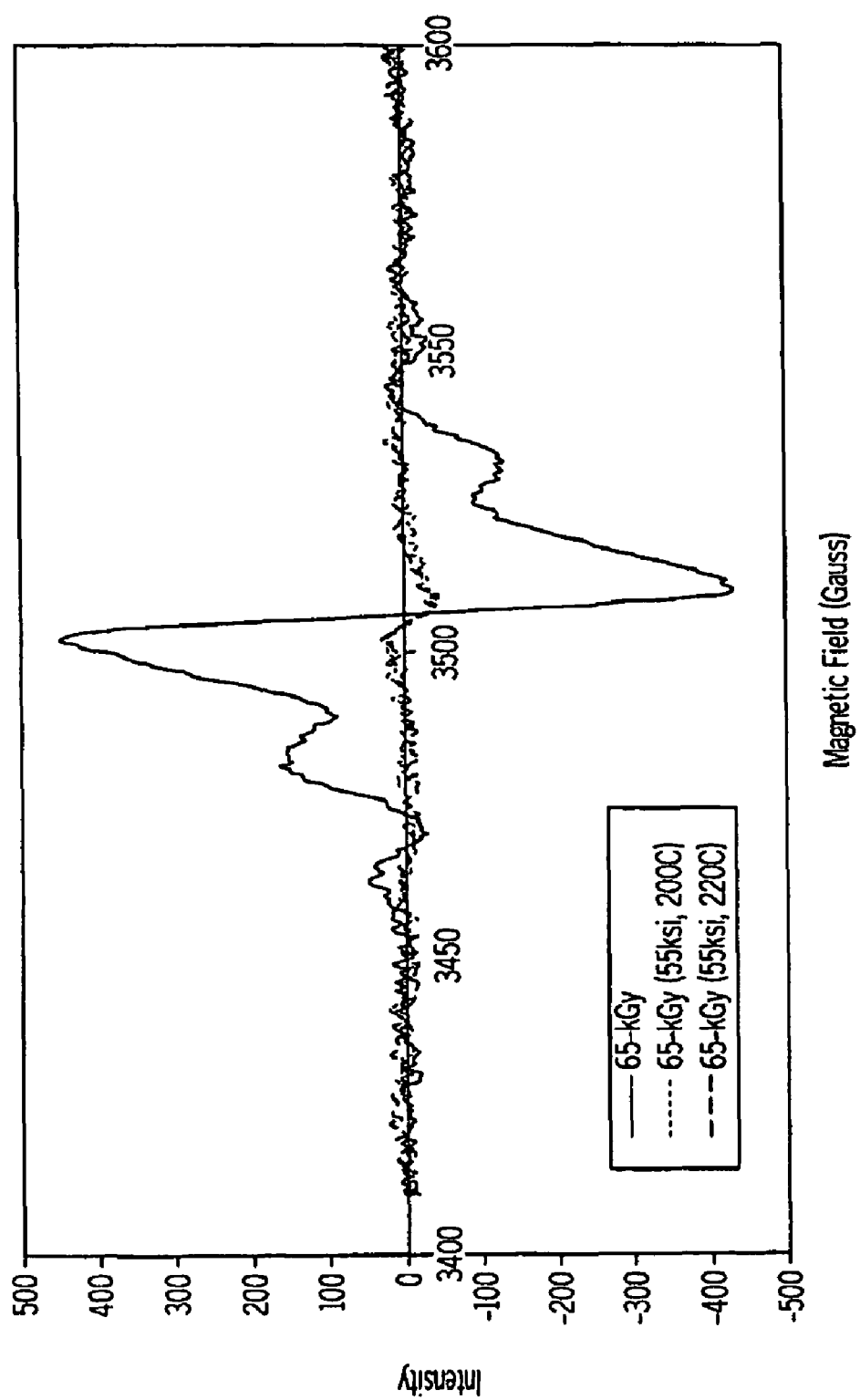
FIG. 13 shows the free radical signals as measured by electron spin resonance of 65-kGy (13A) and 100-kGy (13B) UHMWPE controls and high pressure annealed samples.
Figure 13B:
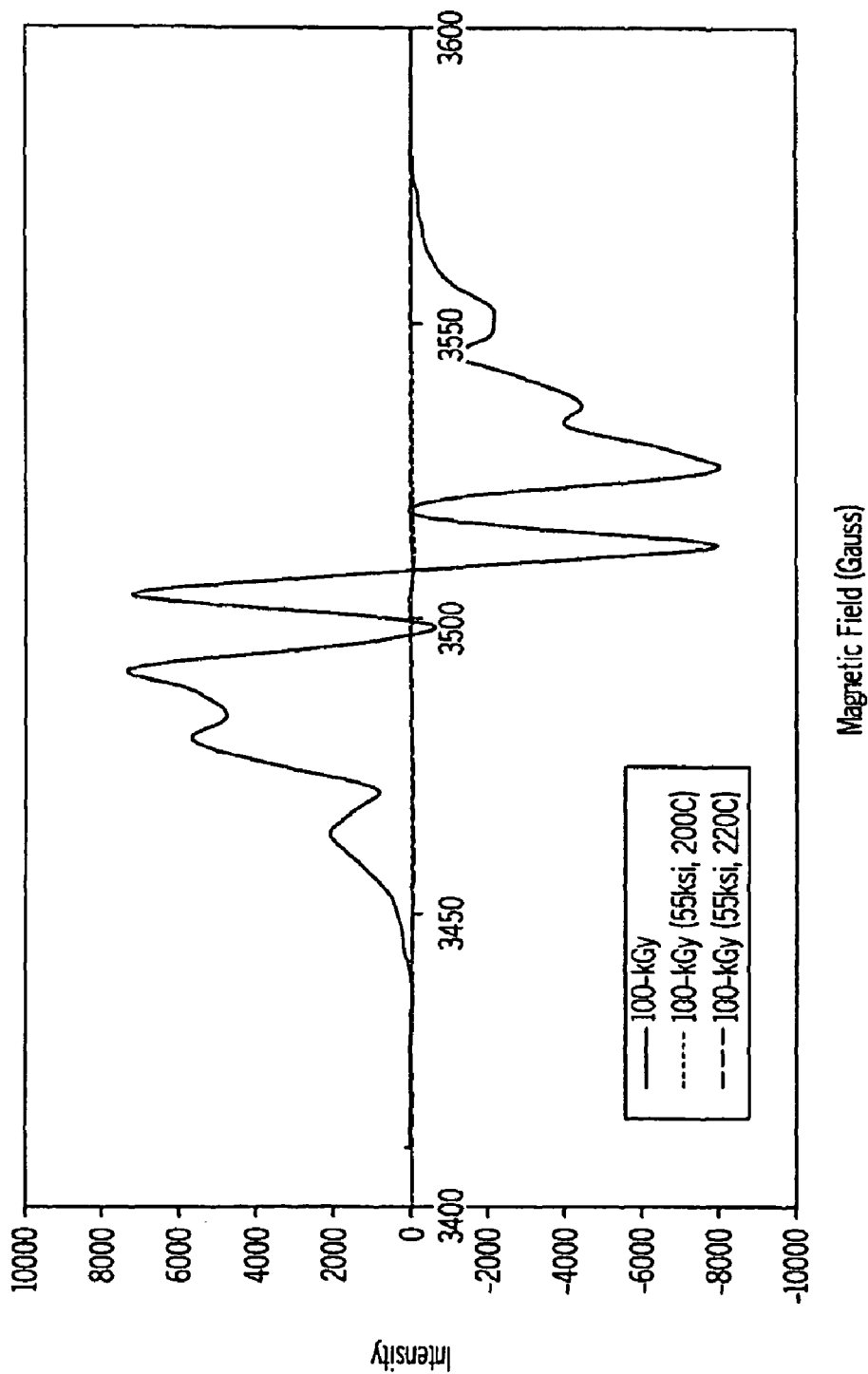

The free radical concentration of all samples are shown in Table 8. Both high pressure crystallization through the melt-phase (Route I) and high pressure crystallization through the solid-phase (Route II) eliminated most of the free radicals in irradiated UHMWPE (see Table 8, also see FIG. 13).

TABLE 8

The free radical concentrations of irradiated and irradiated and high pressure crystallized UHMWPE.

| Sample | Free radical concentration (spins/g) (×10$^{14}$) |
|---|---|
| 65-kGy control | 30.8 |
| 65-kGy Route I 55 ksi/200° C. | 1.42 |
| 65-kGy Route II 55 ksi/200° C. | 0.76 |
| 65-kGy Route II 55 ksi/220° C. | 1.05 |
| 100-kGy control | 113 |
| 100-kGy Route I 55 ksi/200° C. | N/A |
| 100-kGy Route II 55 ksi/200° C. | 3.82 |
| 100-kGy Route II 55 ksi/220° C. | 2.82 |

Example 17

Melting Subsequent to Blending with Vitamin E and Irradiation

Vitamin E is blended with UHMWPE powder at a concentration of 0.01, 0.02, 0.05, 0.1, 0.2, 0.5, 1.0, 2.5 or 50 wt %. The blend is then consolidated into Vitamin E-blended blocks (for example, 5 cm by 10 cm by 12 cm) by compression molding. Some blocks are subsequently irradiated to 25, 50, 75, 100, 125, 150, 200 and 250 kGy using gamma or e-beam irradiation.

Some blocks are heated to above the melting temperature of blended UHMWPE (approximately 137° C. at ambient pressure) and held. The holding time can be 10 minutes to several days. Depending on the amount of time at temperature and the size of the block, some parts or all parts of the block are molten.

Melting of irradiated, vitamin E-containing UHMWPE can change the distribution of vitamin E concentration and also can change the mechanical properties of UHMWPE. These changes can be induced by changes in crystallinity and/or by the plasticization effect of vitamin E at certain concentrations. Melting during or after irradiation also reduces the residual free radicals in polyethylene to undetectable levels.

Example 18

Vitamin E Concentration Profile of Diffused Radiation Cross-Linked UHMWPE

Blocks (10 mm thick) were machined from 100-kGy irradiated UHMWPE (GUR1050, Orthoplastics, Lancashire, UK). One block each was doped in pure vitamin E at 100, 105, 110, and 120° C. for 24 hours. One block each was doped in pure vitamin E at 105° C. for 24, 48, and 72 hours.

The vitamin E concentration profiles were calculated as described previously (Oral et al, Characterization of irradiated blends of α-tocopherol and UHMWPE, Biomaterials, 26: 6657-6663 (2005)) by Fourier Transform Infrared Spectroscopy (FTIR). Briefly, the area under the α-tocopherol peak at 1265 $cm^{-1}$ (limits 1245-1275 $cm^{-1}$) was normalized to the polyethylene peak at 1895 $cm^{-1}$ as a vitamin E index (A. U.). Then, this α-tocopherol or vitamin E index (A.U.) was reported as a function of depth away from the free surface (exterior regions) into the bulk (interior regions) of the sample. The penetration depth was defined as the depth at which the vitamin E index was below 0.02.

Figure 15B:
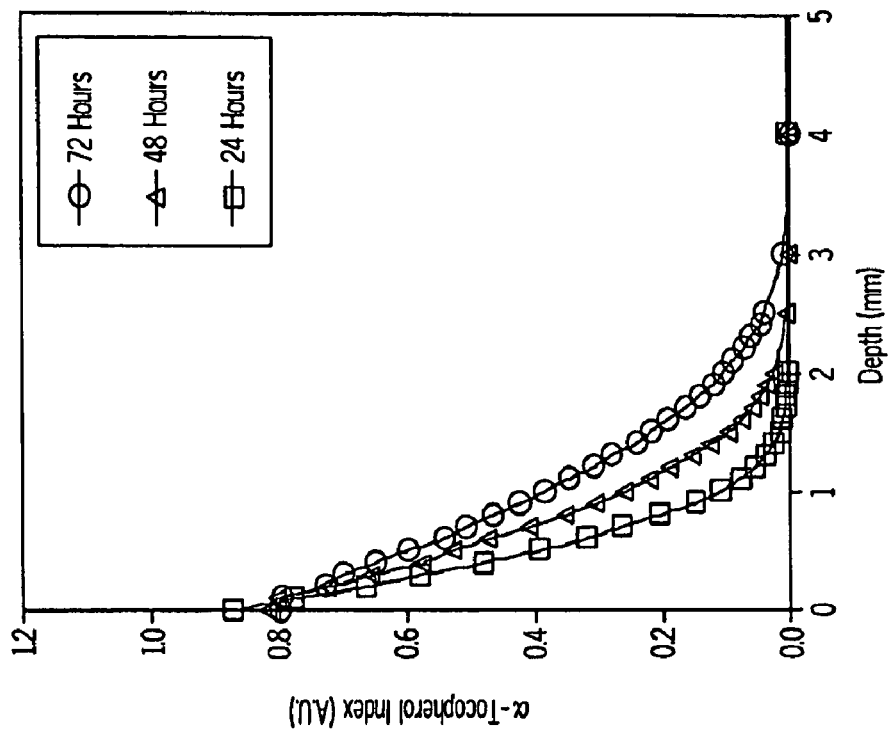
FIG. 15 shows diffusion of α-tocopherol 100 kGy irradiated UHMWPE (15A) as a function of temperature for 24 hours, and (15B) as a function of time at 105° C.
Figure 15A:
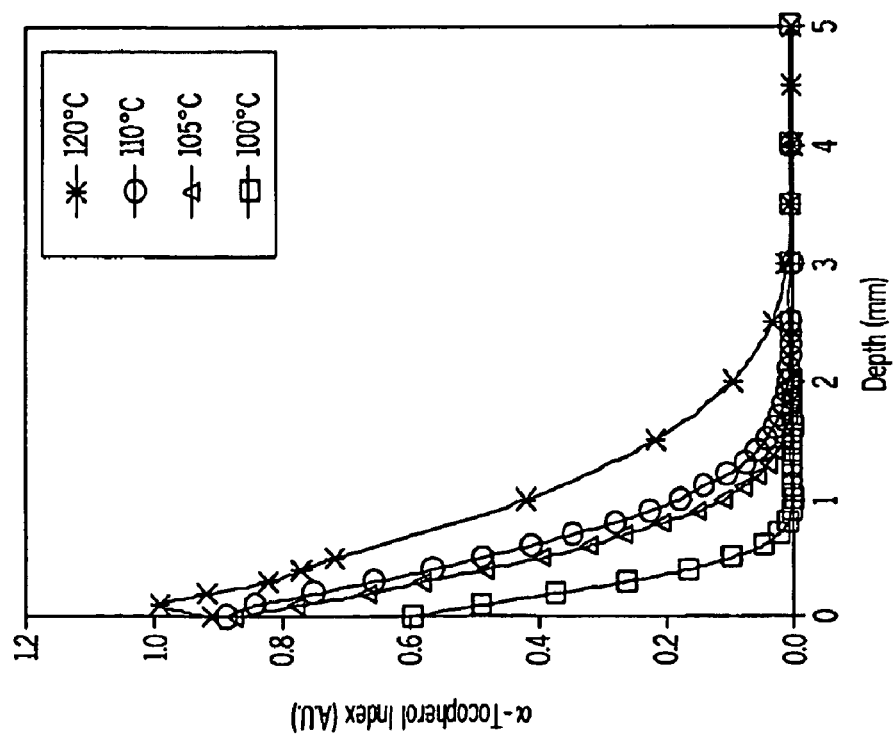

Both surface vitamin E concentration and vitamin E penetration depth was increased as temperature increased (FIG. 15A). At the same doping temperature, increasing time increased depth of penetration (FIG. 15B).

Example 19

Vitamin E Concentration Profile of Diffused and Homogenized UHMWPE

Blocks (10 mm thick) were machined from 85-kGy irradiated UHMWPE (GUR1050, Orthoplastics, Lancashire, UK). One block was doped in pure vitamin E at 120° C. for 4 hours. Another block was doped in pure vitamin E at 120° C. for 4 hours followed by 24 hours of homogenization in argon.

Vitamin E concentration profiles were determined as described in Example 18.

Figure 16:
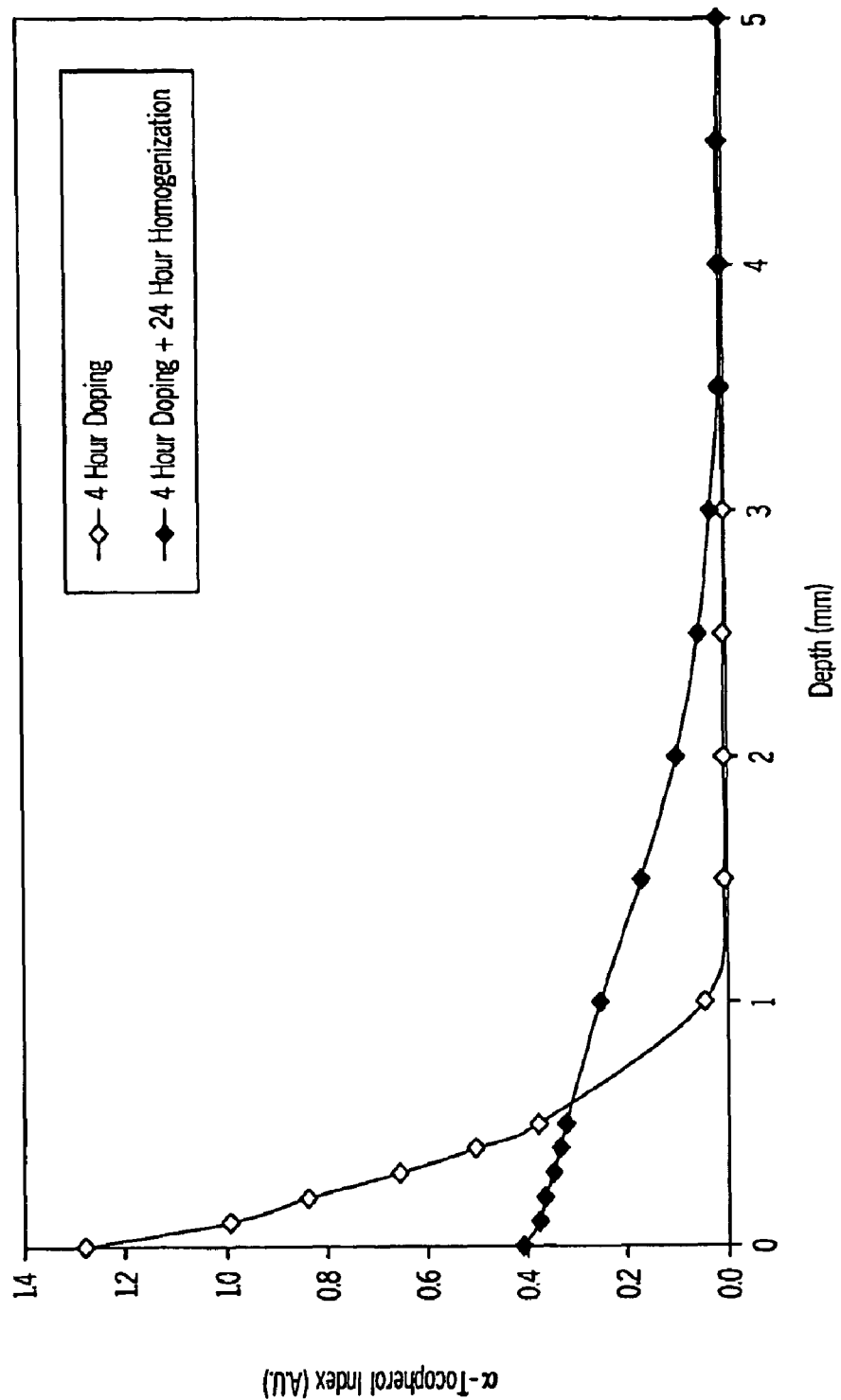
FIG. 16 shows a comparison of α-tocopherol concentration profiles of 85 kGy irradiated UHMWPE doped at 120° C. for 4 hours and of 85 kGy irradiated UHMWPE doped at 120° C. for 4 hours followed by homogenization at 120° C. for 24 hours.

Homogenization subsequent to doping in vitamin E enhanced the penetration depth and decreased the surface concentration due to diffusion of the vitamin E at the surface into the bulk of the sample (FIG. 16).

Example 20

Vitamin E Concentration Profiles of Vitamin E-Blended UHMWPE and Subsequently Irradiated Samples Vitamin E (D,L-α-tocopherol, Alfa Aesar, Ward Hill, Mass.) was mixed with GUR1050 UHMWPE powder at a concentration of 5 wt/wt %, then diluted for consistency with UHMWPE resin powder to 1.0 wt %. The mixture was consolidated into α-tocopherol-blended blocks (5.5 cm×10 cm×12 cm) by compression molding.

Figure 17:
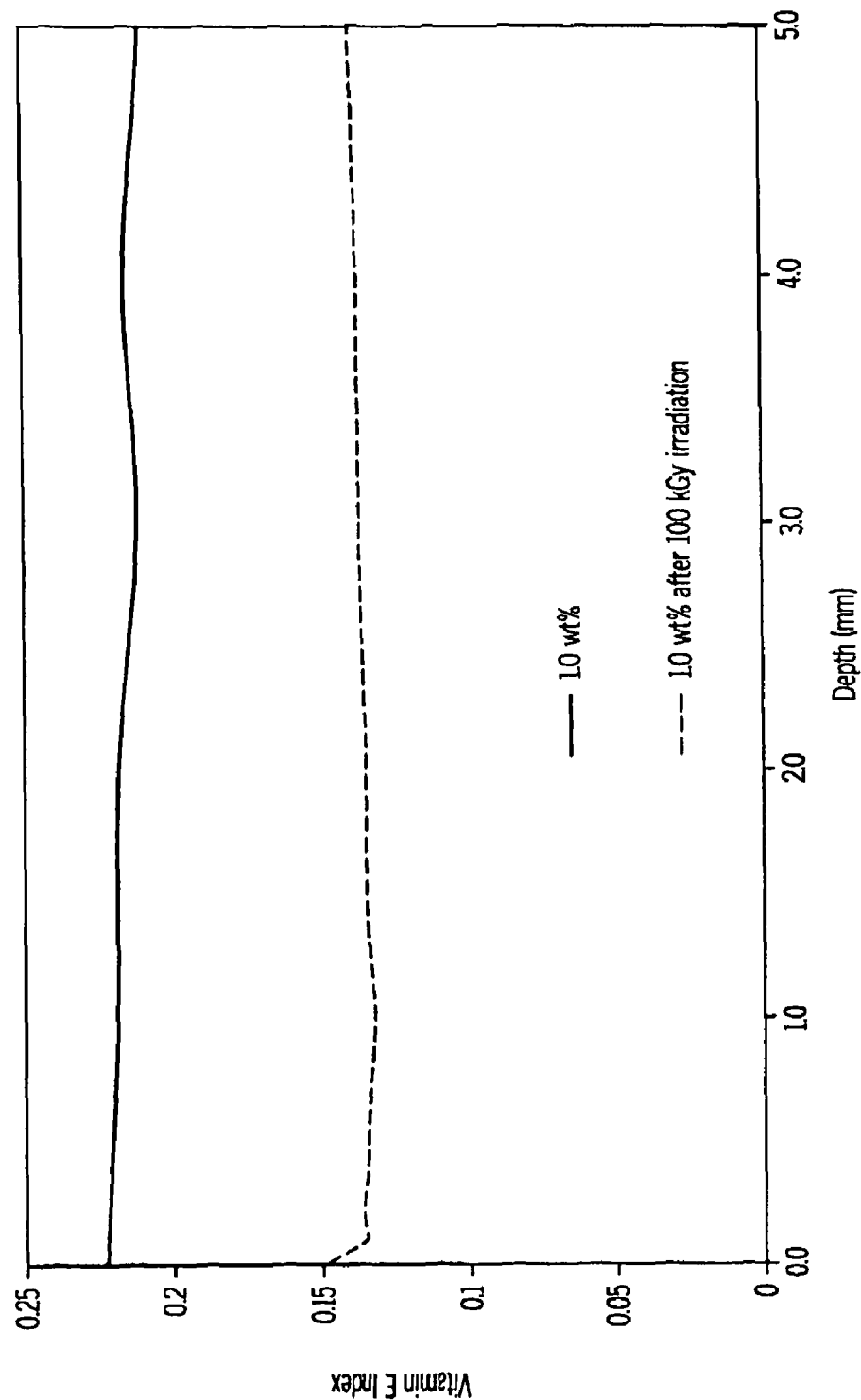
FIG. 17 depicts vitamin E concentration profiles of 1.0 wt % α-tocopherol-blended UHMWPE before and after 100 kGy gamma irradiation.

One block was subsequently irradiated to 100-kGy using gamma irradiation (Steris Isomedix, Northborough, Mass.). The vitamin E concentration profiles of 5 cm-thick unirradiated and irradiated pieces were determined using FTIR spectroscopy as described in Example 18 and are shown in FIG. 17.

Some vitamin E was used during high dose irradiation (100 kGy) as determined by the decrease in the vitamin E absorbance and concentration after irradiation.

Example 21

Extraction of Vitamin E Concentration Profiles of Vitamin E-Blended UHMWPE Samples Vitamin E (D,L-α-tocopherol, Alfa Aesar, Ward Hill, Mass.) was mixed with GUR1050 UHMWPE powder at a concentration of 5 wt/wt %, then diluted for consistency with UHMWPE resin powder to 1.0 wt %. The mixture was consolidated into α-tocopherol-blended blocks (5.5 cm×10 cm×12 cm) by compression molding.

One block was subsequently irradiated to 100-kGy using gamma irradiation (Steris Isomedix, Northborough, Mass.).

The surface vitamin E concentration was reduced using extraction in boiling ethanol for 16 hours in both samples. The vitamin E concentration profiles of unirradiated and irradiated UHMWPE before and after extraction were determined using FTIR spectroscopy as described in Example 18 and are shown in FIG. 18.

Figure 18:
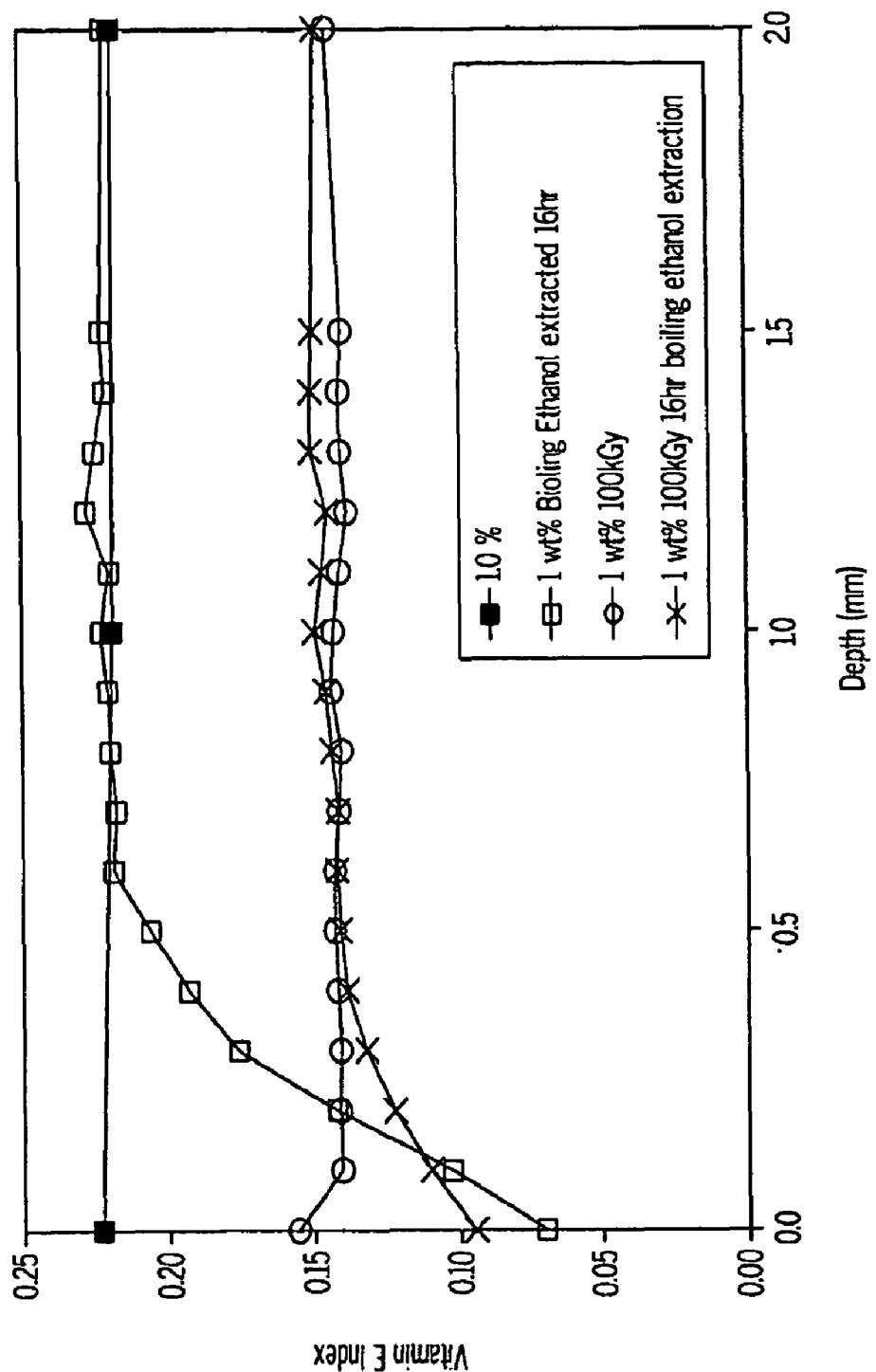
FIG. 18 shows vitamin E concentration profiles of vitamin E-blended and subsequently irradiated UHMWPE before and after extraction in boiling ethanol for 16 hours.

Boiling ethanol was instrumental in reducing the surface concentration of vitamin E in both unirradiated and irradiated 1 wt % α-tocopherol-blended consolidated UHMWPE blocks (FIG. 18).

Example 22

Solubilization of Vitamin E in an Aqueous Solution or Emulsion

Surfactant Tween 80 (Polyethylene glycol sorbitan monooleate, Sigma, St. Louis, Mo.) and vitamin E (D, L-α-tocopherol, DSM Nutritional Products, Pouhkeepsie, N.J.) were heated at 60° C. A 20 mg of vitamin E was weighed in an Erlenmeyer flask, then Tween 80 was added to the vitamin E in the desired amount so that amount of Tween 80 was 3 weight percentage of the solution. A 20 mL of water was added to this mixture. The mixture was boiled under reflux until a clear solution or a stable emulsion was obtained. This emulsified solution contained 1 mg/mL vitamin E (solution containing 3 wt % Tween 80 in deionized water) and was clear. Alternatively, the same amount of vitamin E was mixed with 0.25 wt % Tween 80 in a 20 mL 1 wt % ethanol/water emulsion was cloudy.

A 5 mg/mL vitamin E solution was prepared by using 10-15 wt % Tween 80 in deionized water and a 5 mg/mL vitamin E emulsion was prepared by using 0.25 wt % Tween 80 in a 20 mL 6 wt % ethanol/water emulsion.

Example 23

Vitamin E Detection Limits

Vitamin E (D,L-α-tocopherol, Alfa Aesar, Ward Hill, Mass.) was mixed with GUR1050 UHMWPE powder at a concentration of 5 wt/wt %, then diluted for consistency with UHMWPE resin powder to 0.1 and 1.0 wt %. The mixtures were consolidated into α-tocopherol-blended blocks (5.5 cm×10 cm×12 cm) by compression molding.

Figure 19:
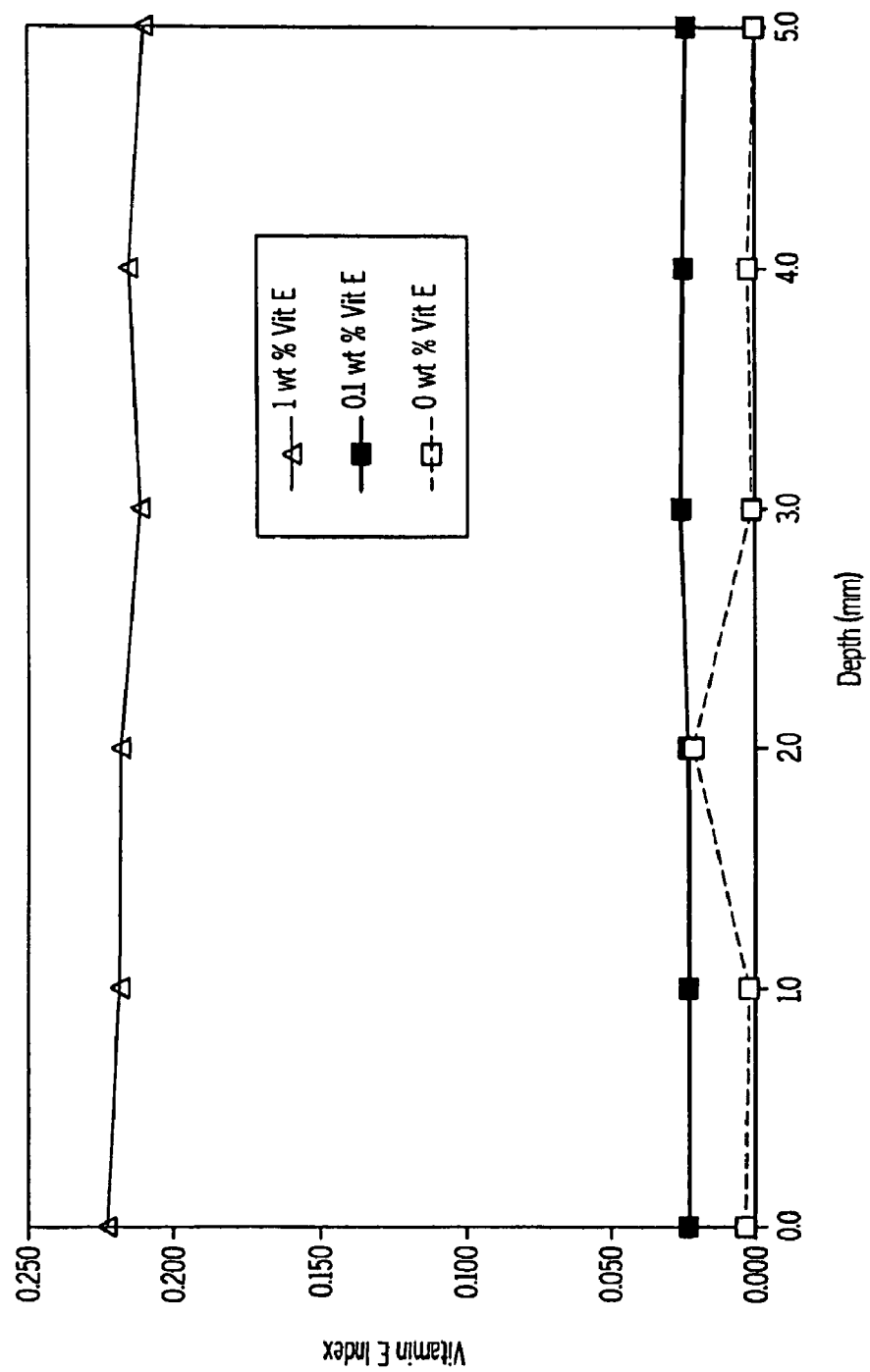
FIG. 19 shows vitamin E concentration profiles of vitamin E-blended UHMWPE

The vitamin E concentration profiles were determined using FTIR spectroscopy as described in Example 18 and are shown in FIG. 19 in comparison with a control UHMWPE containing no vitamin E. The detection limit by the spectroscopic technique was set at 0.01 based on these results.

Example 24

Extraction of Vitamin E from the Surface of Diffused and Homogenized UHMWPE Subsequent to Irradiation Using an Emulsion with a Surfactant Blocks (20 mm cubes) of 100-kGy irradiated UHMWPE were doped with vitamin E at 120° C. for 2 hours under argon purge. At the end of the doping period, the samples 0.10 were taken out of the vitamin E and cooled down to room temperature. The excess vitamin E was wiped off using cotton gauze. The samples were then homogenized under argon purge at 120° C. for 24 hours. At the end of the homogenization period, the samples were cooled down to room temperature under argon purge.

A 10 wt % Tween 80 solution was prepared in deionized water. A pressure chamber was heated to 120° C. in an air convection oven. The solution was placed in the heated chamber with the UHMWPE samples and the chamber was sealed. The extraction of vitamin E from the doped and homogenized UHMWPE continued for 20 hours under self generated pressure. At the end of the 20 hours, the chamber was cooled down to room temperature and the pressure was released.

Alternatively, a 20 wt % Tween 80 solution and a 10 wt % Tween 80 emulsion in 10 wt % ethanol was prepared in deionized water. The solution was placed in an Erlenmeyer flask with the UHMWPE samples and was boiled under reflux at ambient pressure for 20 hours.

Figure 20:
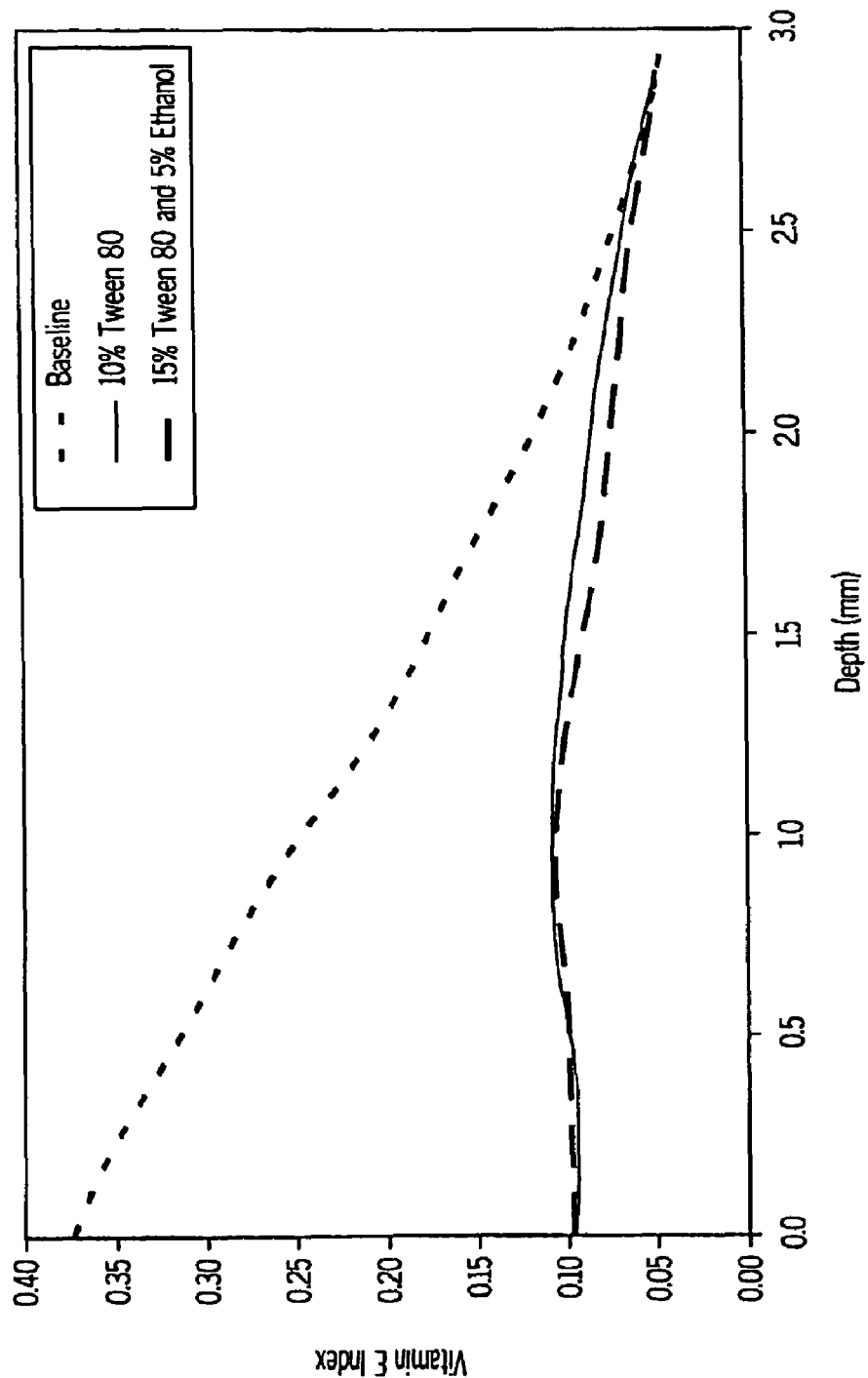
FIG. 20 illustrates vitamin E concentration profiles of 100-kGy irradiated UHMWPE doped and homogenized at 120° C. before and after extraction in a surfactant solution and emulsion under self-generated pressure at 120° C. for 20 hours.
Figure 21:
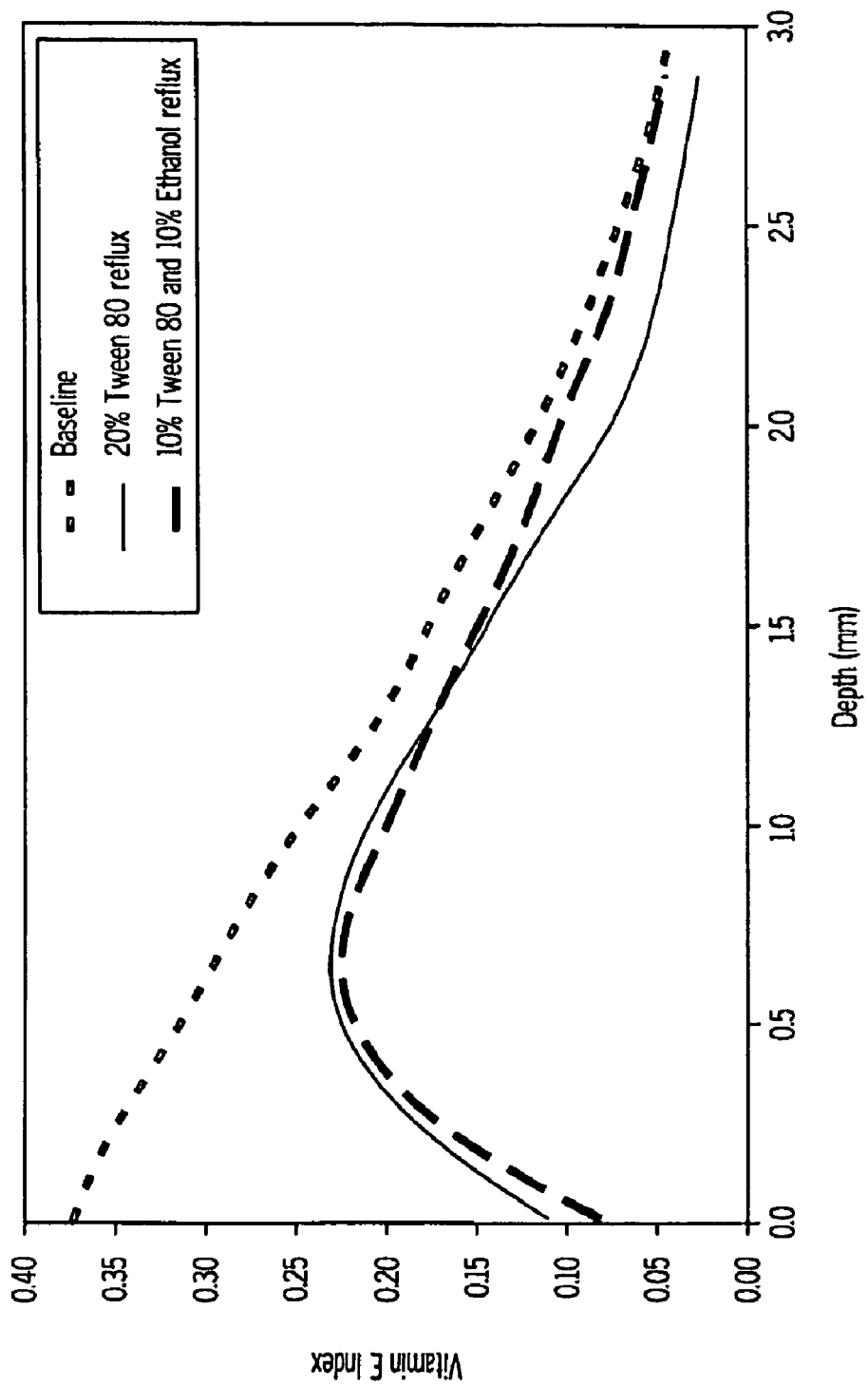
FIG. 21 illustrates vitamin E concentration profiles of 100-kGy irradiated UHMWPE doped and homogenized at 120° C. before and after extraction at ambient pressure at boiling temperature under reflux.

The vitamin E concentration profiles of doped and homogenized UHMWPE and extracted UHMWPE were determined as described in Example 18. The surface concentration of extracted samples was significantly reduced both under self-generated pressure at 120° C. and at ambient pressure at boiling temperature (FIGS. 20 and 21, respectively).

Example 25

Hexane Extraction of Diffused, Homogenized and Sterilized UHMWPE

Two different acetabular liners: an 85-kGy irradiated, α-tocopherol-doped, and gamma-sterilized UHMWPE and an 85-kGy irradiated UHMWPE were tested. Both liners were prepared with a 5-mm nominal thickness. Both liners had an inner diameter of 36-mm.

The two liners were machined from GUR1050 UHMWPE. Both liners were packaged under argon gas. The package was then gamma-irradiated to 85-kGy. One of the liners was used as irradiated control. The other liner was subsequently doped in α-tocopherol at 120° C. for 2 hours and homogenized at 120° C. for 24 hours under argon gas. The doped and annealed liner was packaged in argon gas and gamma sterilized.

Each liner was cut into four quarters. One was analyzed as control. One was extracted in boiling hexane (65-70° C.) in separate reflux chambers for 72 hours. One was hexane extracted and accelerated bomb aged at 70° C. for 2 weeks at 5 atm. of $O_2$. One was hexane extracted and accelerated oven aged at 80° C. for 6 weeks in air.

Figure 22:
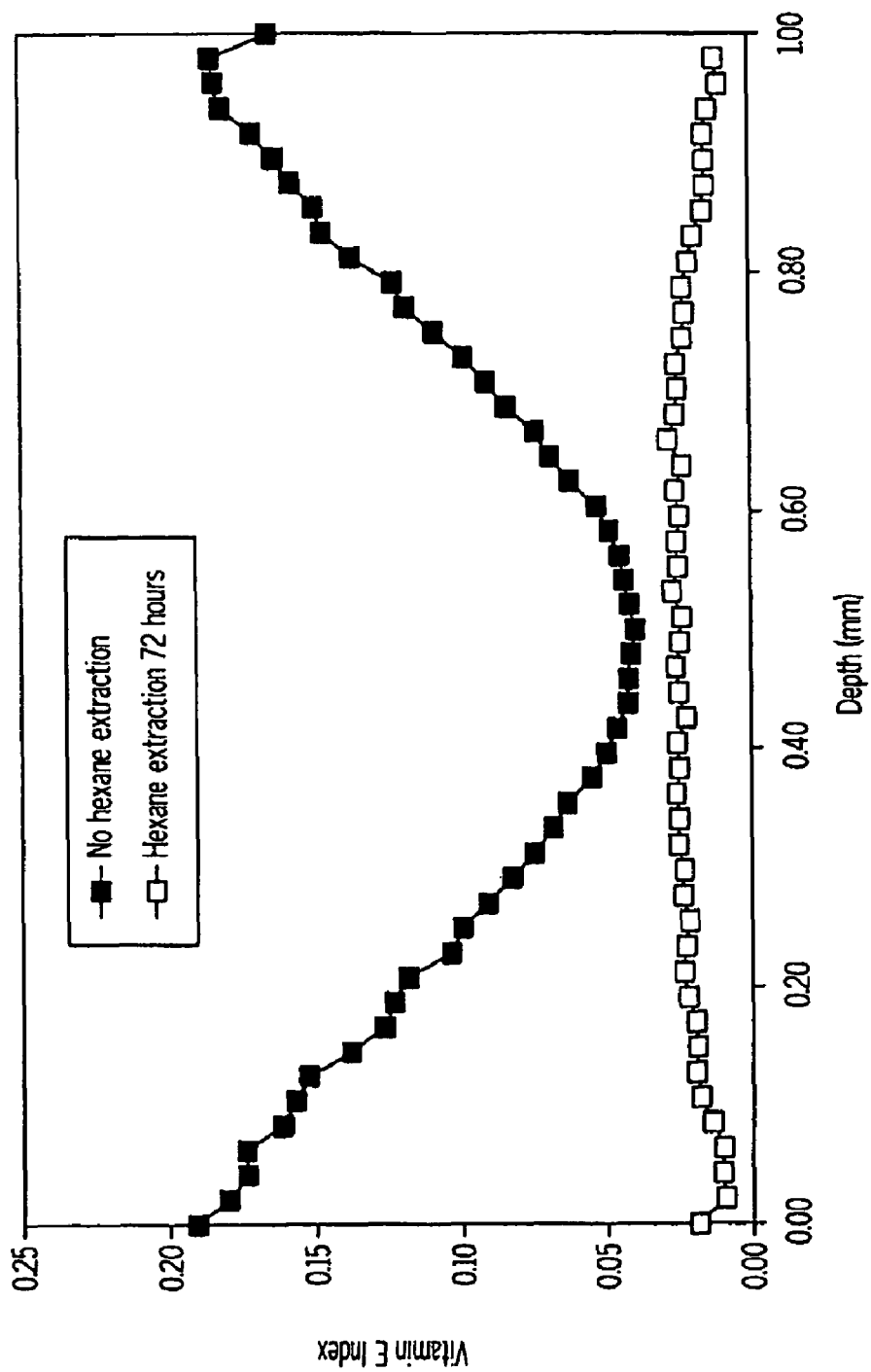
FIG. 22 shows vitamin E concentration profiles of 85-kGy irradiated, doped, homogenized and sterilized acetabular liners before and after boiling hexane extraction for 72 hours.
Figure 23:
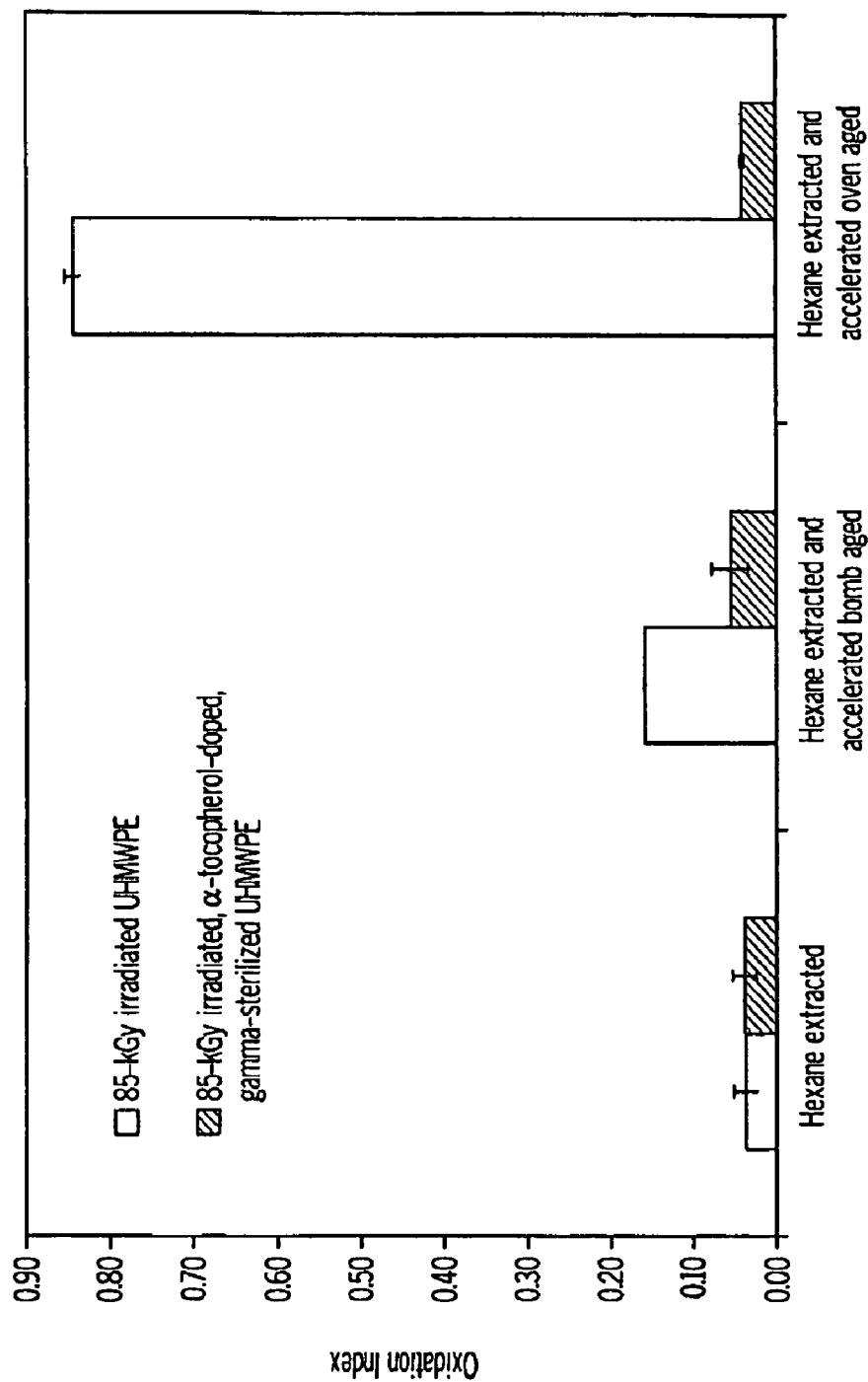
FIG. 23 depicts average surface oxidation indices of 85-kGy irradiated UHMWPE and 85-kGy irradiated, α-tocopherol doped UHMWPE after hexane extraction, accelerated bomb aging and accelerated oven aging.
Figure 24:
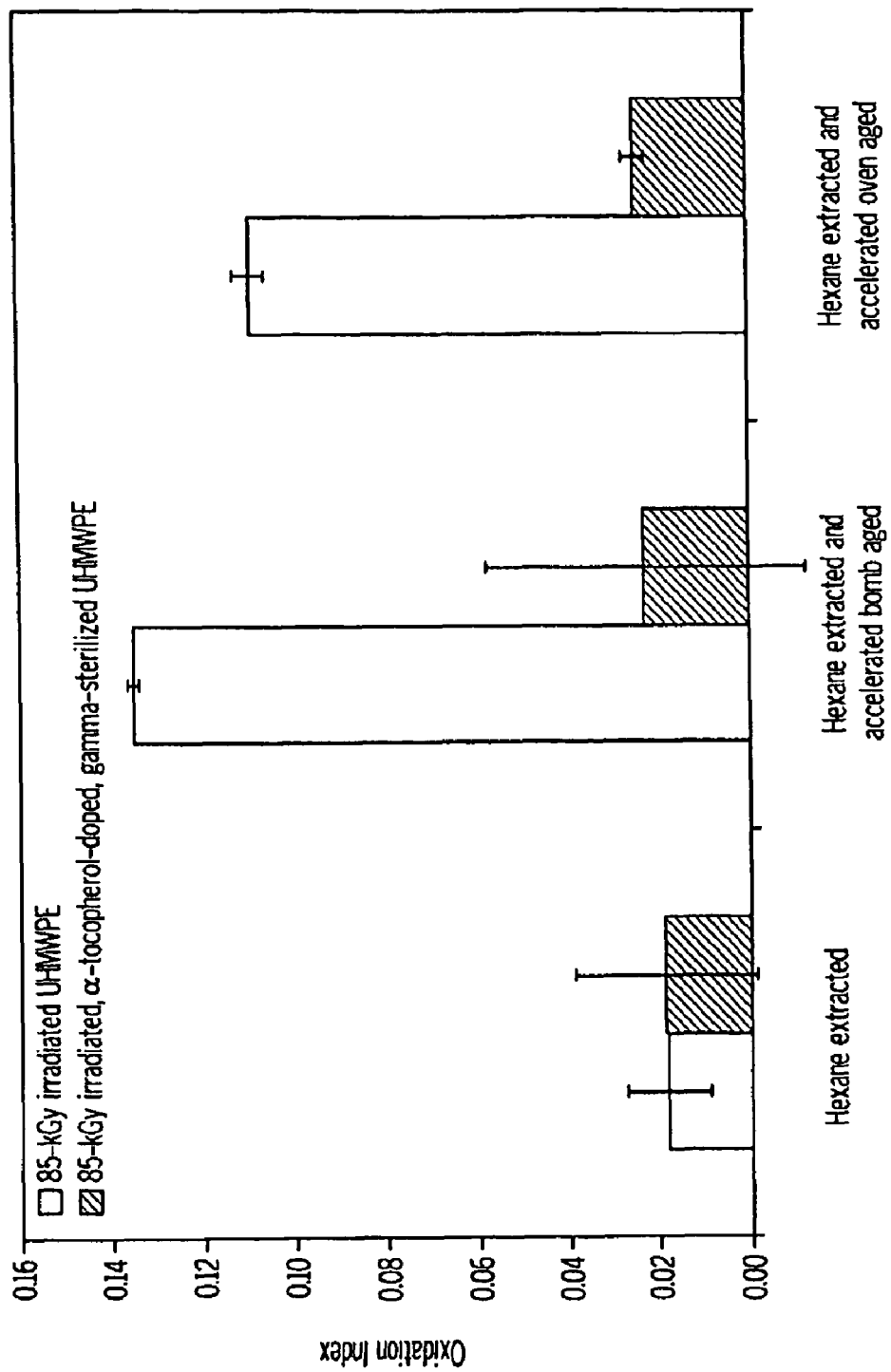
FIG. 24 depicts average bulk oxidation indices of 85-kGy irradiated UHMWPE and 85-kGy irradiated, α-tocopherol doped UHMWPE after hexane extraction, accelerated bomb aging and accelerated oven aging.

Hexane extraction for 72 hours resulted in the migration of detectable α-tocopherol out of the acetabular liner pieces (FIG. 22). Although 85-kGy irradiated UHMWPE showed high oxidation after accelerated aging both on the surface (FIG. 23) and bulk (FIG. 24), hexane extracted vitamin E-doped samples were still stable against oxidation, exhibiting only baseline levels of oxidation after 2 weeks of accelerated aging in oxygen at 5 atm and 70° C. (ASTM F2003-02). The oxidation observed in just irradiated samples was not due to hexane extraction.

Example 26

The Effect of Sterilization on the α-Tocopherol Concentration Profile

GUR1050 UHMWPE was annealed at 130° C. for 5 hours, 124° C. for 5 hours, 119° C. for 5 hours, 113° C. for 5 hours and 105° C. for 5 hours, then cooled to room temperature over 10 hours. A 4 cm-thick pieces of annealed UHMWPE were irradiated to 100-kGy at 25 kGy/pass using a 10 MeV electron generator (Iotron Inc., Vancouver, BC) in vacuum. Hemispherical performs (approximately 6.8 mm thick) for acetabular liners were doped for 2.5 hours at 120° C. under argon purge, followed by 40 hours of homogenization at 120° C. as described in Example 19. Canine acetabular liners (approximately 2.6 mm thick) were machined from these preforms. Then, the liners were individually packaged in vacuum and sterilized by gamma irradiation.

Figure 25:
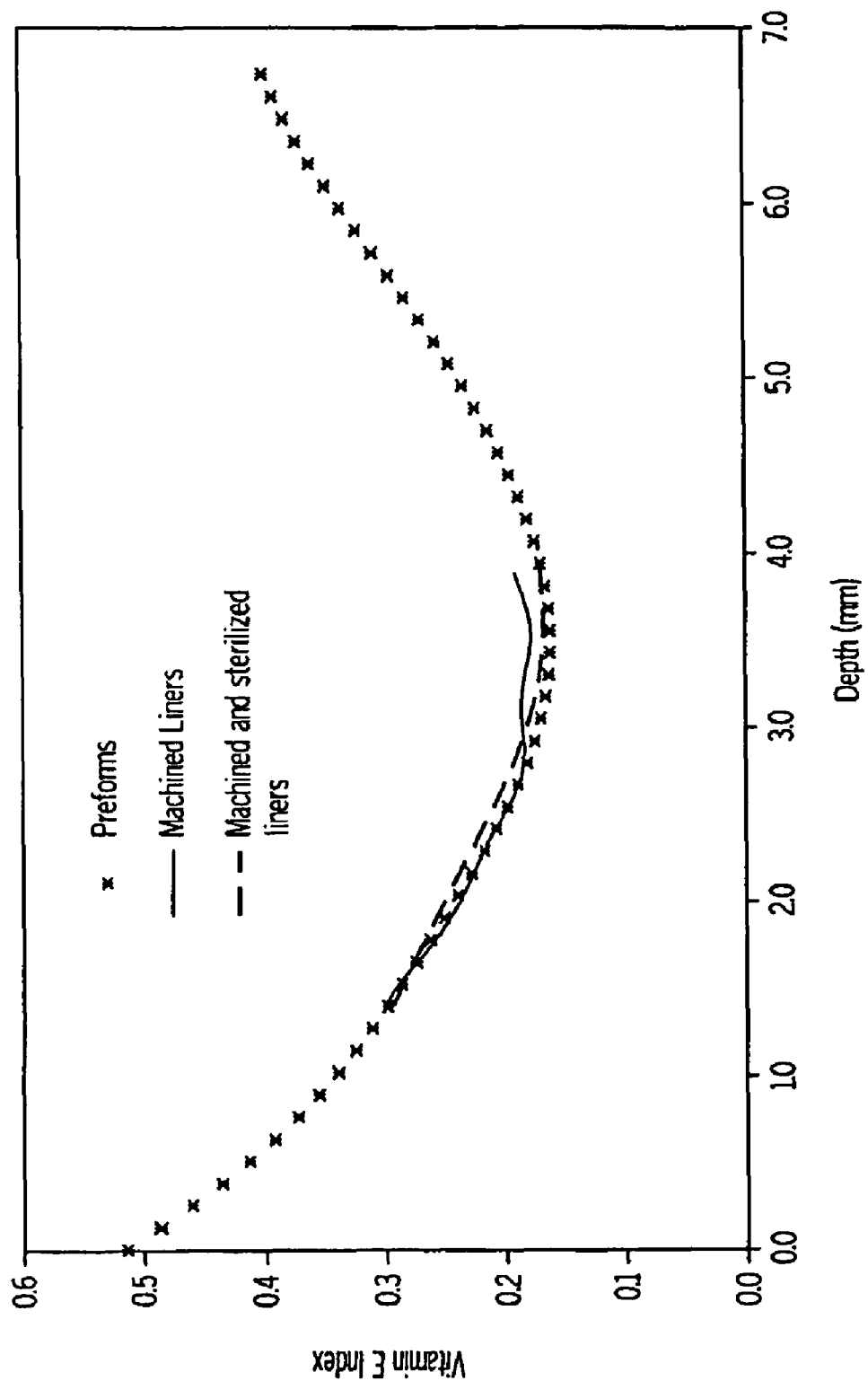
FIG. 25 shows vitamin E concentration profiles for preforms (6.8 mm thick), 2.6 mm-thick liners machined from these preforms and 2.6 mm-thick liners after sterilization. The profiles are splined averages of three separate samples.

The vitamin E concentration profiles of doped and homogenized preforms, machined acetabular liners, and sterilized acetabular liners were determined as described in Example 18 and are shown in FIG. 25.

These profiles show that the surface and bulk concentrations can be controlled by machining after doping and homogenization. They also showed that sterilization dose radiation (25-40 kGy) did not have an observable difference in the vitamin E profile at this vitamin E concentration.

Alternatively, canine acetabular liners were directly machined from 100-kGy irradiated annealed UHMWPE. These liners were doped with vitamin E and homogenized as described above. One set of these liners were subjected to extraction in 15 wt % Tween 80 solution in a 5 wt % ethanol/water emulsion at 120° C. under self-generated pressure as described in Example 24.

Figure 26:
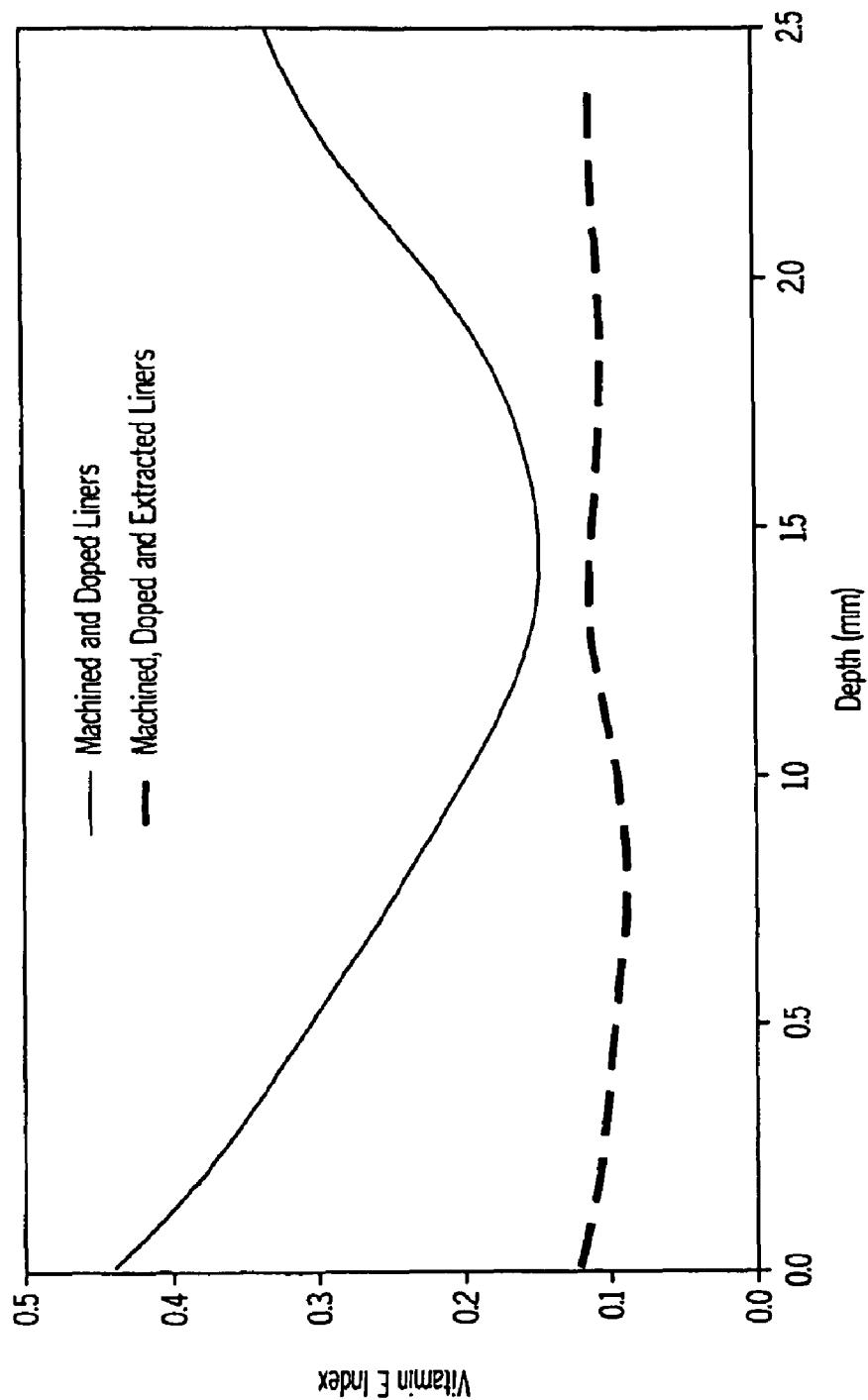
FIG. 26 depicts the vitamin E concentration profiles of vitamin E doped and homogenized liners before and after extraction by a surfactant emulsion.

The vitamin E concentration profiles of doped and homogenized actabular liners before and after extraction were determined as described in Example 18 and are shown in FIG. 26.

Example 27

The Potency of α-Tocopherol Against High Dose Irradiation

A 3 cm cube of 100-kGy irradiated GUR1050 UHMWPE was doped with vitamin E for 48 hours at 100° C. This cube was accelerated aged at 70° C. in 5 atm $O_2$ for 2 weeks. To determine the α-tocopherol or oxidation profile into polyethylene, the samples were cut in half and sectioned (150 µm) using an LKB Sledge Microtome (Sweden). The thin sections were then analyzed using a BioRad UMA 500 infrared microscope (Natick, Mass.). Infrared spectra were collected with an aperture size of 50×50 µm as a function of depth away from the free surface of the cube. The infrared spectra were analyzed to calculate a "sensitive α-tocopherol index", as the ratio of the areas under the 1265 $cm^{-1}$ α-tocopherol and 1895 $cm^{-1}$ polyethylene skeletal absorbances. An oxidation index was calculated as the ratio of the areas under the 1740 $cm^{-1}$ carbonyl and 1370 $cm^{-1}$ methylene stretching absorbances.

Figure 27:
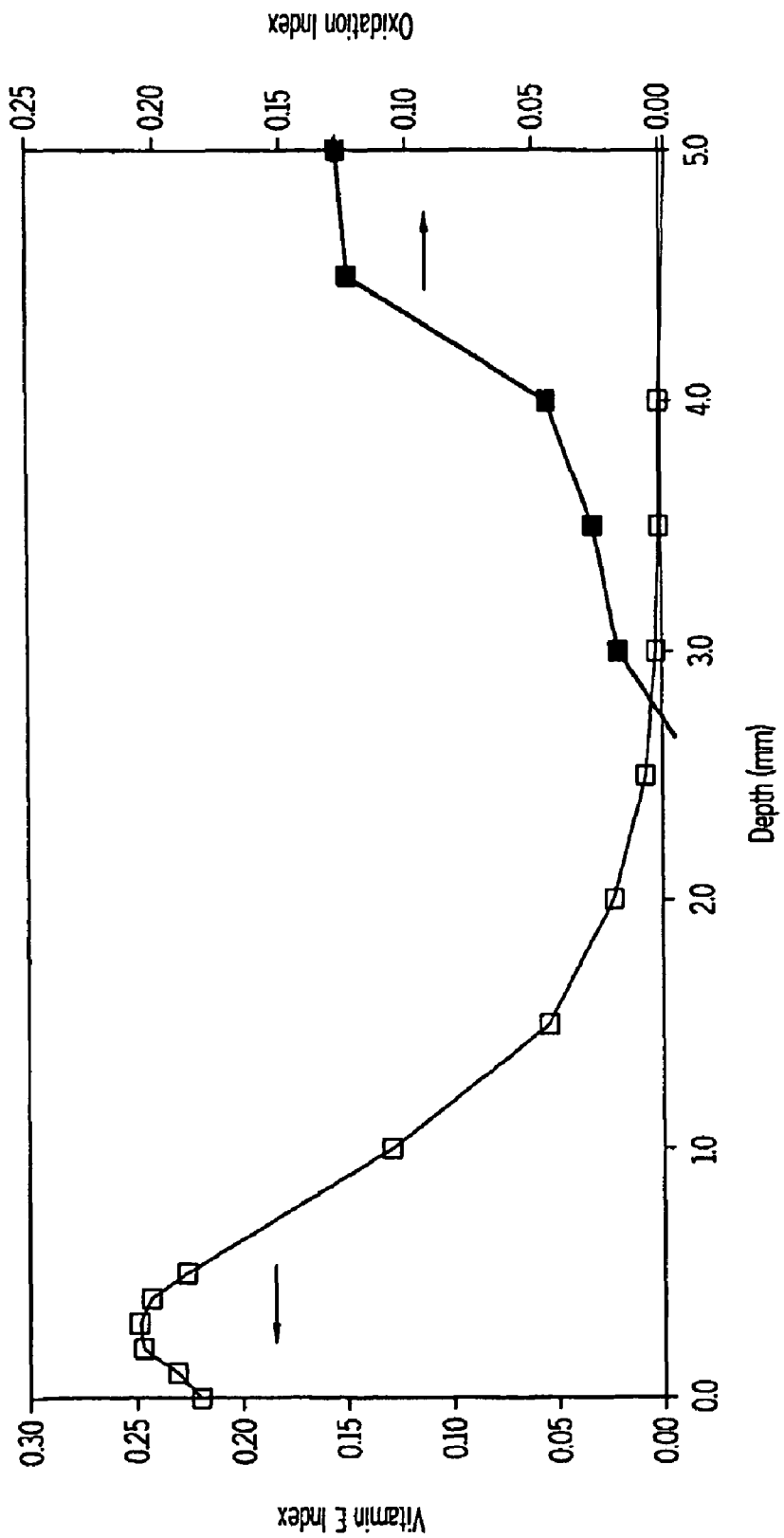
FIG. 27 shows vitamin E and oxidation profile of 100-kGy irradiated UHMWPE doped for 48 hours at 100° C.

The depth at which there was significant oxidation was where the vitamin E index dropped below 0.01 (FIG. 27). Hence, the bulk of the sample containing less than this amount was susceptible to oxidation. Therefore, it was desirable to have a vitamin E index of at least 0.01 throughout the entire sample.

Figure 28:
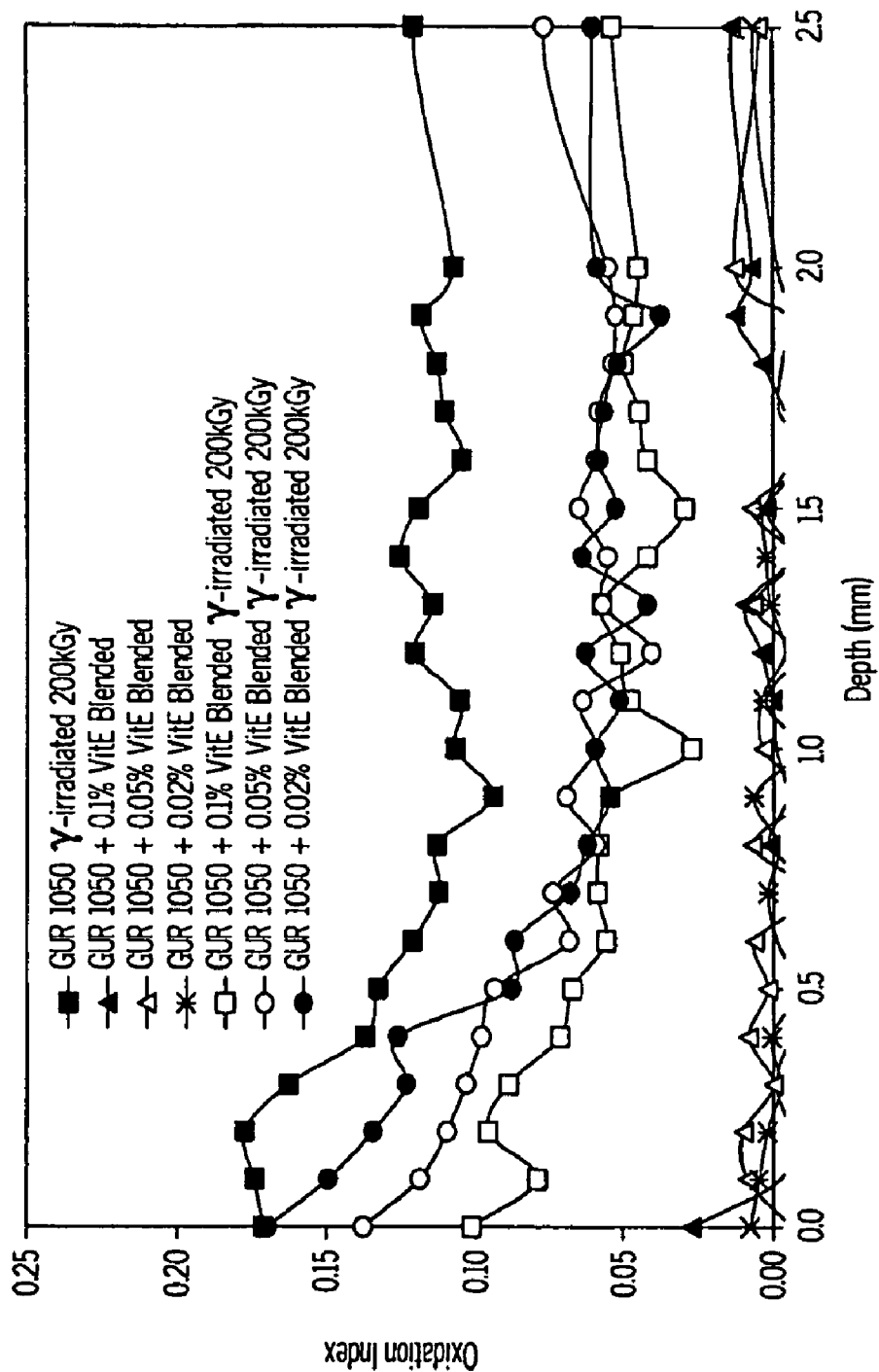
FIG. 28 illustrates the oxidation profiles of vitamin E-blended and 200-kGy irradiated UHMWPE.

Also, the effect of high dose irradiation on blended samples is shown in FIG. 28. The oxidation levels after irradiation increased with decreasing vitamin E concentration in the blends.

Example 28

Vitamin E Concentration Profiles of Real-Time Aged Doped, Homogenized and Sterilized UHMWPE Hot isostatically pressed GUR1050 UHMPWE stock (Biomet, Inc.) was used in all experiments. Blocks (30×30×10 mm) were machined and γ-irradiated to 85-kGy in inert gas. The blocks were doped with α-tocopherol (Vitamin E) at 120° C. for 5 hours followed by homogenization at 120° C. in argon for 64 hours. All samples were packaged in inert gas and γ-sterilized.

Blocks were aged on the shelf at room temperature, at 40° C. in air and at 40° C. in water for 16 months. Three sections each were cut at 1, 2, 4, 7, 12, and 16 months to determine the vitamin E concentration profiles, which were determined using FTIR spectroscopy as described in Example 18 and are shown in FIGS. 29, 30 and 31.

Figure 29:
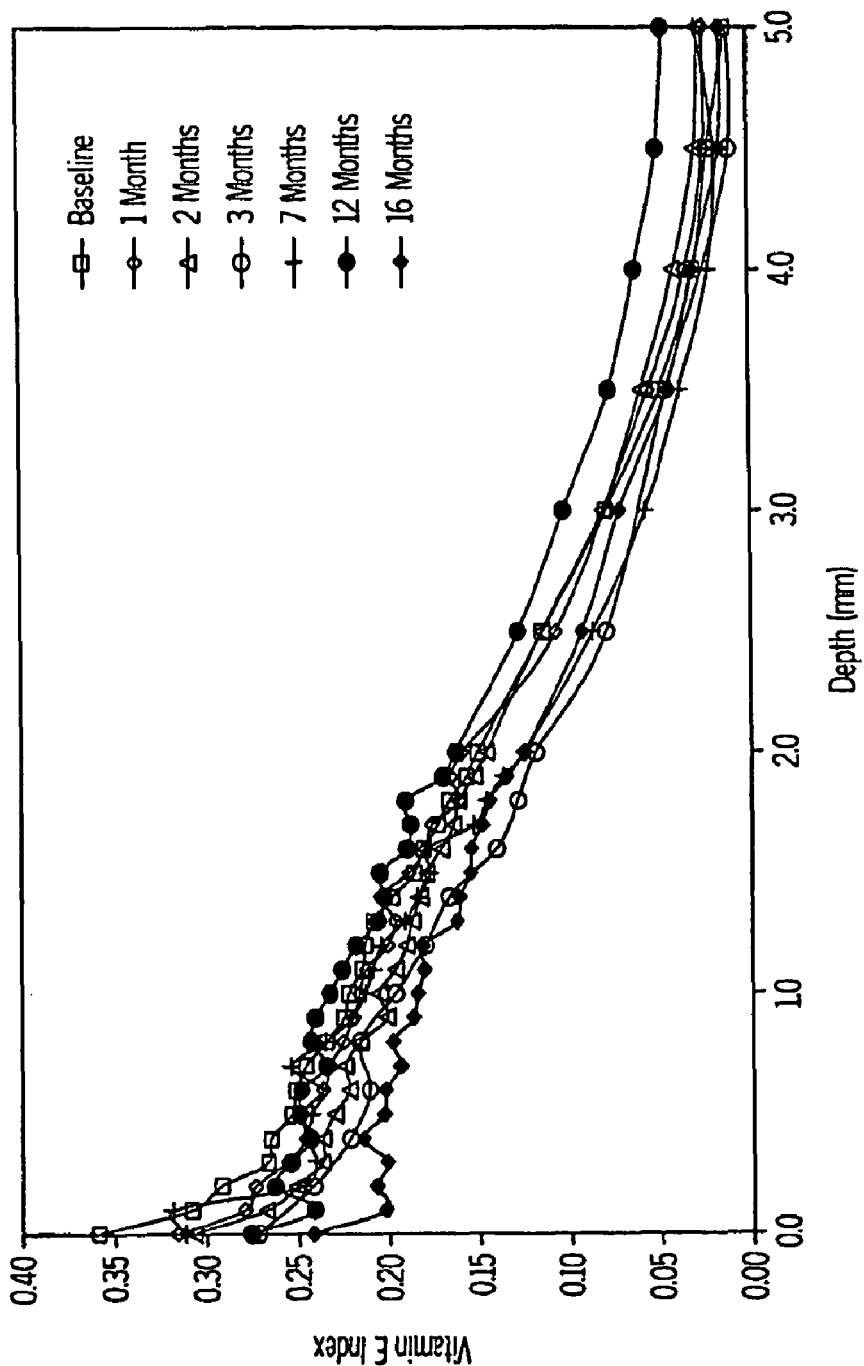
FIG. 29 demonstrates vitamin E concentration profiles of highly cross-linked, doped, homogenized and sterilized UHMWPE real-time aged at room temperature on the shelf.
Figure 30:
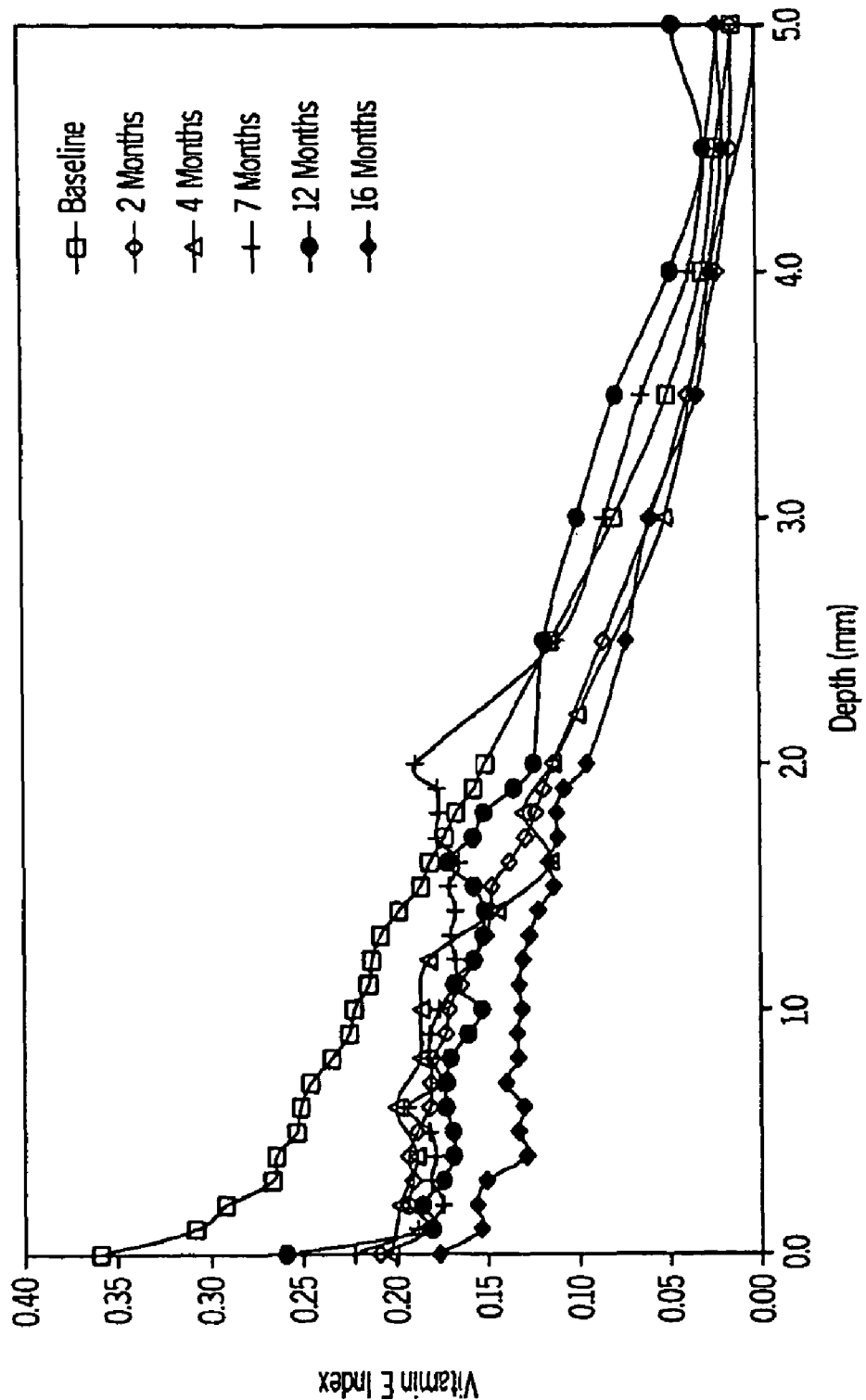
FIG. 30 demonstrates vitamin E concentration profiles of highly cross-linked, doped, homogenized and sterilized UHMWPE real-time aged at 40° C. in air.
Figure 31:
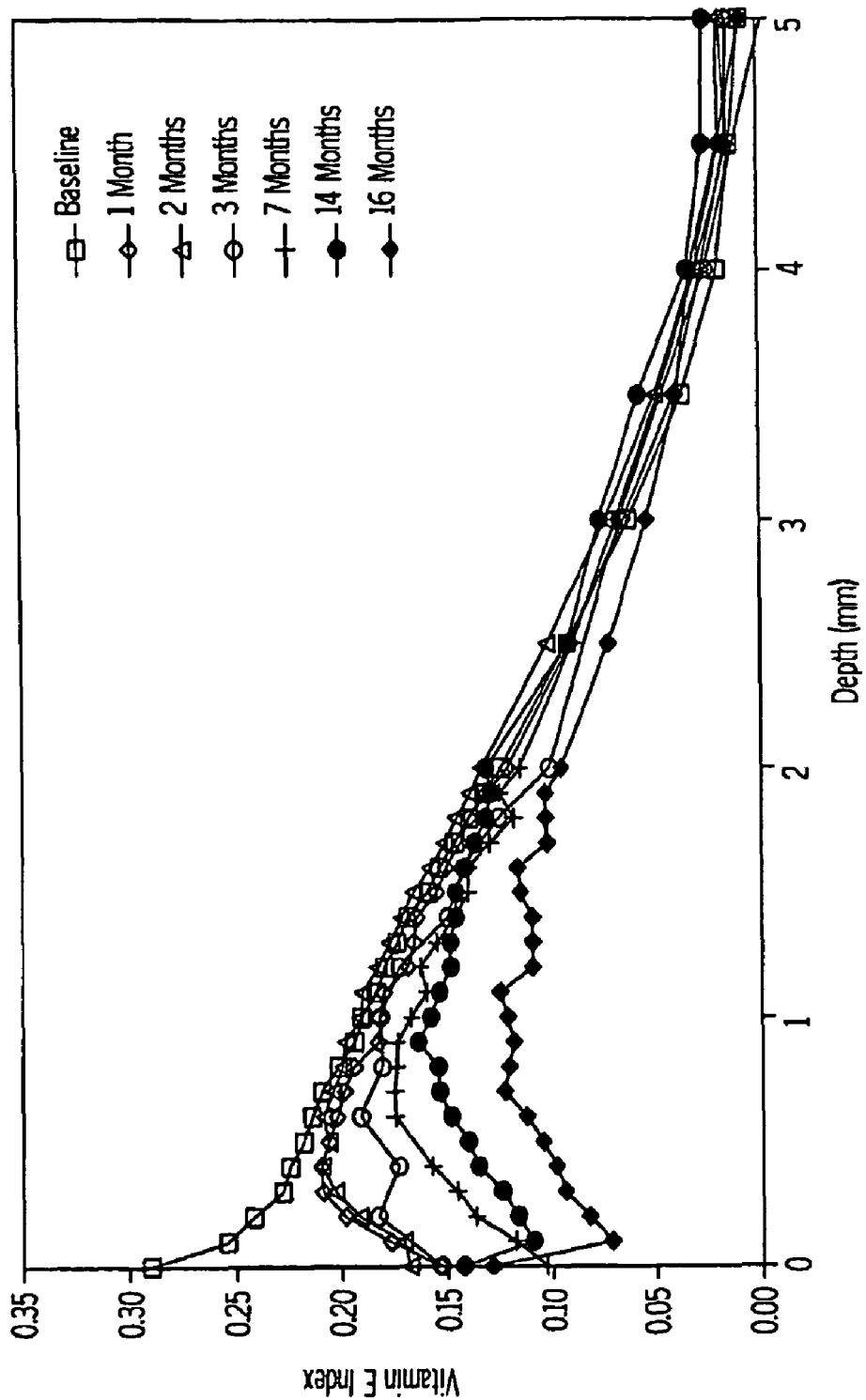
FIG. 31 demonstrates vitamin E concentration profiles of highly cross-linked, doped, homogenized and sterilized UHMWPE real-time aged at 40° C. in water.

Although the surface vitamin E concentration of shelf-aged samples did not decrease significantly, the surface vitamin E concentration of samples aged in air and water at 40° C. decreased considerably (FIGS. 29, 30, and 31, respectively). The higher extraction of vitamin E from the surface in the samples aged in water was due to the decrease in the solubility of the UHMWPE at 40° C. compared to 120° C., where it was doped and homogenized and the aqueous environment carrying the extracted vitamin E away from the surface, increasing the driving force.

This Example shows that when stored in air or in water at 40° C., the irradiated and α-tocopherol-doped UHMWPE loses about 10% of the α-tocopherol over about the first six months. The presence of excess α-tocopherol in the joint space may possibly lead to an adverse biological response. Therefore, in order to avoid such complication, it is necessary to extract α-tocopherol from the polymeric material prior to placement and/or implantation into the body. Decreasing the concentration decreases the driving force of the α-tocopherol out of the implant, minimizing further elution.

Example 29

Melting Subsequent to Blending with Vitamin E, Extraction and Irradiation

Vitamin E is blended with UHMWPE powder at a concentration of 0.01, 0.02, 0.05, 0.1, 0.2, 0.5, 1.0, 2.5 or 50 wt %. The blend is then consolidated into Vitamin E-blended blocks (for example, 5 cm by 10 cm by 12 cm) by compression molding.

A Tween 80 solution is prepared in deionized water. A pressure chamber is heated to 100, 110, 120, 130, 140, 150, 160, 170 or 180° C. in an air convection oven. The solution is placed in the heated chamber with the UHMWPE samples and the chamber was sealed. The extraction of vitamin E from this homogenized UHMWPE is done for 5, 20, 50 or 200 hours under self generated pressure. At the end of the 20 hours, the chamber is cooled down to room temperature and the pressure is released.

Alternatively, a Tween 80 emulsion in ethanol is prepared in deionized water. The solution is placed in an Erlenmeyer flask with the UHMWPE samples and is boiled under reflux at ambient pressure.

Alternatively, the samples are boiled in hexane, xylene or ethanol for 5, 20, 50 or 200 hours. Then, they are dried in vacuum or partial vacuum at room temperature or at a temperature up to 137° C. for 1, 2, 3, 4, 5, 6, 7, 8, 9, 10, 12, 13, 14, 15, 16, 17, 18, 19, or days or more.

Some blocks are subsequently irradiated to 25, 50, 75, 100, 125, 150, 200 and 250 kGy using gamma or e-beam irradiation.

Some blocks are heated to above the melting temperature of blended UHMWPE (approximately 137° C. at ambient pressure) and held. The holding time can be 10 minutes to several days. Depending on the amount of time at temperature and the size of the block, some parts or all parts of the block are molten.

Melting of irradiated, vitamin E-containing UHMWPE can change the distribution of vitamin E concentration and also can change the mechanical properties of UHMWPE. These changes can be induced by changes in crystallinity and/or by the plasticization effect of vitamin E at certain concentrations.

Example 30

Melting Subsequent to Doping with Vitamin E, Homogenization Extraction and Irradiation UHMWPE is blended with vitamin E and homogenized. A Tween 80 solution is prepared in deionized water. A pressure chamber is heated to 100, 110, 120, 130, 140, 150, 160, 170 or 180° C. in an air convection oven. The solution is placed in the heated chamber with the UHMWPE samples and the chamber was sealed. The extraction of vitamin E from this homogenized UHMWPE is done for 5, 20, 50 or 200 hours under self generated pressure. At the end of the 20 hours, the chamber is cooled down to room temperature and the pressure is released.

Alternatively, a Tween 80 emulsion in ethanol is prepared in deionized water. The solution is placed in an Erlenmeyer flask with the UHMWPE samples and is boiled under reflux at ambient pressure.

Alternatively, the samples are boiled in hexane, xylene or ethanol for 5, 20, 50 or 200 hours. Then, they are dried in vacuum or partial vacuum at room temperature or at a temperature up to 137° C. for 1, 2, 3, 4, 5, 6, 7, 8, 9, 10, 12, 13, 14, 15, 16, 17, 18, 19, or days.

Some blocks are subsequently irradiated to 25, 50, 75, 100, 125, 150, 200 and 250 kGy using gamma or e-beam irradiation.

Some irradiated blocks are heated to above the melting temperature of blended UHMWPE (approximately 137° C. at ambient pressure) and held. The holding time can be 10 minutes to several days. Depending on the amount of time at temperature and the size of the block, some parts or all parts of the block are molten.

Melting of irradiated, vitamin E-containing UHMWPE can change the distribution of vitamin E concentration and also can change the mechanical properties of UHMWPE. These changes can be induced by changes in crystallinity and/or by the plasticization effect of vitamin E at certain concentrations.

Example 31

Figure 32B:
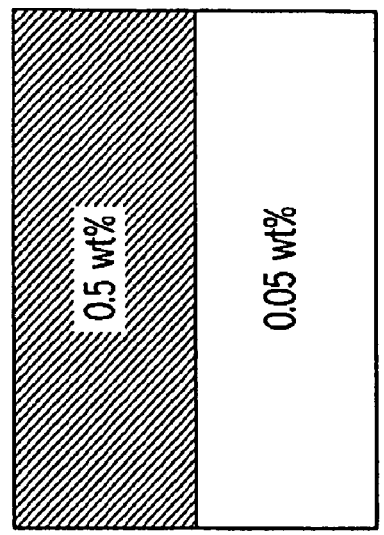
FIG. 32 shows compression molding of UHMWPE resin containing two different concentrations of vitamin E (32a) and the resulting molded UHMWPE block with a spatially controlled gradient in vitamin E concentration (32b).
Figure 32A:
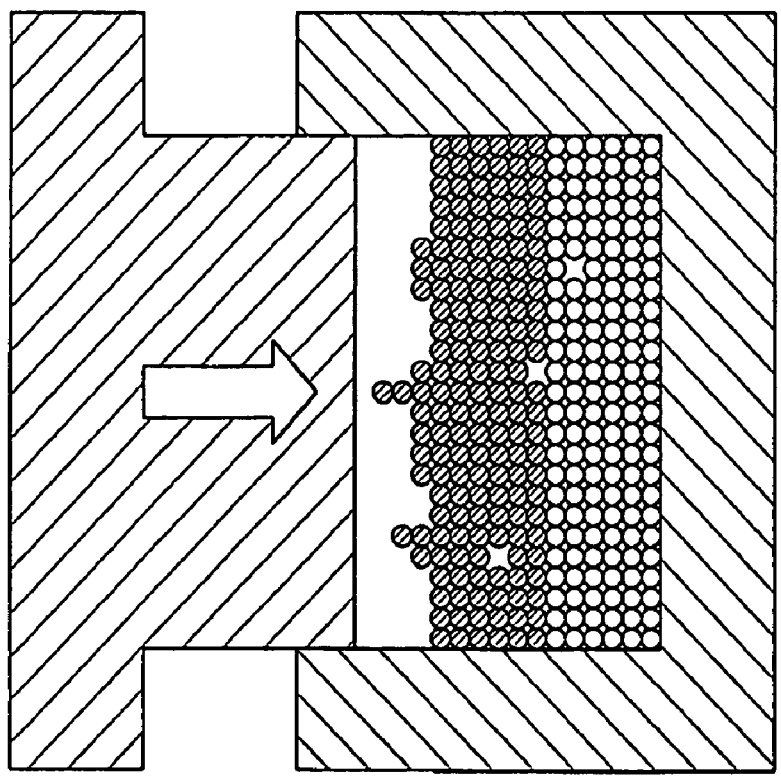

Gradient Cross-Linking by Blending Two Different Vitamin E Concentrations Followed by Irradiation 0.05 wt % vitamin E-containing UHMWPE and 0.5 wt % vitamin E-containing UHMWPE were compression molded to obtain blocks with gradient vitamin E concentration (FIG. 32). These blocks (50 mm diameter parallel to gradient, 38 mm height perpendicular to gradient) were then irradiated by electron beam irradiation at room temperature to 150 kGy in air at 50 kGy/pass.

Figure 33:
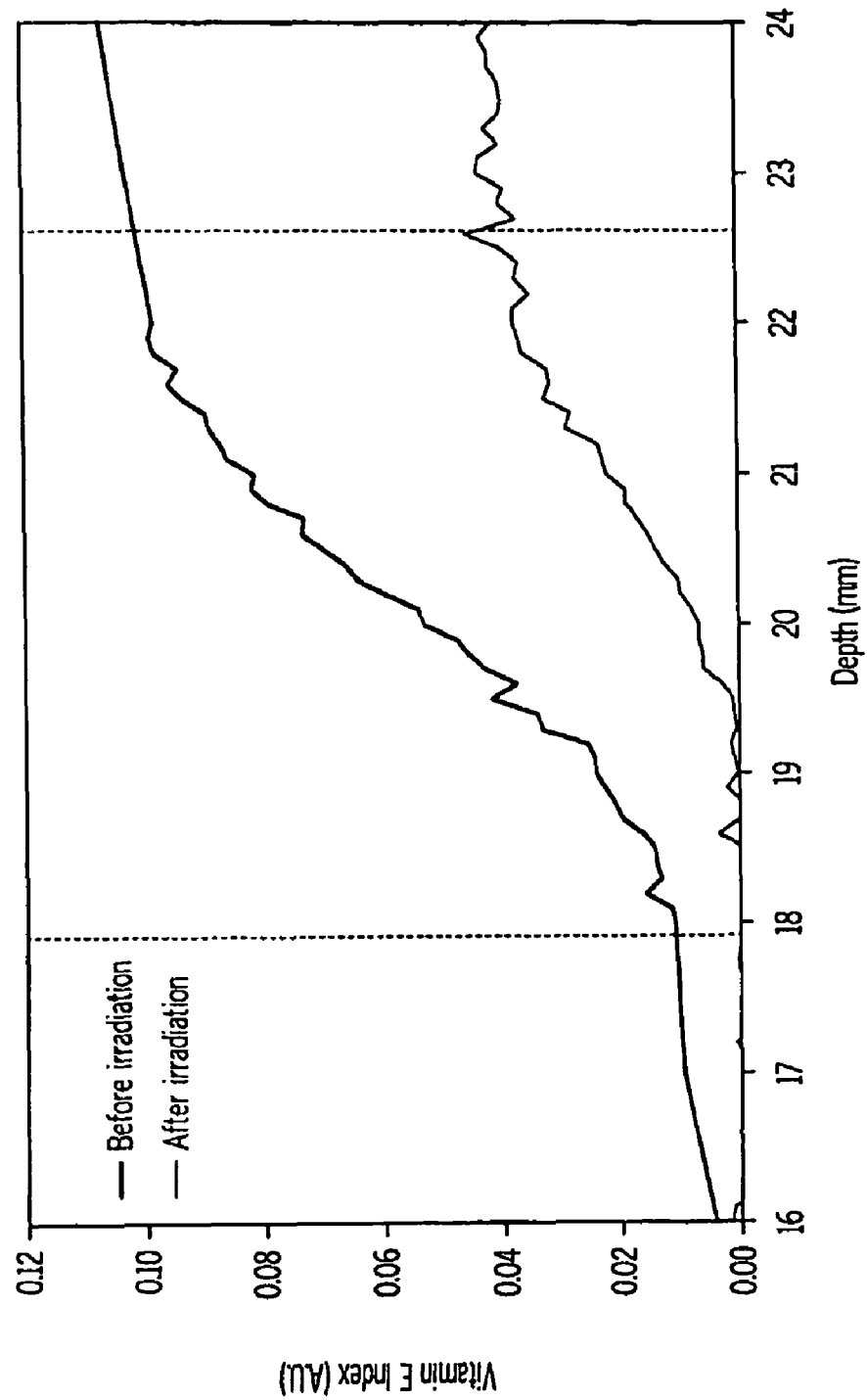
FIG. 33 shows vitamin E concentration of UHMWPE blocks containing a gradient of vitamin E concentration from 0.05 wt % to 0.5 wt % vitamin E as a function of depth. The dotted lines denote the beginning and end of the gradient; to the left of the dotted lines is a homogeneous portion of the sample containing 0.05 wt % vitamin E and to the right of the dotted lines is the homogeneous portion of the sample containing 0.5 wt % vitamin E.

Vitamin E concentration gradient was determined by using Fourier Transform Infrared Spectroscopy (FTIR) as a function of depth away from the surface of the low vitamin E concentration side of the block perpendicular to the gradient. The resulting concentration profiles at the gradient region before and after irradiation are shown in FIG. 33. Since some vitamin E is used during irradiation, the overall index values were decreased after irradiation.

Thin sections were machined out of gradient irradiated UHMWPE perpendicular to the gradient. Cross-link density measurements of gradient cross-linked UHMWPE (n=3 each) were performed on small samples (approximately 3×3×3 mm). The samples were weighed before swelling in xylene at 130° C. and they were weighed in xylene immediately after swelling in xylene. Therefore, the amount of xylene uptake was determined gravimetrically, and then converted to volumetric uptake by dividing by the density of xylene; 0.75 g/cc. By assuming the density of polyethylene to be approximately 0.99 g/cc, the volumetric swell ratio of cross-linked UHMWPE was then determined. The cross-link density was calculated using the swell ratio as described previously (see Muratoglu et al., *Unified Wear Model for Highly Crosslinked Ultra-high Molecular Weight Polyethylenes (UHMWPE). Biomaterials,* 1999. 20(16): p. 1463-1470) and are reported as mol/m$^3$. The cross-link density was determined at three different spatial locations in the sample; (1) in the low vitamin E side, (2) within the span of the gradient; (3) in the high vitamin E side.

Figure 34:
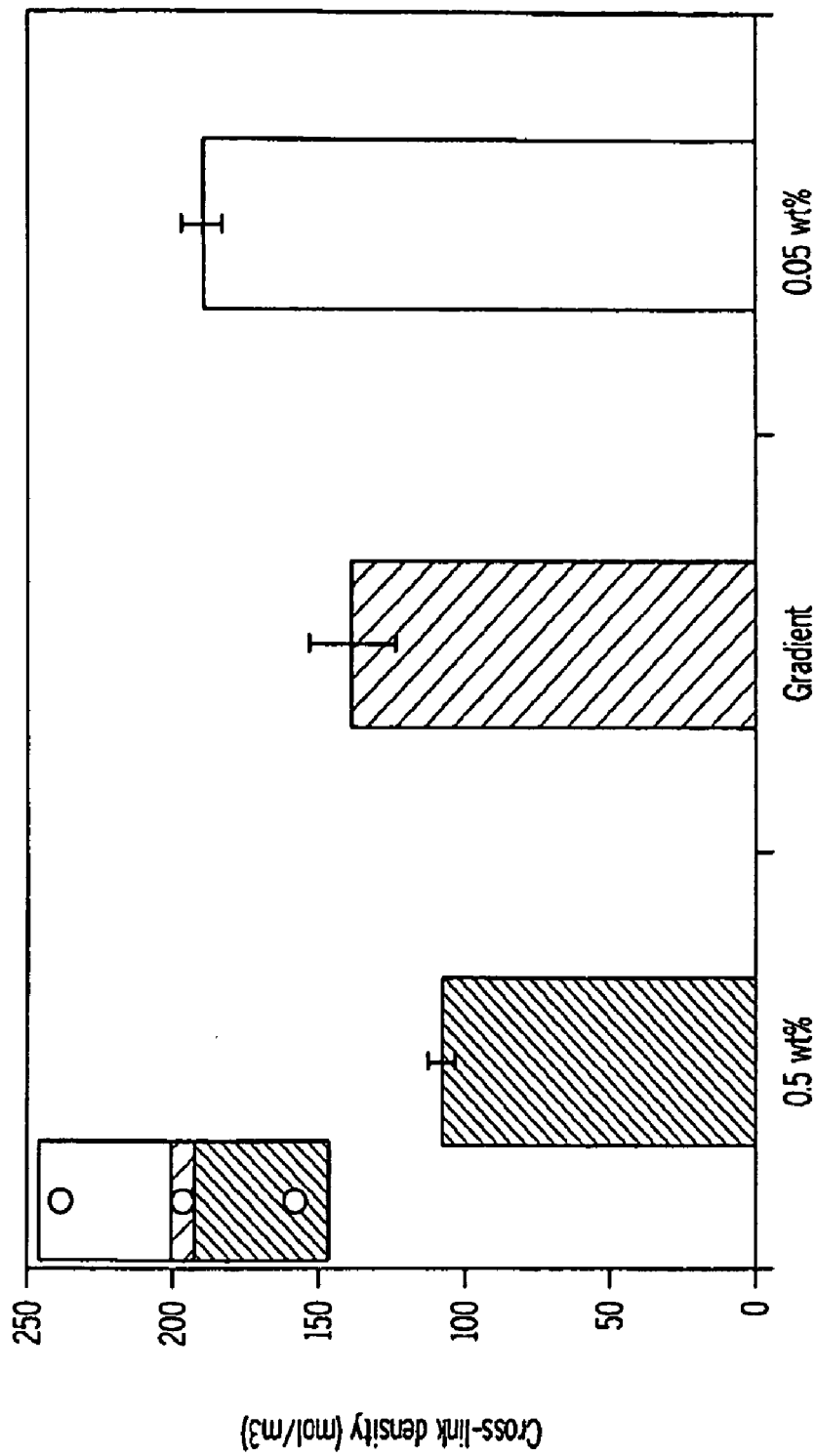
FIG. 34 illustrates cross-link density of the irradiated UHMWPE block at different spatial locations containing different amounts of vitamin E; namely 0.5 wt % vitamin E, within the span of the gradient from 0.5 wt % to 0.05 wt % vitamin E and 0.05 wt % vitamin E. The schematic on the upper left side shows the locations at which cross-link density measurements were made.

Cross-link density results are shown in FIG. 34. As expected, high vitamin E-containing side had low cross-link density due to the free radical scavenging of vitamin E during irradiation, hindering cross-linking. The low vitamin E containing side was highly cross-linked. The cross-linking level in the gradient region was between that of the low and the high side commensurate with the vitamin E concentration.

These results showed that spatially controlled cross-linking could be obtained by obtaining a spatially controlled gradient of vitamin E concentration in UHMWPE prior to irradiation.

Example 32

Interface Strength of Gradient Cross-Linked UHMWPE

The samples containing gradient cross-linking prepared, as described in the Example 31 above, were machined into 3.2 mm thick sections perpendicular to the gradient. From these thin sections, dogbones (Type V, ASTM D638) and tear test samples (The die according to ASTM D1004 was used; however the samples were only 3.8 cm long) were stamped.

Figure 35:
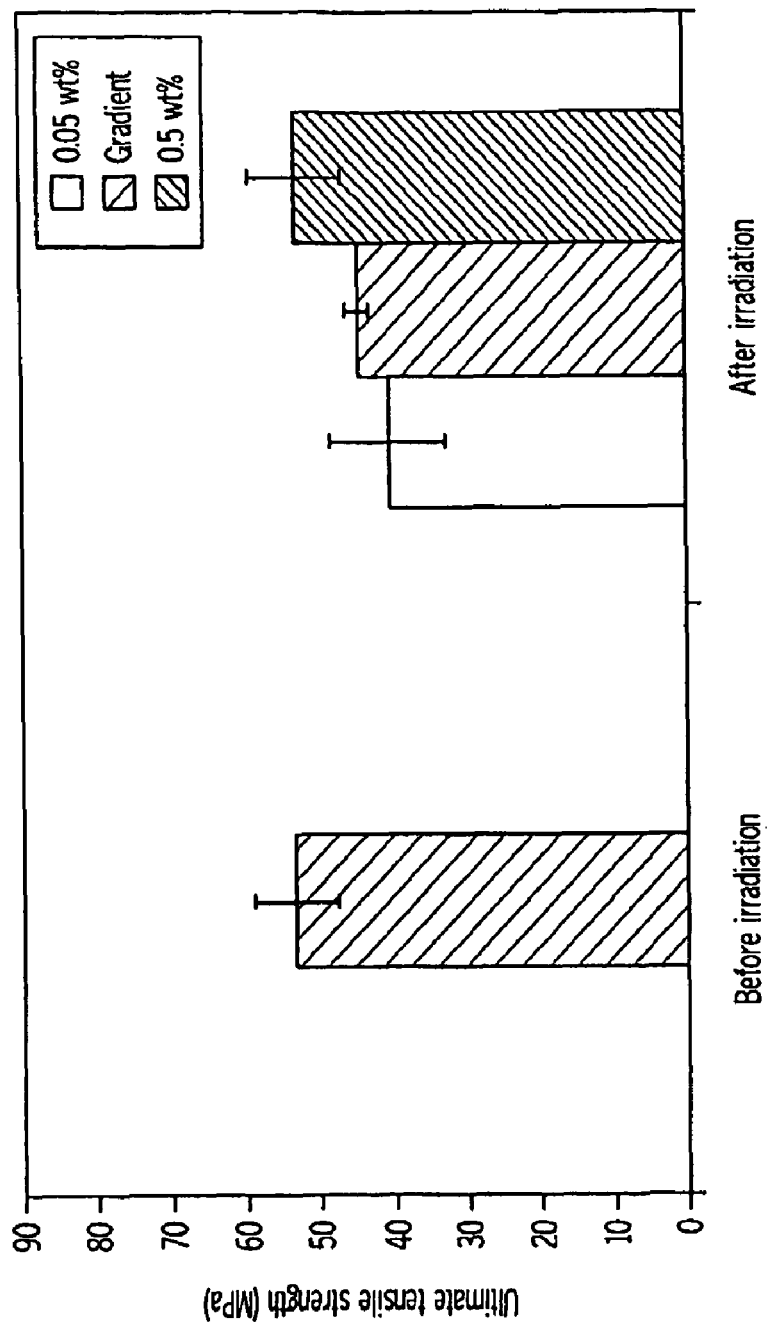
FIG. 35 shows ultimate tensile strength of gradient cross-linked UHMWPE. The schematic on the left shows the stamping location of the tensile dog-bones and the testing direction. Separate UHMWPE molded blocks with homogenous 0.05 wt % or 0.5 wt % vitamin E concentration were used as controls after irradiation.
Figure 35:
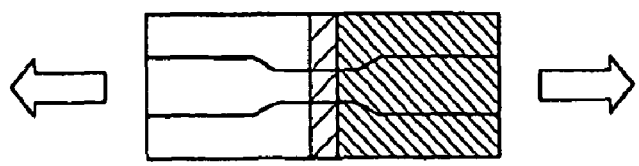
Figure 36:
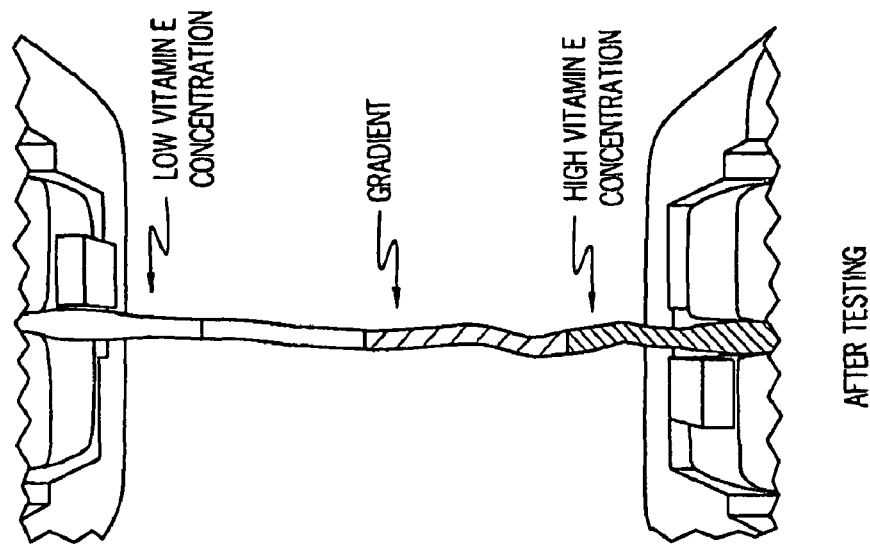
FIG. 36 depicts a representative gradient cross-linked UHMWPE tensile testing specimen before and after testing. The location of the failure and the different regions of the UHMWPE with different concentrations of vitamin E are marked.
Figure 36:
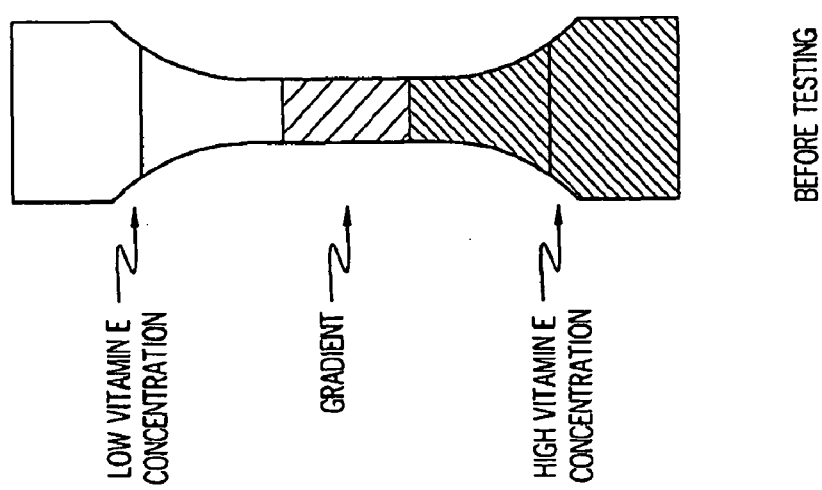

The ultimate tensile strength (UTS) of the high vitamin E-containing UHMWPE was higher than the rest of the samples due to lower cross-link density after irradiation (FIG. 35). In fact, the UTS of this sample was comparable to the gradient sample before irradiation showing that cross-linking was not sufficient to affect the mechanical properties significantly in this sample. In contrast, the UTS of low vitamin E-containing UHMWPE was decreased compared to the gradient sample before irradiation and was the lowest due to high cross-link density. The UTS of the gradient samples were slightly higher than low vitamin E-containing, highly cross-linked UHMWPE. Also, all samples failed within the highly cross-linked region and not at the gradient (FIG. 36).

Figure 37:
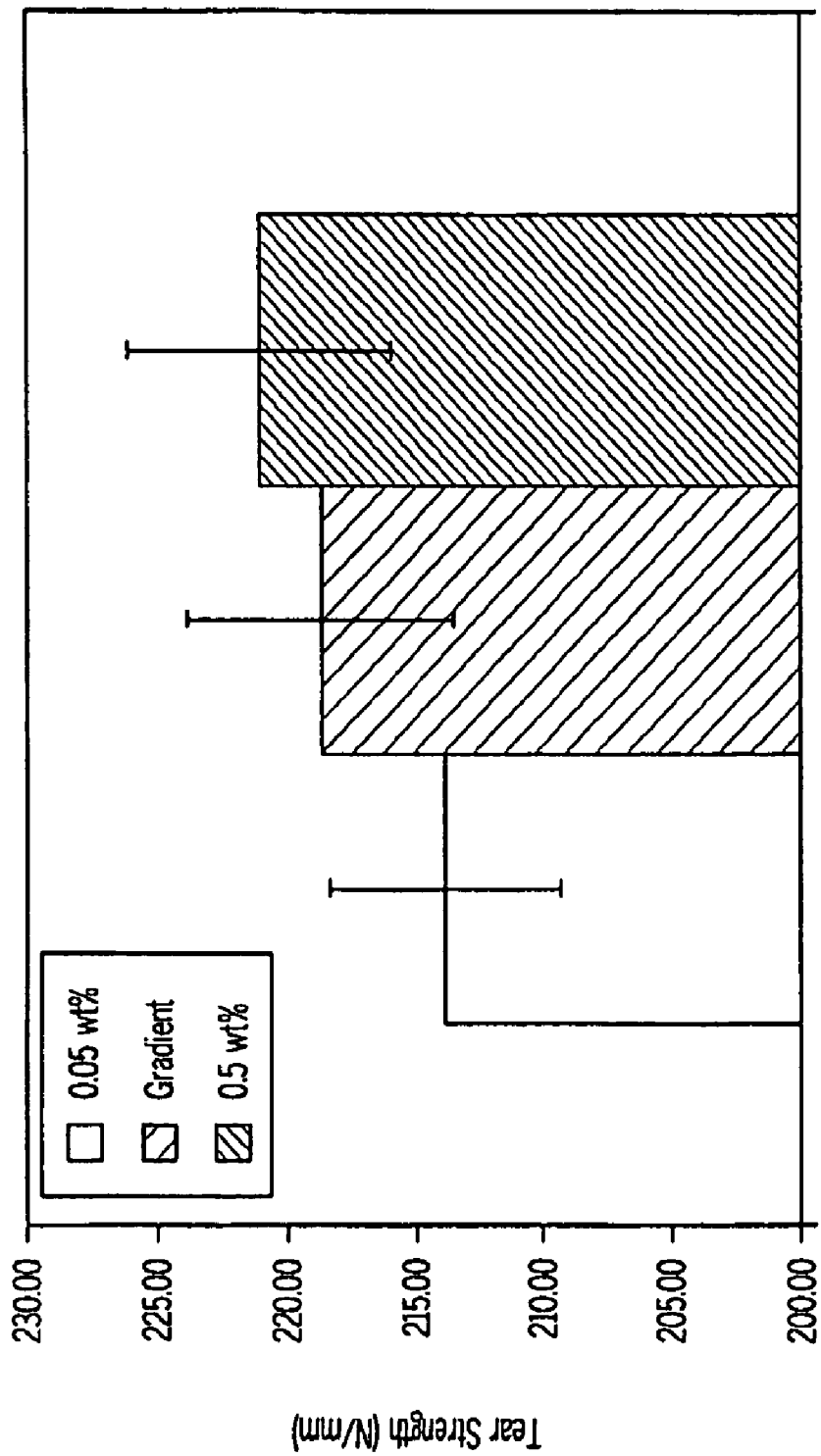
FIG. 37 shows tear strength of gradient cross-linked UHMWPE. The schematic on the left shows the stamping location of the tear test specimens and the testing direction. Separate UHMWPE molded blocks with homogenous 0.05 wt % or 0.5 wt % vitamin E concentration were used as controls after irradiation.

The tear strength of the higher vitamin E-containing UHMWPE was higher than the rest of the samples due to lower cross-link density after irradiation (FIG. 37). In contrast, the tear strength of low vitamin E-containing UHMWPE was decreased compared to the gradient sample before irradiation and was the lowest likely due to high cross-link density. The tear strengths of the gradient samples were higher than low vitamin E-containing, highly cross-linked UHMWPE.

These results showed that the interface strength was at least as high as the strength of the low vitamin E, highly cross-linked UHMWPE and that interface failure did not cause the failure of the sample.

Example 33

Wear Resistance of Gradient Cross-Linked UHMWPE

Figure 38A:
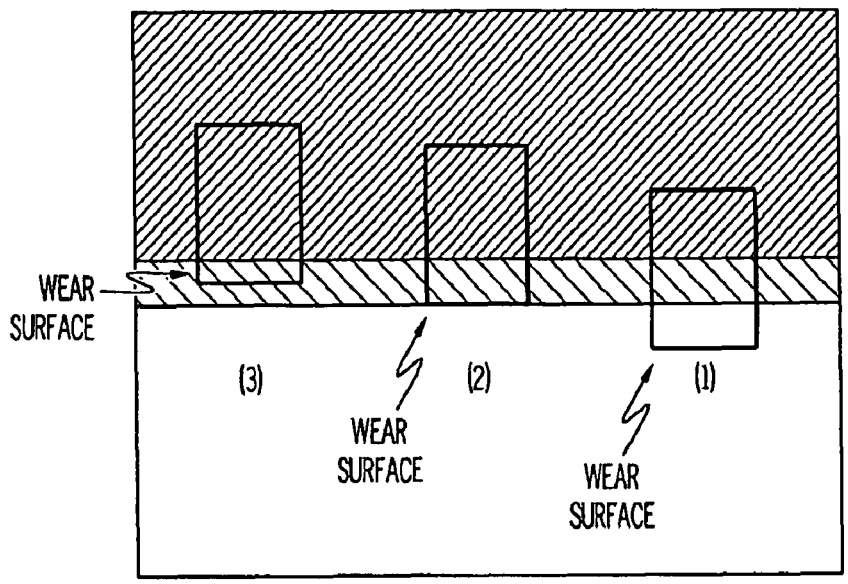
FIG. 38 schematically depicts the location of machined pins with respect to the gradient (38a) and the location of the wear surfaces of the pins with respect to the vitamin E concentration gradient determined by FTIR (38b).
Figure 38B:
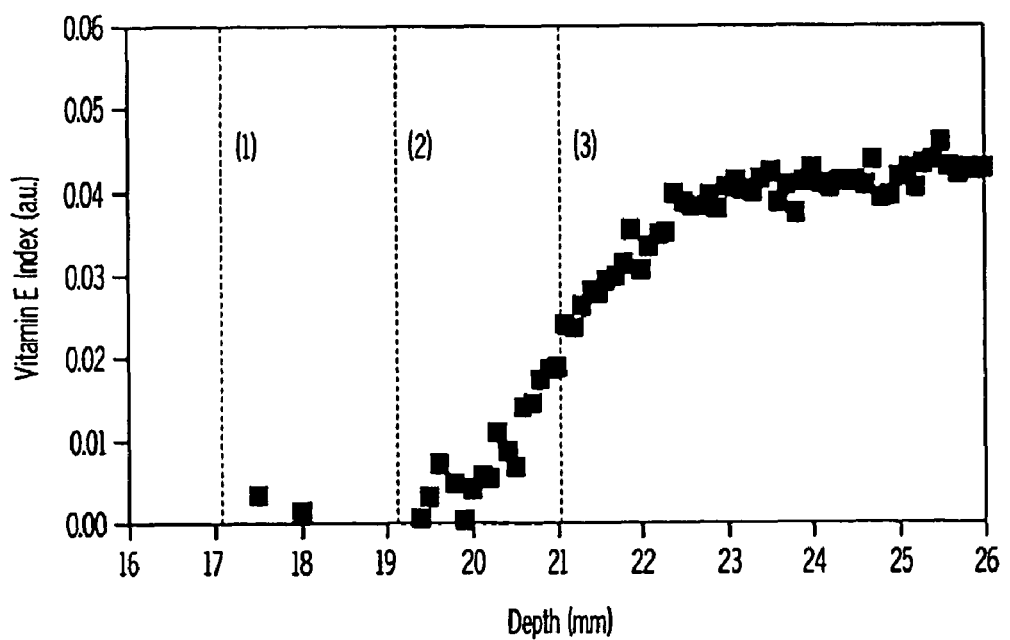

For wear testing, cylindrical pins (9 mm diameter, 13 mm length) were machined with their flat wear surfaces at the middle of the gradient, at the edge of the gradient and 2 mm into the highly cross-linked UHMWPE (FIG. 38).

Wear testing was done on a custom-designed bidirectional pin-on-disc wear tester against CoCr discs for 1 million cycles in undiluted bovine serum with penicillin-streptomycin and EDTA. The wear rate of gradient cross-linked samples were 1.59±0.08 and 3.52±0.91 mg/million-cycles (MC), respectively, for samples 1 and 3 (FIG. 38). These results showed that wear resistance was closely related to cross-link density with the region with high cross-linking resulting in low wear.

Example 34

Manipulation of the Gradient Span

Figure 39A:
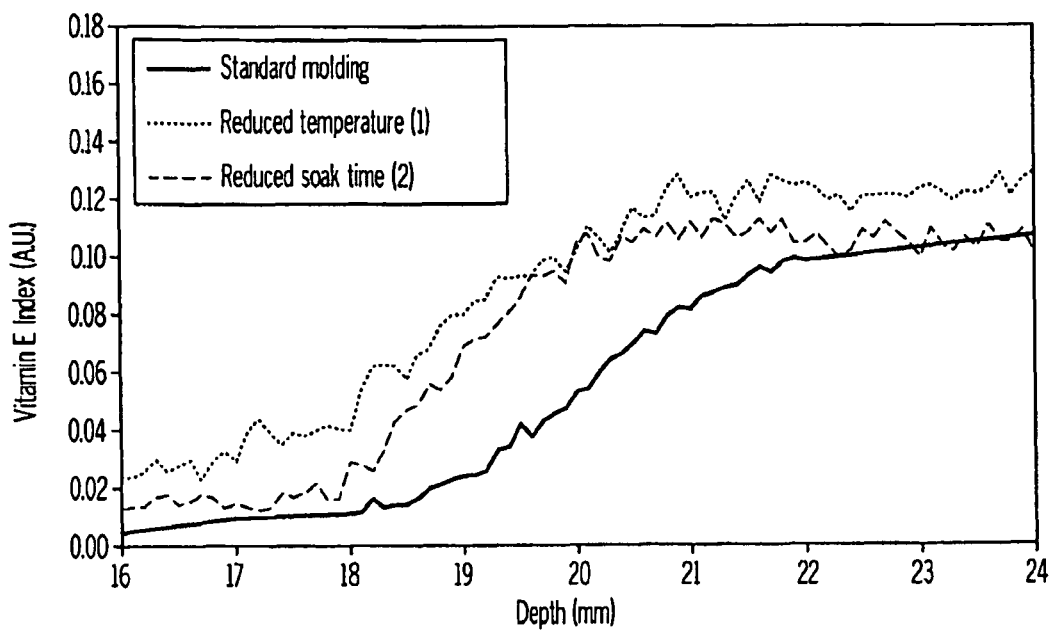
FIG. 39 shows gradient vitamin E profiles of molded vitamin E-blended UHMWPEs; (39a) strategies 1 and 2 with a thin film of molded polyethylene in between the powder, (39b) strategy 3.

The span of the gradient was manipulated by using several different techniques during molding with the process, as shown in FIG. 39(a), such as (1) by reducing the temperature of molding on the 0.5 wt % vitamin E containing side, and (2) by reducing the molding time in addition to placing a thin sheet of previously molded 0.05 wt % vitamin E in between the powder specimens to be molded to reduce the diffusion of vitamin E from the 0.5 wt % to the 0.05 wt % blended powder.

Figure 39B:
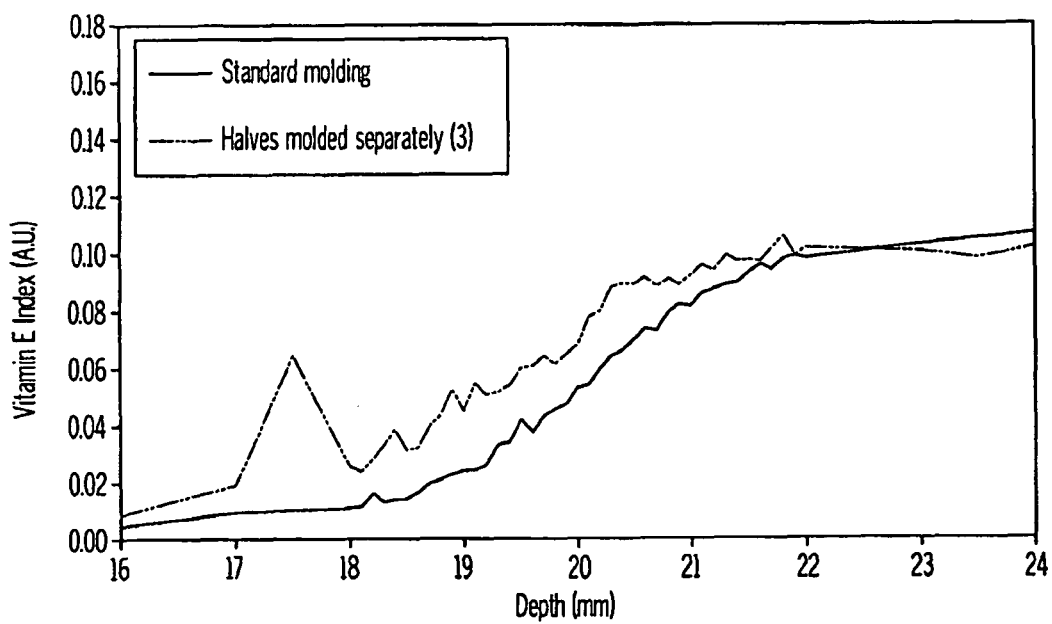

Another strategy was to mold the blocks separately, then place them in the molding chamber and fuse them together (3). The resultant gradient vitamin E profiles are shown in FIG. 39(b).

The span of the gradient was determined to be 4.3 mm for standard molding, 3.0 mm for (1), 3.1 mm for (2) and 3.1 mm for (3). These results show that by using these strategies, the span of the gradient can be reduced.

Example 35

Gradient Cross-Linking by Irradiating Compression Molded Components Made with a Mixture of Virgin UHMWPE Powder and Vitamin E-Blended UHMWPE Powder Four puck-shaped samples (3 in diameter, 0.5 in thickness) made from a mixture of virgin GUR 1050 powder and vitamin E-blended GUR 1050 powder were compression molded in a cylindrical mold at 205° C. The peak load was 9000 lb and the mold was cooled under load. The samples and their compositions are listed in Table 9.

TABLE 9

Compositions of compression-molded vitamin E-UHMWPE pucks.

| | Concentration of Vitamin E-blended powder (wt %) | Wt. of blended powder (g) | Wt. of virgin powder (g) | Overall Vitamin E concentration (wt %) |
|---|---|---|---|---|
| Blend 1 | 10.0 | 1.0 | 49.0 | 0.2 |
| Blend 2 | 5.0 | 2.0 | 48.0 | 0.2 |
| Ctri 1 | 0.2 | 50.0 | 0.0 | 0.2 |
| Ctri 2 | 0.0 | 0.0 | 50.0 | 0.0 |

Two of the samples (Blend1 and Blend2) were made from mixtures of virgin GUR 1050 powder and vitamin e-blended GUR 1050 powder. Two control samples, one containing no vitamin E and the other prepared from pure 0.2 wt % vitamin e-blended powder, were also prepared. All four pucks were irradiated to 100 kGy using gamma irradiation under a vacuum seal.

ASTM D638 (Type V specimens) was used to determine the mechanical properties of the irradiated samples. The sample thickness was 3.2 mm and the strain rate was 100 mm/min. A laser extensometer was used to record the elongation at break. The tensile properties of the samples are shown in Table 10. The values of the ultimate tensile strength (UTS) were similar for all samples within experimental error. Both Blend1 and Blend2 have similar elongation values to Ctrl1, which contained the same overall concentration of vitamin E, but significantly higher elongation values than Ctrl2, which contained no vitamin E. From these results it is clear that the mechanical properties of the inhomogeneously blended samples Blend 1 and Blend2 are equal to or better than the mechanical properties of the homogeneous blend Ctrl1.

TABLE 10

Tensile properties of compression-molded pucks.

| | UTS (MPa) | +/− | Yield (MPa) | +/− | Elongation (%) | +/− |
|---|---|---|---|---|---|---|
| Blend1 | 40.5 | 1.7 | 22.9 | 0.4 | 260 | 6 |
| Blend2 | 43.5 | 1.2 | 23.2 | 0.2 | 274 | 7 |
| Ctrl1 | 42.0 | 1.8 | 22.7 | 0.2 | 271 | 17 |
| Ctrl2 | 41.9 | 2.0 | 22.5 | 0.2 | 211 | 9 |

Example 36

Gradient Cross-Linking by Irradiating Compression Molded Components Made with a Mixture of Virgin UHMWPE Powder and Vitamin E-Blended UHMWPE Pellets A puck-shaped sample (3 in diameter, 0.5 in thickness) made from a mixture of virgin GUR 1050 powder (43.6 g) and vitamin E-blended pellets (11.0 g, pellets contained 5 wt % vitamin E) was compression molded in a cylindrical mold at 205° C. The vitamin E-blended pellets were prepared from vitamin E-blended powder (5 wt % vitamin E) that was consolidated into small discs (1 in diameter, 0.125 in thick). The discs were then chopped up with a razor-blade into small cubes approximately 4 mm (⅛ in) on a side. These pellets were then mixed by hand with the virgin UHMWPE powder and consolidated. The peak load was 9000 lb and the mold was cooled under load. The puck had obvious inhomogeneities in vitamin E concentration which were visible to the naked eye.

The as-molded puck (Blend3) and a control containing no vitamin E (Ctrl) were irradiated to 100 kGy using gamma irradiation under a vacuum seal. After irradiation, both pucks were annealed in argon at 130° C. for 96 hours to homogenize the vitamin E concentration in the puck. The samples and their compositions are listed in Table 11.

The mechanical properties of the Blend3 sample, prepared from a virgin powder/vitamin E-containing UHMWPE pellet mixture, are vastly superior to the mechanical properties of the control sample, which contains no vitamin E. In particular, the yield stress and the elongation both show statistically significant enhancements.

TABLE 11

Tensile properties of compression-molded pucks.

| | UTS (MPa) | +/− | Yield (MPa) | +/− | Elongation (%) | +/− |
|---|---|---|---|---|---|---|
| Blend3 | 42.9 | 6.1 | 24.4 | 0.3 | 308 | 33 |
| Ctrl | 41.9 | 2.0 | 22.5 | 0.2 | 211 | 9 |

Example 37

Gradient Preparation by Extracting a Vitamin E Blended UHMWPE by Organic or Aqueous Solvents One block (approximately 1 cm cube) each of 0.3 and 0.5 wt % vitamin E blended GUR1050 UHMWPE were boiled in hexane for 1, 2, 4, 6, 24 and 40 hours followed by vacuum drying in a vacuum oven at room temperature for 7-10 days.

Fourier Transform Infrared Spectroscopy (FTIR) was performed on thin sections (approximately 150 μm) cut using a sledge microtome. Infrared spectra were collected from one edge of the sample to the other in 100 μm and 500 μm intervals, with each spectrum recorded as an average of 32 individual scans. The infrared spectra were analyzed to calculate a vitamin E index as the ratio of the areas under the α-tocopherol absorbance at 1262 cm$^{-1}$ (1245-1275 cm$^{-1}$) and the polyethylene skeletal absorbance at 1895 cm$^{-1}$ (1850-1985 cm$^{-1}$). The vitamin E index was plotted as a function of distance away from the surface to present the vitamin E concentration profiles of the extracted samples.

Figure 40A:
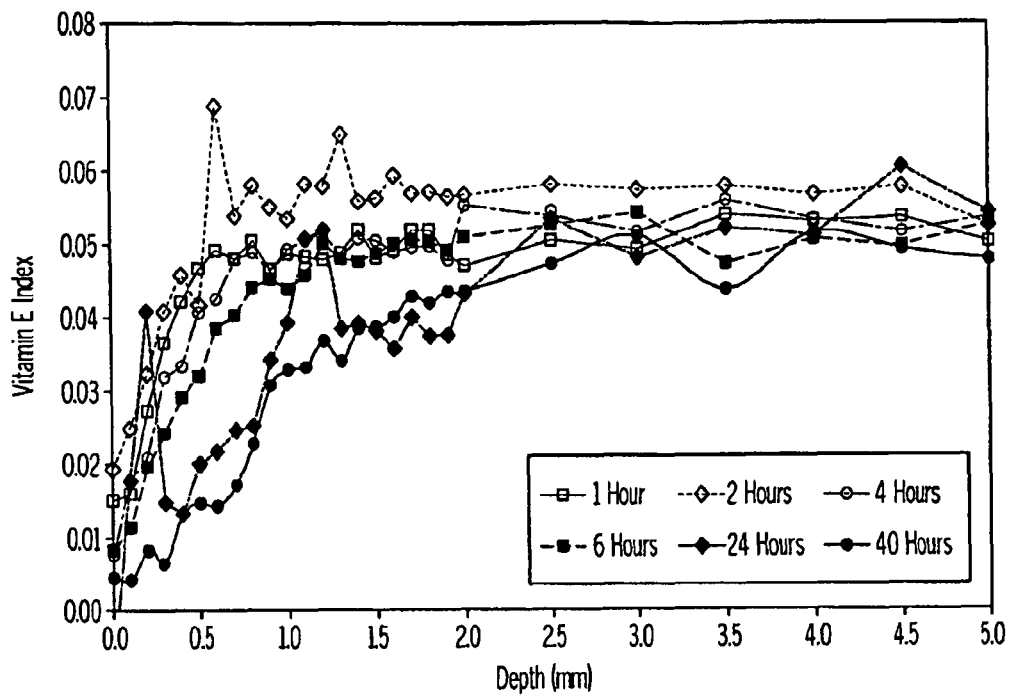
FIG. 40 illustrates vitamin E profiles of 0.3 wt % (40a) and 0.5 wt % (40b) vitamin E-blended UHMWPE extracted in boiling hexane for various durations.
Figure 40B:
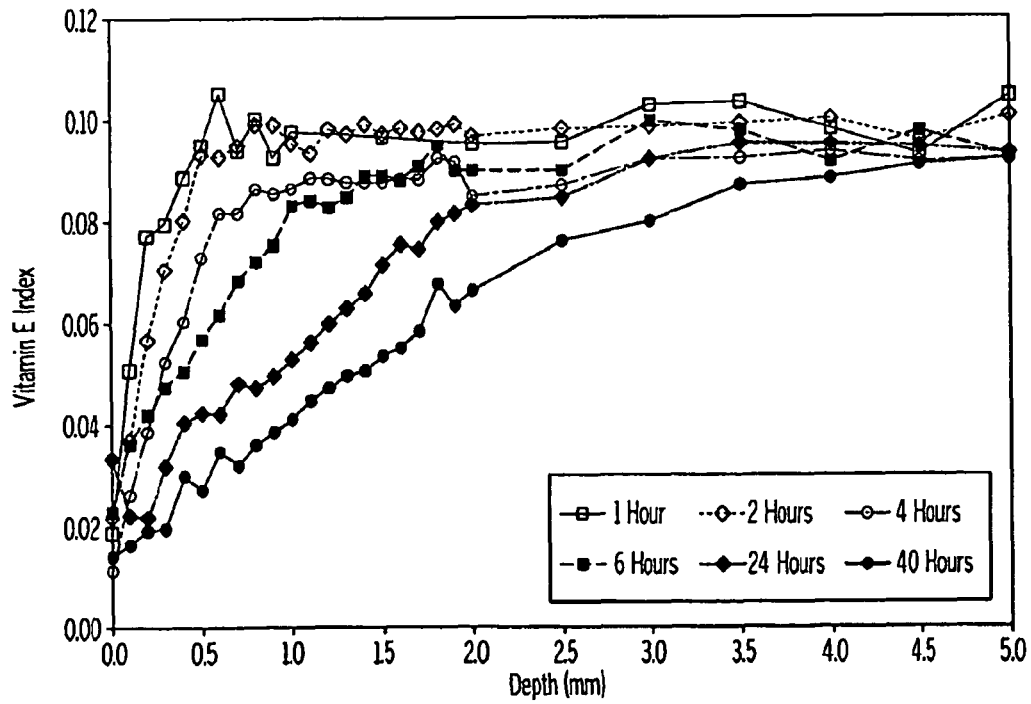

The span of the gradient (FIG. 40) was calculated from the surface to where the vitamin E index did not appreciably change for three consecutive data points. The results in Table 12 showed that using this extraction method, creating vitamin E gradients with spans ranging from 0.5 mm to 5 mm was possible.

TABLE 12

Approximate span of the vitamin E gradient from the surface of blended and hexane extracted UHMWPE.

| Extraction time | Approximate gradient span (mm) | |
| --- | --- | --- |
| (hrs) | 0.3 wt % | 0.5 wt % |
| 1 | 0.6 | 0.5 |
| 2 | 0.6 | 0.5 |
| 4 | 0.7 | 0.8-1.4 |
| 6 | 1.5 | 1.7 |
| 24 | 2.5 | 3.0 |
| 40 | 3-4 | 4.5 |

Similarly, one block (approximately 1 cm cubes) each of 0.3 and 0.5 wt % vitamin E blended GUR1050 UHMWPE were boiled in a 10% Tween 80 (polysorbate 80/polyoxyethylene sorbitan monooleate) solution or a 15% Tween 80/5% ethanol solution for 6 hours followed by vacuum drying in a vacuum oven at room temperature for a day.

The extraction by aqueous Tween 80 solution resulted in a narrower span than the hexane extracted samples (Tables 12 and 13).

TABLE 13

Approximate span of the vitamin E gradient from the surface of blended and aqueous Tween 80 solution-extracted UHMWPE.

| Extraction solvent | Extraction time (hrs) | Approximate gradient span (mm) | |
| --- | --- | --- | --- |
| | | 0.3 wt % | 0.5 wt % |
| Tween 80 | 6 | 0.7 | 0.7 |
| Tween 80/ethanol | 6 | 0.8 | 0.9 |

The experimental results indicate that by extracting in organic or aqueous solution from the surface of a blended UHMWPE, a gradient concentration profile of vitamin E can be obtained. These samples can further be irradiated to obtain a gradient cross-linked UHMWPE with high cross-linking on the surface and low cross-linking in the bulk.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of making an oxidation-resistant cross-linked polymeric material comprising:
   a) doping a consolidated polymeric material with an antioxidant at a temperature below or above the melting point of the polymeric material, wherein the surface of the polymeric material is contacted with lower concentration antioxidant and bulk of the polymeric material is contacted with a higher concentration of antioxidant than the first portion, thereby allowing a spatial distribution of the antioxidant-rich and antioxidant-poor regions; and
   b) irradiating the consolidated polymeric material containing the spatially distributed antioxidant with ionizing radiation, thereby forming an oxidation-resistant cross-linked polymeric material having a spatially controlled cross-linking and antioxidant distribution.

2. A method of making an oxidation-resistant cross-linked polymeric material comprising:
   a) doping a consolidated polymeric material with an antioxidant at a temperature below or above the melting point of the polymeric material, wherein the bulk of the polymeric material is contacted with lower concentration antioxidant and surface of the polymeric material is contacted with a higher concentration of antioxidant than the bulk, thereby allowing a spatial distribution of the antioxidant-rich and antioxidant-poor regions; and
   b) irradiating the consolidated polymeric material containing the spatially distributed antioxidant with ionizing radiation, thereby forming an oxidation-resistant cross-linked polymeric material having a spatially controlled cross-linking and antioxidant distribution.

3. A method of making an oxidation-resistant cross-linked polymeric material comprising:
   a) doping a consolidated polymeric material with an antioxidant at a temperature below or above the melting point of the polymeric material,
   b) annealing the antioxidant-doped polymeric material by heating to below or above the melt, thereby allowing a spatial distribution of the antioxidant-rich and antioxidant-poor regions; and
   c) irradiating the consolidated polymeric material containing the spatially distributed antioxidant with ionizing radiation, thereby forming an oxidation-resistant cross-linked polymeric material having a spatially controlled cross-linking and antioxidant distribution.

4. A method of making a medical implant comprising an oxidation-resistant cross-linked medical implant comprising:
   a) doping a consolidated polymeric material with an antioxidant at a temperature below or above the melting point of the polymeric material, wherein the surface of the polymeric material is contacted with lower concentration antioxidant and bulk of the polymeric material is contacted with a higher concentration of antioxidant than the surface, thereby allowing a spatial distribution of the antioxidant-rich and antioxidant-poor regions;
   b) irradiating the consolidated polymeric material containing the spatially distributed antioxidant with ionizing radiation, thereby forming a cross-linked polymeric material having a spatial distribution of oxidation-resistant regions; and
   c) machining the consolidated and antioxidant-doped cross-linked polymeric material, thereby forming a medical implant having a spatial distribution of oxidation-resistant regions.

5. A method of making a medical implant comprising an oxidation-resistant cross-linked medical implant comprising:

a) doping a consolidated polymeric material with an antioxidant at a temperature below or above the melting point of the polymeric material, wherein the bulk of the polymeric material is contacted with lower concentration antioxidant and surface of the polymeric material is contacted with a higher concentration of antioxidant than the bulk, thereby allowing a spatial distribution of the antioxidant-rich and antioxidant-poor regions;
b) irradiating the consolidated polymeric material containing the spatially distributed antioxidant with ionizing radiation, thereby forming a cross-linked polymeric material having a spatial distribution of oxidation-resistant regions; and
c) machining the consolidated and antioxidant-doped cross-linked polymeric material, thereby forming a medical implant having a spatial distribution of oxidation-resistant regions.

6. A method of making an oxidation-resistant cross-linked polymeric material comprising:
a) doping a consolidated polymeric material with an antioxidant at a temperature below or above the melting point of the polymeric material;
b) annealing the antioxidant-doped polymeric material by heating to below or above the melt, thereby allowing a spatial distribution of the antioxidant-rich and antioxidant-poor regions;
c) irradiating the consolidated polymeric material containing the spatially distributed antioxidant with ionizing radiation, thereby forming an oxidation-resistant cross-linked polymeric material having a spatially controlled antioxidant distribution; and
d) machining the consolidated and antioxidant-doped cross-linked polymeric material, thereby forming a medical implant having a spatially controlled distribution of oxidation-resistant regions.

7. A method of making an oxidation-resistant cross-linked polymeric material comprising:
a) blending a polymeric material with an antioxidant, wherein a first portion of the polymeric material is contacted with lower concentration antioxidant and a second portion of the polymeric material is contacted with a higher concentration of antioxidant than the first portion, thereby allowing a spatial distribution of the antioxidant-rich and antioxidant-poor regions;
b) consolidating the antioxidant blended polymeric material, thereby forming a medical implant preform; and
c) irradiating the medical implant preform containing the spatially distributed antioxidant with ionizing radiation, thereby forming a medical implant preform having an oxidation-resistant cross-linked polymeric material having a spatially controlled cross-linking and antioxidant distribution.

8. A method of making a medical implant comprising an oxidation-resistant cross-linked polymeric material made by a process comprising the steps of:
a) blending a polymeric material with an antioxidant such that a first portion of the polymeric material is contacted with lower concentration antioxidant and a second portion of the polymeric material is contacted with a higher concentration of antioxidant than the first portion, thereby allowing a spatial distribution of the antioxidant-rich and antioxidant-poor regions;
b) consolidating the antioxidant blended polymeric material, thereby forming a medical implant preform;
c) irradiating the medical implant preform containing the spatially distributed antioxidant with ionizing radiation, thereby forming an oxidation-resistant cross-linked medical implant preform having a spatially controlled antioxidant distribution; and
d) machining the oxidation-resistant cross-linked medical implant preform having the spatially controlled antioxidant distribution, thereby forming an oxidation-resistant cross-linked medical implant having a spatially controlled cross-linking and antioxidant distribution.

9. A method of making a medical implant comprising an oxidation-resistant cross-linked polymeric material made by a process comprising the steps of:
a) blending a polymeric material with an antioxidant, wherein a first portion of the polymeric material is contacted with lower concentration antioxidant and a second portion of the polymeric material is contacted with a higher concentration of antioxidant than the first portion, thereby allowing a spatial distribution of the antioxidant-rich and antioxidant-poor regions;
b) consolidating the antioxidant blended polymeric material, thereby forming a medical implant preform;
c) machining the medical implant preform having a spatial distribution of antioxidant, thereby forming an oxidation-resistant medical implant having a spatially controlled antioxidant distribution; and
d) irradiating the oxidation-resistant medical implant preform containing the spatially distributed antioxidant with ionizing radiation, thereby forming an oxidation-resistant cross-linked medical implant having a spatially controlled antioxidant distribution.

10. A method of making an oxidation-resistant cross-linked medical implant comprising:
a) blending one or more types of resin, flakes, or powder with different concentrations of an antioxidant, wherein a first portion of the resin, flakes, or powder are contacted with lower concentration antioxidant and a second portion of the resin, flakes, or powder are contacted with a higher concentration of antioxidant the first portion, thereby allowing a spatial distribution of the antioxidant-rich and antioxidant-poor regions;
b) consolidating the antioxidant-blended resin, flakes, or powder, thereby forming a medical implant preform;
c) irradiating the oxidation-resistant medical implant preform containing the spatially distributed antioxidant with ionizing radiation, thereby forming an oxidation-resistant medical implant preform having a spatially controlled cross-linking and antioxidant distribution; and
d) machining the medical implant preform having a spatial distribution of cross-linking and antioxidant, thereby forming an oxidation-resistant medical implant having a spatially controlled cross-linking and antioxidant distribution.

11. A method of making an oxidation-resistant cross-linked polymeric material comprising:
a) blending a polymeric material with an antioxidant;
b) consolidating the antioxidant-blended polymeric material, thereby forming an oxidation-resistant polymeric material;
c) irradiating the consolidated oxidation-resistant polymeric material with ionizing radiation, thereby forming an oxidation-resistant cross-linked polymeric material; and
d) extracting or eluting the antioxidant from the surface regions of the oxidation-resistant cross-linked polymeric material, thereby preventing or minimizing in vivo elution of the antioxidant.

12. A method of making a medical implant comprising an oxidation-resistant cross-linked polymeric material made by a process comprising the steps of:
  a) blending a polymeric material with an antioxidant;
  b) consolidating the antioxidant-blended polymeric material, thereby forming an oxidation-resistant consolidated polymeric material;
  c) irradiating the consolidated oxidation-resistant polymeric material with ionizing radiation, thereby forming an oxidation-resistant cross-linked consolidated polymeric material;
  d) machining the consolidated and antioxidant-resistant cross-linked polymeric material, thereby forming an oxidation-resistant cross-linked medical implant having oxidation-resistant regions; and
  e) extracting or eluting the antioxidant from the surface regions of the oxidation-resistant cross-linked medical implant, thereby preventing or minimizing in vivo elution of the antioxidant from the oxidation-resistant cross-linked medical implant.

13. A method of making an oxidation-resistant cross-linked medical implant preform comprising:
  a) blending a polymeric material with an antioxidant;
  b) consolidating the antioxidant-blended polymeric material, thereby forming an oxidation-resistant medical implant preform;
  c) irradiating the oxidation-resistant medical implant preform with ionizing radiation, thereby forming a medical implant preform having an oxidation-resistant cross-linked polymeric material; and
  d) extracting or eluting the antioxidant from the surface regions of the oxidation-resistant cross-linked polymeric material, thereby preventing or minimizing in vivo elution of the antioxidant.

14. A method of making a medical implant comprising an oxidation-resistant cross-linked polymeric material made by a process comprising the steps of:
  a) blending a polymeric material with an antioxidant;
  b) consolidating the antioxidant-blended polymeric material, thereby forming an oxidation-resistant consolidated polymeric material;
  c) machining the consolidated and antioxidant-resistant polymeric material, thereby forming an oxidation-resistant medical implant;
  d) irradiating the oxidation-resistant medical implant with ionizing radiation, thereby forming an oxidation-resistant cross-linked medical implant; and
  e) extracting or eluting the antioxidant from the surface regions of the oxidation-resistant cross-linked medical implant prior to placement and/or implantation into the body, thereby preventing or minimizing in vivo elution of the antioxidant from the oxidation-resistant cross-linked medical implant.

15. A method of making an oxidation-resistant cross-linked polymeric material comprising:
  a) doping a consolidated polymeric material with an antioxidant below or above the melting point of the polymeric material, thereby forming an oxidation-resistant polymeric material;
  b) irradiating the consolidated oxidation-resistant polymeric material with ionizing radiation, thereby forming an oxidation-resistant cross-linked consolidated polymeric material; and
  c) extracting or eluting the antioxidant from the surface regions of the oxidation-resistant cross-linked consolidated polymeric material, thereby preventing or minimizing in vivo elution of the antioxidant.

16. A method of making an oxidation-resistant cross-linked medical implant comprising:
  a) doping a consolidated polymeric material with an antioxidant above or below the melting point of the polymeric material, thereby forming an oxidation-resistant polymeric material;
  b) irradiating the consolidated oxidation-resistant polymeric material with ionizing radiation, thereby forming an oxidation-resistant cross-linked consolidated polymeric material;
  c) machining the consolidated and antioxidant-resistant polymeric material, thereby forming an oxidation-resistant cross-linked medical implant; and
  d) extracting or eluting the antioxidant from the surface regions of the oxidation-resistant cross-linked medical implant prior to placement and/or implantation into the body, thereby preventing or minimizing in vivo elution of the antioxidant.

17. A method of making an oxidation-resistant cross-linked polymeric material comprising:
  a) blending a polymeric material with an antioxidant;
  b) consolidating the antioxidant-blended polymeric material, thereby forming an oxidation-resistant polymeric material;
  c) extracting or eluting the antioxidant from the surface regions of the oxidation-resistant polymeric material; and d) irradiating the consolidated oxidation-resistant polymeric material with ionizing radiation, thereby forming an oxidation-resistant cross-linked polymeric material.

18. A method of making a medical implant comprising an oxidation-resistant cross-linked polymeric material made by a process comprising the steps of:
  a) blending a polymeric material with an antioxidant;
  b) consolidating the antioxidant-blended polymeric material, thereby forming an oxidation-resistant consolidated polymeric material;
  c) extracting or eluting the antioxidant from the surface regions of the oxidation-resistant consolidated polymeric material, thereby preventing or minimizing in vivo elution of the antioxidant from the consolidated polymeric material;
  d) irradiating the consolidated oxidation-resistant polymeric material with ionizing radiation, thereby forming an oxidation-resistant cross-linked consolidated polymeric material; and
  e) machining the consolidated and antioxidant-resistant cross-linked polymeric material, thereby forming an oxidation-resistant cross-linked medical implant.

19. A method of making an oxidation-resistant cross-linked medical implant preform comprising:
  a) blending a polymeric material with an antioxidant;
  b) consolidating the antioxidant-blended polymeric material, thereby forming an oxidation-resistant medical implant preform;
  c) extracting or eluting the antioxidant from the surface regions of the oxidation-resistant polymeric material, thereby preventing or minimizing in vivo elution of the antioxidant;
  d) irradiating the oxidation-resistant medical implant preform with ionizing radiation, thereby forming a medical implant preform having an oxidation-resistant cross-linked polymeric material.

20. A method of making a medical implant comprising an oxidation-resistant cross-linked polymeric material made by a process comprising the steps of:
   a) blending the polymeric material with an antioxidant;
   b) consolidating the antioxidant-blended polymeric material, thereby forming an oxidation-resistant consolidated polymeric material;
   c) machining the consolidated and antioxidant-resistant polymeric material, thereby forming an oxidation-resistant medical implant;
   d) extracting or eluting the antioxidant from the surface regions of the oxidation-resistant medical implant, thereby preventing or minimizing in vivo elution of the antioxidant from the oxidation-resistant medical implant; and
   e) irradiating the oxidation-resistant medical implant with ionizing radiation, thereby forming an oxidation-resistant cross-linked medical implant.

21. A method of making an oxidation-resistant cross-linked polymeric material comprising:
   a) doping a consolidated polymeric material with an antioxidant above or below the melting point of the polymeric material, thereby forming an oxidation-resistant polymeric material;
   b) extracting or eluting the antioxidant from the surface regions of the oxidation-resistant consolidated polymeric material, thereby preventing or minimizing in vivo elution of the antioxidant; and
   c) irradiating the consolidated oxidation-resistant polymeric material with ionizing radiation, thereby forming an oxidation-resistant cross-linked consolidated polymeric material.

22. A method of making an oxidation-resistant cross-linked medical implant comprising:
   a) doping a consolidated polymeric material with an antioxidant, thereby forming an oxidation-resistant polymeric material;
   b) machining the consolidated and antioxidant-resistant polymeric material, thereby forming an oxidation-resistant medical implant;
   c) extracting or eluting the antioxidant from the surface regions of the oxidation-resistant medical implant, thereby preventing or minimizing in vivo elution of the antioxidant; and
   d) irradiating the oxidation-resistant medical implant with ionizing radiation, thereby forming an oxidation-resistant cross-linked medical implant.

23. A method of making an oxidation-resistant cross-linked medical implant comprising:
   a) blending one or more types of resin, flakes, or powder with an antioxidant;
   b) consolidating the antioxidant-blended resin, flakes, or powder, thereby forming a medical implant preform;
   c) extracting or eluting the antioxidant from the surface regions of the oxidation-resistant medical implant preform, thereby preventing or minimizing in vivo elution of the antioxidant;
   d) irradiating the oxidation-resistant medical implant preform with ionizing radiation, thereby forming an oxidation-resistant cross-linked medical implant preform; and
   e) machining the oxidation-resistant cross-linked medical implant preform, thereby forming an oxidation-resistant cross-linked medical implant.

24. The method according to claim 7, wherein the oxidation-resistant medical implant preform is further homogenized following the irradiation step by heating to below or above the melt to allow diffusion of the antioxidant from the antioxidant-rich to antioxidant-poor regions and oxidative stability throughout the medical implant.

25. The method according to claim 7, wherein the oxidation-resistant, antioxidant-doped polymeric material or medical implant is homogenized before and/or after irradiation, by thermally treating at a temperature above or below the melting point of the oxidation-resistant, antioxidant-doped polymeric material.

26. The method according to claim 7, wherein the oxidation-resistant polymeric material or the medical implant is further doped with an antioxidant at a temperature below or above the melting point of the polymeric material.

27. The method according to claim 7, wherein a portion or all of the oxidation-resistant polymeric material or medical implant is further thermally treated above the melting point of the polymeric material or medical implant.

28. The method according to claim 7, where in the oxidation-resistant polymeric material or medical implant is further high pressure crystallized by the steps comprising:
   a) heating to above the melting point of the polymeric material;
   b) pressurizing the heated polymeric material to at least 0.001-1000 MPa;
   c) keeping at this pressure and temperature;
   d) cooling down to below the melting point of the polymeric material under pressure; and
   e) releasing the pressure to about ambient pressure.

29. The method according to claim 7, where in the oxidation-resistant polymeric material or medical implant is further high pressure crystallized by the steps comprising:
   a) pressurizing the polymeric material to at least 0.001-1000 MPa;
   b) heating the pressurized polymeric material to below the melting point of the pressurized polymeric material;
   c) keeping at this pressure and temperature;
   d) cooling down to below the melting point of the polymeric material under pressure; and
   e) releasing the pressure to about ambient pressure.

30. The method according to claim 7, wherein the oxidation-resistant medical implant is packaged and sterilized by ionizing radiation or gas sterilization, thereby forming a sterile and cross-linked oxidation-resistant medical implant.

31. The method according to claim 7, wherein the polymeric material is compression molded to another piece or a medical implant, thereby forming an interface or an interlocked hybrid material.

32. The method according to claim 7, wherein the antioxidant blended polymeric material is compression molded to another piece or a medical implant, thereby forming an interface or an interlocked hybrid material.

33. The method according to claim 7, wherein the consolidated antioxidant doped polymeric material is compression molded to another piece, thereby forming an interface and an interlocked hybrid material.

34. The method according to claim 7, wherein the consolidated polymeric material is compression molded to another piece, thereby forming an interface and an interlocked hybrid material.

35. The method according to claim 7, wherein the doping is carried out by soaking the medical implant in the antioxidant for about 0.1 hours to about 72 hours.

36. The method according to claim 7, wherein the doping is carried out by soaking the medical implant in the antioxidant for about an hour, about 2, 3, 4, 5, 6, 7, 8, 9, 10, 11, 12, 13, 14, 15, 16, or about 20 hours.

37. The method according to claim 7, wherein the antioxidant the doping is carried out at a temperature between room temperature and about 300° C.

38. The method according to claim 7, wherein the antioxidant is heated to about 120° C. and the doping is carried out at about 120° C.

39. The method according to claim 7, wherein the antioxidant is warmed to about room temperature and the doping is carried out at room temperature.

40. The method according to claim 7, wherein the cross-linked polymeric material is heated at a temperature below the melt or above the melt of the consolidated and cross-linked polymeric material.

41. The method according to claim 7, wherein the polymeric material is a polyethylene, polyolefin, a polypropylene, a polyamide, a polyether ketone, a hydrogel or a mixture thereof.

42. The method according to claim 41, wherein the polyethylene is selected from a group consisting of a low-density polyethylene, high-density polyethylene, linear low-density polyethylene, ultra-high molecular weight polyethylene (UHMWPE), or a mixture thereof.

43. The method according to claim 7, wherein the medical implant comprises medical devices selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, interpositional devices for any joint, sutures, tendons, heart valves, stents, vascular grafts.

44. The method according to claim 7, wherein the polymeric material is polymeric resin powder, polymeric flakes, polymeric particles, or the like, or a mixture thereof.

45. The method according to claim 7, wherein the irradiation is carried out in an atmosphere containing between about 1% and about 22% oxygen.

46. The method according to claim 7, wherein the irradiation is carried out in an inert atmosphere, wherein the inert atmosphere contains gas selected from the group consisting of nitrogen, argon, helium, neon, or the like, or a combination thereof.

47. The method according to claim 7, wherein the irradiation is carried out in a vacuum.

48. The method according to claim 7, wherein the cross-linked polymeric material is heated in an atmosphere containing between about 1% and about 22% oxygen.

49. The method according to claim 7, wherein the radiation dose is between about 25 and about 1000 kGy.

50. The method according to claim 7, wherein the radiation dose is about 65 kGy, about 75 kGy, or about 100 kGy.

51. The method according to claim 7, wherein the radiation is a gamma irradiation.

52. The method according to claim 7 wherein the radiation is an electron beam irradiation.

53. The method according to claim 7, wherein reduction of free radicals in the cross-linked polymeric material is achieved by heating the polymeric material in contact with a non-oxidizing medium.

54. The method according to claim 7, wherein reduction of free radicals in the cross-linked polymeric material is achieved by contacting with a non-oxidizing medium and heating the medium to above the melting temperature of the cross-linked polymeric material.

55. The method according to claim 53, wherein the non-oxidizing medium is an inert gas.

56. The method according to claim 53, wherein the non-oxidizing medium is an inert fluid.

57. The method according to claim 53, wherein the medium is a polyunsaturated hydrocarbon selected from the group consisting of: acetylenic hydrocarbons such as acetylene; conjugated or unconjugated olefinic hydrocarbons such as butadiene and (meth)acrylate monomers; and sulphur monochloride with chloro-tri-fluoroethylene (CTFE) or acetylene.

58. The method according to claim 7, wherein reduction of free radicals in the cross-linked polymeric material is achieved by heating the polymeric material to above the melting point of the cross-linked polymeric material.

59. The method according to claim 7, wherein the medical implant is soaked in a solution, of about 50% by weight, of the antioxidant in ethanol.

60. The method according to claim 7, wherein the medical implant is contacted, diffused, or homogenized with an antioxidant in a supercritical fluid.

61. The method of claim 60, wherein the supercritical fluid is $CO_2$.

62. The method according to claim 7, wherein the antioxidant is vitamin E.

63. The method according to claim 7, wherein the antioxidant is α-tocopherol.

64. The method according to claim 7, wherein the medical implant is a non-permanent medical device.

65. The method of claim 64, wherein the non-permanent medical device is a catheter, a balloon catheter, a tubing, an intravenous tubing, or a suture.

66. The method according to claim 7, wherein the cross-linked oxidation-resistant medical implant is packaged and sterilized by ionizing radiation or gas sterilization, thereby forming a sterile and oxidation-resistant cross-linked medical implant having a spatial distribution of antioxidant.

67. The method according to claim 7, wherein the antioxidant is diffused to a depth of about 5 mm or more from the surface.

68. The method according to claim 7, wherein the antioxidant is diffused to a depth of about 3-5 mm from the surface.

69. The method according to claim 7, wherein the antioxidant is diffused to a depth of about 1-3 mm from the surface.

70. The method according to claim 7, wherein the antioxidant-doped or -blended polymeric material is further homogenized at a temperature below the melting point of the polymeric material for a period of about an hour to several days.

71. The method according to claim 7, wherein the antioxidant-doped or -blended polymeric material is further homogenized at a temperature 130° C. for 36 hours.

72. The method according to claim 7, wherein the surface of the polymeric material is contacted with a lower concentration of antioxidant and bulk of the polymeric material is contacted with a higher concentration of antioxidant.

73. The method according to claim 17, wherein the surface of the polymeric material has a thickness of about 1.0 μm to about 2 cm.

74. The method according to claim 17, wherein the surface of the polymeric material has a thickness of about 1.0 mm to about 5 mm.

75. The method according to claim 17, wherein the surface of the polymeric material has a thickness of about 2 mm.

76. The method according to claim 17, wherein the bulk of the polymeric material has a thickness of about 1.0 μm to about 2 cm from the surface of the polymeric material to the center of the polymeric material.

77. The method of claim 17, wherein bulk of the polymeric material has a thickness of about 1.0 mm to about 5 mm from the surface of the polymeric material to the center of the polymeric material.

78. The method of claim 17, wherein bulk of the polymeric material has a thickness of about 2 mm from the surface of the polymeric material to the center of the polymeric material.

79. The method according to claim 17, wherein the blends of resin, flakes, or powder, the surface or the bulk of the polymeric material contain the same concentration of antioxidant.

80. The method according to claim 17, wherein the antioxidant is extracted or eluted by contacting the consolidated polymeric material with a solvent.

81. The method according to claim 80, wherein the antioxidant is soluble in the solvent.

82. The method according to claim 80, wherein the solvent is a hydrophobic solvent; an alcohol; or an aqueous solution.

83. The method according to claim 82, wherein the hydrophobic solvent is a hexane, heptane, or a longer chain alkane.

84. The method according to claim 82, wherein the alcohol is an ethanol, any member of the propanol or butanol family, or a longer chain alcohol.

85. A method of making an oxidation-resistant cross-linked polymeric material comprising:
  a) blending a polymeric material with an antioxidant;
  b) consolidating the antioxidant-blended polymeric material, thereby forming an oxidation-resistant polymeric material;
  c) extracting or eluting the antioxidant from the surface regions of the oxidation-resistant polymeric material by contacting the consolidated polymeric material with a solvent, wherein the solvent is a hydrophobic solvent; an alcohol; or an aqueous solution, and wherein the solvent is made by using an emulsifying agent; and
  d) irradiating the consolidated oxidation-resistant polymeric material with ionizing radiation, thereby forming an oxidation-resistant cross-linked polymeric material.

86. The method according to claim 85, wherein the emulsifying agent is Tween 80 or ethanol.

87. The method according to claim 7, wherein the oxidation-resistant polymeric material or the medical implant is further homogenized for about an hour to several days at room temperature to about 400° C., at 120° C. for 40 hours, or at 130° C. for about 40 hours.

88. The method according to claim 87, wherein the oxidation-resistant polymeric material or medical implant is homogenized at 120° C. for 24 hours.

89. The method according to claim 87, wherein the oxidation-resistant polymeric material or medical implant is homogenized at 130° C. for 36 hours.

90. The method according to claim 87, wherein the oxidation-resistant polymeric material or medical implant is homogenized before and/or after the extraction or elution of the antioxidant.

91. The method according to claim 87, wherein the oxidation-resistant polymeric material or medical implant is homogenized under ambient pressure.

92. The method according to claim 87, wherein the oxidation-resistant polymeric material or medical implant is homogenized in air, or in an inert atmosphere including nitrogen, argon, and/or the like.

93. The method according to claim 87, wherein the oxidation-resistant polymeric material or medical implant is homogenized in a chamber containing supercritical fluids such as carbon dioxide or the like.

94. The method of claim 80, wherein the solvent is a gas, a fluid, or a supercritical fluid.

95. The method according to claim 7, wherein the irradiation is carried out at a temperature that is above the room temperature and below the melting point of the polymeric material.

96. The method according to claim 7, wherein the irradiation is carried out at a temperature of about 40° C., about 75° C., about 100° C., about 110° C., about 120° C., about 130° C. or about 135° C.

97. The method according to claim 17, wherein the irradiation is carried out at a temperature that is above the room temperature and below about 135° C., below about 130° C., below about 120° C., below about 110° C., below about 100° C., below about 75° C., or below about 40° C.

98. The method according to any of the claim 26, wherein the doping is carried out by diffusion.

99. An oxidation-resistant cross-linked polymeric material or a medical implant comprising a polymeric material, wherein the polymeric material is obtained by a method according to claim 7.

100. An oxidation-resistant cross-linked polymeric material or a medical implant comprising a polymeric material, wherein the polymeric material is obtained by a method according to claim 17.

101. The method according to claim 7, wherein the radiation dose is about 150 kGy or about 200 kGy.

102. The method according to claim 7, wherein the oxidation-resistant polymeric material or the medical implant is further homogenized at 150° C. for 40 hours.

* * * * *

UNITED STATES PATENT AND TRADEMARK OFFICE
CERTIFICATE OF CORRECTION

PATENT NO. : 8,293,811 B2  
APPLICATION NO. : 12/522728  
DATED : October 23, 2012  
INVENTOR(S) : Orhun K. Muratoglu et al.

Page 1 of 1

It is certified that error appears in the above-identified patent and that said Letters Patent is hereby corrected as shown below:

Title Page 1, Field (86), Column 1, under "PCT Pub. No.", delete "PCT/US2008/092047" and insert --PCT/US2008/051982--.

Signed and Sealed this
Nineteenth Day of February, 2013

Teresa Stanek Rea
*Acting Director of the United States Patent and Trademark Office*